US012799121B2

(12) United States Patent
Zhao et al.

(10) Patent No.: US 12,799,121 B2
(45) Date of Patent: Nov. 17, 2026

(54) SUBSTITUTED PYRAZOLO[1,5-A]PYRIMIDINE-7-AMINE DERIVATIVES, COMPOSITIONS AND PHARMACEUTICAL USES THEREOF

(71) Applicants: SHANGHAI HAIYAN PHARMACEUTICAL TECHNOLOGY CO., LTD., Shanghai (CN); YANGTZE RIVER PHARMACEUTICAL GROUP CO., LTD., Taizhou (CN)

(72) Inventors: Zhiming Zhao, Shanghai (CN); Shenghua Wu, Shanghai (CN); Mojia Hua, Shanghai (CN); Yang Liu, Shanghai (CN); Shenglei Hao, Shanghai (CN); Lulu Wang, Shanghai (CN)

(73) Assignees: Shanghai Haiyan Pharmaceutical Technology Co., Ltd., Shanghai (CN); Yangtze River Pharmaceutical Group Co., Ltd., Taizhou (CN)

( * ) Notice: Subject to any disclaimer, the term of this patent is extended or adjusted under 35 U.S.C. 154(b) by 527 days.

(21) Appl. No.: 18/262,534

(22) PCT Filed: Jan. 21, 2022

(86) PCT No.: PCT/CN2022/073252

§ 371 (c)(1),
(2) Date: Jul. 21, 2023

(87) PCT Pub. No.: WO2022/156779

PCT Pub. Date: Jul. 28, 2022

(65) Prior Publication Data

US 2024/0109898 A1 Apr. 4, 2024

(30) Foreign Application Priority Data

Jan. 22, 2021 (CN) ........................ 202110087029.8
Aug. 4, 2021 (CN) ........................ 202110892176.2

(51) Int. Cl.
*C07D 487/04* (2006.01)
*A61P 35/00* (2006.01)
*A61P 35/02* (2006.01)

(52) U.S. Cl.
CPC ............ *C07D 487/04* (2013.01); *A61P 35/00* (2018.01); *A61P 35/02* (2018.01)

(58) Field of Classification Search
None
See application file for complete search history.

(56) References Cited

FOREIGN PATENT DOCUMENTS

| | | | |
|---|---|---|---|
| CN | 101054380 | A | 10/2007 |
| CN | 101321757 | A | 12/2008 |

(Continued)

OTHER PUBLICATIONS

Lima et al., Current Topics in Medicinal Chemistry, 2019, vol. 19, No. 19 p. 1734-1750 (Year: 2019).*

(Continued)

*Primary Examiner* — Jeffrey S Lundgren
*Assistant Examiner* — Anthony Joseph Seitz
(74) *Attorney, Agent, or Firm* — Lee & Hayes, P.C.

(57) ABSTRACT

A substituted pyrazolo[1,5-alpyrimidin-7-amine derivative, the structure of which is represented by formula (1), or pharmaceutically acceptable salts, solvates, stereoisomers, prodrugs, drug compositions thereof. The derivative has significant CDK9-selective inhibitory activity.

(Continued)

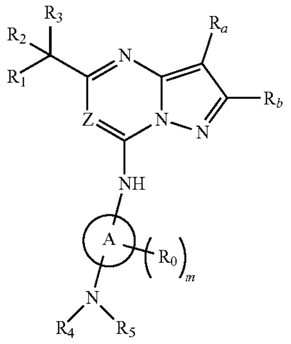

(I)

11 Claims, 4 Drawing Sheets

(56) References Cited

FOREIGN PATENT DOCUMENTS

| | | | | | |
|---|---|---|---|---|---|
| CN | 106103445 A | | 11/2016 | | |
| CN | 107427521 A | * | 12/2017 | ......... | C07K 14/4738 |
| JP | 2018515434 A | | 6/2018 | | |
| RU | 2441005 C2 | | 1/2012 | | |
| WO | WO2016160617 A2 | | 10/2016 | | |
| WO | WO-2020092134 A1 | * | 5/2020 | ........... | C12Q 1/6844 |
| WO | WO2020092314 A1 | | 5/2020 | | |
| WO | WO2021216828 A1 | | 10/2021 | | |
| WO | WO-2022098843 A1 | * | 5/2022 | ............. | A61K 47/55 |
| WO | WO2022156779 A1 | | 7/2022 | | |

OTHER PUBLICATIONS

Franco et al., CDK9: A key player in cancer and other diseases. J Cell Biochem. 2018; 119: 1273-1284 (Year: 2018).*

Australian Office Action for Australian Application No. 2022211514 dated Dec. 12, 2023, 4 pages.

International Search Report and Written Opinion mailed Apr. 24, 2022 in International Application No. PCT/CN2022/073252, 19 pages.

Zhao et al., "Design and synthesis of novel pyrazolo[1, 5-a]pyrimidine derivatives bearing nitrogen mustard moiety and evaluation of their antitumor activity in vitro and in vivo," Apr. 2016, 119:183-196.

Office Action for Japanese Application No. 2023-544606, Dated Jun. 20, 2024, 18 pages.

Office Action for Russian Application No. 2023121829/04(047772). Dated Feb. 27, 2024, 32 pages.

* cited by examiner

SUBSTITUTED PYRAZOLO[1,5-A]PYRIMIDINE-7-AMINE DERIVATIVES, COMPOSITIONS AND PHARMACEUTICAL USES THEREOF

CROSS REFERENCE TO RELATED APPLICATIONS

This application is a U.S. National Stage Application of International Application No. PCT/CN2022/073252, filed Jan. 21, 2022, which claims the benefit of Chinese Application No. 202110892176.2, filed Aug. 4, 2021, and Chinese Application No. 202110087029.8, filed Jan. 22, 2021, all of which are incorporated herein by reference in their entirety.

FIELD

The present disclosure relates to the field of pharmaceutical technology, and particularly, to a substituted pyrazolo [1,5-a]pyrimidin-7-amine derivative, a pharmaceutically acceptable salt, solvate, stereoisomer, prodrug, pharmaceutical composition and pharmaceutical use thereof.

BACKGROUND

The family of cyclin-dependent kinases (CDKs) proteins consists of members (cell cycle CDKs), involving in the gene transcription regulation (transcriptional CDKs), of the key regulators of the cell division cycle and members with other functions. CDKs activate binding to cyclin regulatory subunits. CDK1/cyclin B, CDK2/cyclin A, CDK2/cyclin E, CDK4/cyclin D, and CDK6/cyclin D of the cell cycle CDKs were sequentially activated to drive cells into and through the cell division cycle. CDK9/cyclin T and CDK7/cyclin H of the transcriptional CDKs regulate the activity of RNA polymerase II through phosphorylation of the carboxy-terminal domain (CTD).

CDK9 was a catalytic subunit in the positive transcription elongation factor b (P-TEFb) complex for regulating transcription elongation of genes by phosphorylating the carbon-terminal region of RNA complex II, and it maps to the RNA transcription elongation regulatory kinase on chromosome 9q34.1. CDK9 was widely expressed in many eukaryotic cells and human tissues. CDK9 kinase was highly expressed in cardiomyocytes, hepatocytes, hematopoietic tissues, adipocytes, neurons, and muscle cells, and was also generally highly expressed in tumor cells. CDK9 was also an important factor in tumor cell progression and maintenance. CDK9 inhibitors down-regulate the expression of related oncoprotein (MYC) and the expression of apoptosis inhibitor protein Mcl-1 by inhibiting the transcription elongation of genes, thereby promoting apoptosis of cancer cells. By regulating the epigenetic factor BRG1, CDK9 inhibitors reactivate silenced genes, including activation of ERVs in tumor cells, and promote interferon expression, allowing the tumor cells to be more sensitive to immunotherapy.

Currently, several enterprises have developed CDK9 inhibitors, including selective CDK9 inhibitor BAY1251152 developed by Bayer, selective CDK9 inhibitor AZD4573 developed by AstraZeneca, non-selective CDK9 inhibitor TP-1287 developed by Tolero, and non-selective CDK9 inhibitor QHRD107 developed by Qianhong Bio-pharma (Changzhou). However, at present, most of the selective CDK9 inhibitors were still in the early stage of clinical development, and their selective inhibitory activity on CDK9 and in vivo pharmacokinetic parameters need to be further improved. Therefore, it was of important clinical significance to develop new CDK9 inhibitors with high activity and selectivity and reduced in vivo toxicity.

SUMMARY

The object of the present disclosure was to provide substituted pyrazolo[1,5-a]pyrimidin-7-amine derivatives having high inhibitory activity against CDK9, good selectivity, and better pharmacokinetic parameters.

A first aspect of the present disclosure provides a compound represented by formula (I), or a pharmaceutically acceptable salt thereof, or a stereoisomer thereof, or a solvate thereof, or a prodrug thereof:

(I)

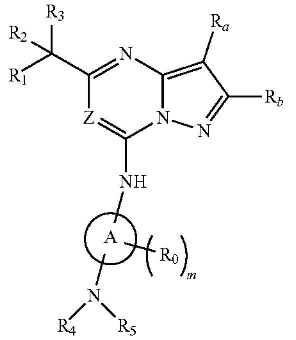

where:

$R_1$ was $C_{3-8}$ cycloalkyl (preferably $C_{3-6}$ cycloalkyl), $C_{2-8}$ alkenyl (preferably $C_{2-6}$ alkenyl, more preferably $C_{2-4}$ alkenyl), or $C_{2-8}$ alkynyl (preferably $C_{2-6}$ alkynyl, more preferably $C_{2-4}$ alkynyl); the $C_{3-8}$ cycloalkyl, $C_{2-8}$ alkenyl and $C_{2-8}$ alkynyl were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, halogenated $C_{1-3}$ alkyl, halogenated $C_{1-3}$ alkoxy, $NR_{a1}R_{b1}$, $-SO_2C_{1-3}$ alkyl, $-C(O)NR_{a1}R_{b1}$, $-C(O)C_{1-3}$ alkyl, $-C(O)OC_{1-3}$ alkyl, $-OC(O)C_{1-3}$ alkyl, $C_{3-6}$ cycloalkyl, $C_{3-6}$ cycloalkoxy, three- to six-membered heterocycloalkyl, and phenyl, wherein the phenyl was optionally substituted with 1, 2, or 3 substituents each independently selected from a substituent group S;

$R_2$ and $R_3$ were each independently hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), $C_{1-8}$ alkoxy (preferably $C_{1-6}$ alkoxy, more preferably $C_{1-3}$ alkoxy), cyano, hydroxyl, carboxyl, halogen (preferably fluorine or chlorine), $-C(O)NR_{a0}R_{b0}$, $-C(O)C_{1-8}$ alkyl (preferably $-C(O)C_{1-6}$ alkyl, more preferably $-C(O)C_{1-3}$ alkyl, $-C(O)OC_{1-8}$ alkyl (preferably $-C(O)OC_{1-6}$ alkyl, more preferably $-C(O)OC_{1-3}$ alkyl), or $-OC(O)C_{1-8}$ alkyl (preferably $-OC(O)C_{1-6}$ alkyl, more preferably $-OC(O)C_{1-3}$ alkyl), wherein the $C_{1-8}$ alkyl, $C_{1-8}$ alkoxy, and $C_{3-8}$ cycloalkyl were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, $NR_{a1}R_{b1}$, $-SO_2C_{1-3}$ alkyl, $-S(O)C_{1-3}$ alkyl, $-C(O)NR_{a1}R_{b1}$, $-C(O)OC_{1-3}$ alkyl, $-OC(O)C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from a substituent group S;

$R_4$ and $R_5$ were each independently hydrogen, $C_{1-8}$ alkyl (preferably $C_{1-6}$ alkyl, more preferably $C_{1-3}$ alkyl), —C(O)O$C_{1-8}$ alkyl (preferably —C(O)O$C_{1-6}$ alkyl, more preferably —C(O)O$C_{1-3}$ alkyl), —C(O)$C_{1-8}$ alkyl (preferably —C(O)$C_{1-6}$ alkyl, more preferably —C(O)($C_{1-3}$ alkyl), —(C═N)—$C_{1-8}$ alkyl (preferably —(C═N)—$C_{1-6}$ alkyl, more preferably —(C═N)—$C_{1-3}$ alkyl), or —(C═N)—N$R_{a0}R_{b0}$; or $R_4$, $R_5$ together with the nitrogen atom linked thereto form a three- to seven-membered saturated or partially unsaturated monoheterocyclic ring, wherein the three to seven-membered saturated or partially unsaturated monoheterocyclic ring was unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, N$R_{a1}R_{b1}$, —S$O_2C_{1-3}$ alkyl, —S(O)$C_{1-3}$ alkyl, —C(O)N$R_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, and three- to six-membered heterocycloalkyl;

Z was N or C$R_Z$, wherein $R_Z$ was hydrogen, cyano, hydroxyl, carboxyl, halogen (preferably fluorine or chlorine), $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), —C(O)$C_{1-8}$ alkyl (preferably —C(O)$C_{1-6}$ alkyl, more preferably —C(O)($C_{1-3}$ alkyl), —C(O)O$C_{1-8}$ alkyl (preferably —C(O)O$C_{1-6}$ alkyl, more preferably —C(O)O$C_{1-3}$ alkyl), —C(O)N$R_{a0}R_{b0}$, five- to six-membered heteroaryl, or eight- to ten-membered heteroaryl, wherein the $C_{1-8}$ alkyl and the $C_{1-8}$ alkoxy were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, N$R_{a1}R_{b1}$, —S$O_2C_{1-3}$ alkyl, —S(O)$C_{1-3}$ alkyl, —C(O)N$R_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from the substituent group S;

$R_a$ and $R_b$ were each independently hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), $C_{1-8}$ alkoxy (preferably $C_{1-6}$ alkoxy, more preferably $C_{1-3}$ alkoxy), cyano, hydroxyl, carboxyl, halogen (preferably fluorine or chlorine), —C(O)N$R_{a0}R_{b0}$, —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —OC(O)$C_{1-8}$ alkyl (preferably —OC(O)$C_{1-6}$ alkyl, more preferably —OC(O)$C_{1-3}$ alkyl), —S$O_2C_{1-8}$ alkyl (preferably —S$O_2C_{1-6}$ alkyl, more preferably —S$O_2C_{1-3}$ alkyl, or —S$O_2$N$R_{a0}R_{b0}$; or $R_a$ and $R_b$ were joined to form a fused three- to seven-membered saturated or partially unsaturated monoheterocyclic ring, or a fused three- to seven-membered saturated or partially unsaturated monocyclic ring, wherein the $C_{1-8}$ alkyl, the $C_{1-8}$ alkoxy, the three- to seven-membered saturated or partially unsaturated monoheterocyclic ring, and the three- to seven-membered saturated or partially unsaturated monocyclic ring were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, N$R_{a1}R_{b1}$, —S$O_2C_{1-3}$ alkyl, —S(O)$C_{1-3}$ alkyl, —C(O)N$R_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from the substituent group S;

ring A was a three- to seven-membered saturated or partially unsaturated monoheterocyclic ring, or a three- to seven-membered saturated or partially unsaturated monocyclic ring;

$(R_0)_m$ represents that hydrogens on ring A were substituted with m $R_0$ groups, m being 0, 1, 2 or 3, wherein each $R_0$ was identical or different and independently cyano, hydroxyl, carboxyl, halogen (preferably fluorine or chlorine), $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), —C(O)$C_{1-8}$ alkyl (preferably —C(O)$C_{1-6}$ alkyl, more preferably —C(O)$C_{1-3}$ alkyl), —C(O)O$C_{1-8}$ alkyl (preferably —C(O)O$C_{1-6}$ alkyl, more preferably —C(O)O$C_{1-3}$ alkyl), —OC(O)$C_{1-8}$ alkyl (preferably —OC(O)$C_{1-6}$ alkyl, more preferably —OC(O)$C_{1-3}$ alkyl), or —C(O)N$R_{a0}R_{b0}$; or wherein any two $R_0$ groups linked to the same ring atom or different ring atoms were joined to form a three- to seven-membered saturated or partially unsaturated monoheterocyclic ring, or a three- to seven-membered saturated or partially unsaturated monocyclic ring, wherein the $C_{1-8}$ alkyl, the $C_{1-8}$ alkoxy, the three- to seven-membered saturated or partially unsaturated monoheterocyclic ring, and the three- to seven-membered saturated or partially unsaturated monocyclic ring were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, N$R_{a1}R_{b1}$, —S$O_2C_{1-3}$ alkyl, —S(O)$C_{1-3}$ alkyl, —C(O)N$R_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from the substituent group S;

the substituent group S consists of halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, N$R_{a1}R_{b1}$, —S$O_2C_{1-3}$ alkyl, —S(O)$C_{1-3}$ alkyl, —C(O)N$R_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, three- to six-membered heterocycloalkyl, phenyl, and five- to six-membered heteroaryl;

$R_{a0}$ and $R_{b0}$ were each independently hydrogen, $C_{1-3}$ alkyl, or acetyl; or $R_{a0}$ and $R_{b0}$ together with the nitrogen atom linked thereto form a four- to six-membered saturated monoheterocyclic ring, wherein the four- to six-membered saturated monoheterocyclic ring was optionally substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, —$SO_2C_{1-3}$ alkyl, —$S(O)C_{1-3}$ alkyl, —C(O)$NH_2$, —C(O)NH($C_{1-3}$ alkyl), —C(O)N($C_{1-3}$ alkyl)$_2$, —C(O)$OC_{1-3}$ alkyl, —OC(O)$C_{1-3}$ alkyl, $C_{3-6}$ cycloalkyl, $C_{3-6}$ cycloalkoxy, and three- to six-membered heterocycloalkyl; and $R_{a1}$ and $R_{b1}$ were each independently hydrogen, $C_{1-3}$ alkyl, or acetyl; or $R_{a1}$ and $R_{b1}$ together with the nitrogen atom linked thereto form a four- to six-membered saturated monoheterocyclic ring, wherein the four- to six-membered saturated monoheterocyclic ring was optionally substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, —$SO_2C_{1-3}$ alkyl, —$S(O)C_{1-3}$ alkyl, —C(O)$NH_2$, —C(O)NH($C_{1-3}$ alkyl), —C(O)N($C_{1-3}$ alkyl)$_2$, —C(O)$OC_{1-3}$ alkyl, —OC(O)$C_{1-3}$ alkyl, $C_{3-6}$ cycloalkyl, $C_{3-6}$ cycloalkoxy, and three- to six-membered heterocycloalkyl.

In some embodiments, the compound represented by formula (I) has a structure represented by formula (II):

(II)

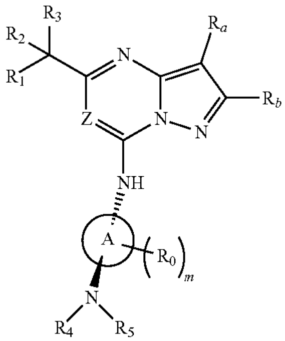

where the respective groups were as defined above.

In some embodiments, $R_1$ was $C_{3-8}$ cycloalkyl (preferably $C_{3-6}$ cycloalkyl), or $C_{2-8}$ alkenyl (preferably $C_{2-6}$ alkenyl, more preferably $C_{2-4}$ alkenyl); and $R_2$ and $R_3$ were each independently hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), or deuterated $C_{1-8}$ alkyl (preferably deuterated $C_{1-6}$ alkyl, more preferably deuterated $C_{1-3}$ alkyl), wherein the $C_{3-8}$ cycloalkyl and the $C_{2-8}$ alkenyl were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, halogenated $C_{1-3}$ alkyl, halogenated $C_{1-3}$ alkoxy, $NR_{a1}R_{b1}$, —$SO_2C_{1-3}$ alkyl, —C(O)$NR_{a1}R_{b1}$, —C(O)$C_{1-3}$ alkyl, and —C(O)$OC_{1-3}$ alkyl.

In some embodiments, $R_1$ was $C_{3-8}$ cycloalkyl (preferably $C_{3-6}$ cycloalkyl), or $C_{2-8}$ alkenyl (preferably $C_{2-6}$ alkenyl, more preferably $C_{2-4}$ alkenyl); $R_2$ was hydrogen or $C_{1-8}$ alkyl (preferably $C_{1-6}$ alkyl, more preferably $C_{1-3}$ alkyl); and $R_3$ was hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), or deuterated $C_{1-8}$ alkyl (preferably deuterated $C_{1-6}$ alkyl, more preferably deuterated $C_{1-3}$ alkyl), wherein the $C_{3-8}$ cycloalkyl and the $C_{2-8}$ alkenyl were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, halogenated $C_{1-3}$ alkyl, halogenated $C_{1-3}$ alkoxy, and $NR_{a1}R_{b1}$.

In some embodiments, $R_1$ was cyclopropyl, cyclobutyl, cyclopentyl, cyclohexyl, 1-methylcyclopropyl, 1-methylcyclobutyl, 1-methylcyclopentyl, 1-methylcyclohexyl, ethenyl, propenyl, iso-propenyl, n-butenyl, iso-butenyl, pentenyl, or hexenyl; and $R_2$ and $R_3$ were each independently hydrogen, methyl, ethyl, n-propyl, isopropyl, n-butyl, isobutyl, tert-butyl, sec-butyl, n-pentyl, cyclopropyl, cyclobutyl, cyclopentyl, cyclohexyl, 1-methylcyclopropyl, 1-methylcyclobutyl, 1-methylcyclopentyl, 1-methylcyclohexyl, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, monodeuteromethyl, monodeuteroethyl, dideuteromethyl, dideuteroethyl, trideuteromethyl, or trideuterethyl.

In some embodiments, Z was CH.

In some embodiments, the three- to seven-membered saturated or partially unsaturated monoheterocyclic ring for the ring A was selected from: an azetidine ring, an oxetane ring, a tetrahydrofuran ring, a tetrahydrothiophene ring, a tetrahydropyrrole ring, a piperidine ring, a pyrroline ring, an oxazolidine ring, a piperazine ring, a dioxolane ring, a dioxane ring, a morpholine ring, a thiomorpholine ring, a thiomorpholine-1,1-dioxide ring, a tetrahydropyran ring, an azetidin-2-one ring, an oxetan-2-one ring, a pyrrolidin-2-one ring, a pyrrolidine-2,5-dione ring, a piperidin-2-one ring, a dihydrofuran-2(3H)-one ring, a dihydrofuran-2,5-dione ring, a tetrahydro-2H-pyran-2-one ring, a piperazin-2-one ring, a morpholin-3-one ring, a 1,2-dihydroazetidinium ring, a 1,2-dihydrooxacyclobutadiene ring, a 2,5-dihydro-TH-pyrrole ring, a 2,5-dihydrofuran ring, a 2,3-dihydrofuran ring, a 2,3-dihydro-1H-pyrrole ring, a 3,4-dihydro-2H-pyran ring, a 1,2,3,4-tetrahydropyridine ring, a 3,6-dihydro-2H-pyran ring, a 1,2,3,6-tetrahydropyridine ring, a 4,5-dihydro-TH-imidazole ring, a 1,4,5,6-tetrahydropyrimidine ring, a 3,4,7,8-tetrahydro-2H-1,4,6-oxadiazoxazine ring, a 1,6-dihydropyrimidine ring, a 4,5,6,7-tetrahydro-TH-1,3-diazepine ring, or a 2,5,6,7-tetrahydro-1,3,5-oxadiazepine ring.

In some embodiments, the three- to seven-membered saturated or partially unsaturated monocyclic ring for the ring A was selected from: a cyclopropyl ring, a cyclobutyl ring, a cyclopentyl ring, a cyclopentenyl ring, a cyclohexyl ring, a cyclohexenyl ring, a cyclohexadienyl ring, a cycloheptyl ring, a cycloheptatrienyl ring, a cyclopentanone ring, or a cyclopentane-1,3-dione ring.

In some embodiments, the compound represented by formula (I) has a structure represented by formula (III-a) or formula (III-b):

(III-a)

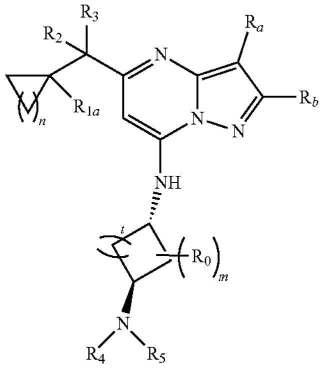

(III-b)

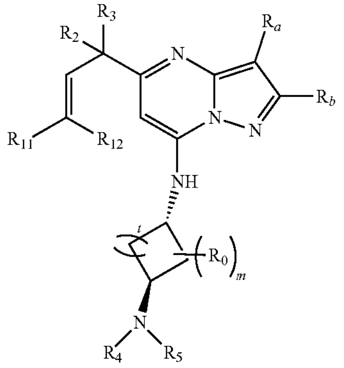

where $R_{1a}$ was hydrogen, $C_{1-6}$ alkyl (preferably $C_{1-3}$ alkyl), or deuterated $C_{1-6}$ alkyl (more preferably deuterated $C_{1-3}$ alkyl); n was 1, 2, 3, 4, 5 or 6; t was 0, 1, 2, 3 or 4; and $R_{11}$ and $R_{12}$ were each independently hydrogen, $C_{1-3}$ alkyl, or halogen, and the remaining groups were as defined above.

In some embodiments, $R_2$ and $R_3$ were each independently hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), or deuterated $C_{1-8}$ alkyl (preferably deuterated $C_{1-6}$ alkyl, more preferably deuterated $C_{1-3}$ alkyl), wherein the $C_{3-8}$ cycloalkyl was unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, halogenated $C_{1-3}$ alkyl, halogenated $C_{1-3}$ alkoxy, $NR_{a1}R_{b1}$, —$SO_2C_{1-3}$ alkyl, —$C(O)NR_{a1}R_{b1}$, —$C(O)C_{1-3}$ alkyl, and —$C(O)OC_{1-3}$ alkyl.

In some embodiments, $R_2$ was hydrogen or $C_{1-8}$ alkyl (preferably $C_{1-6}$ alkyl, more preferably $C_{1-3}$ alkyl); $R_3$ was hydrogen, $C_{1-8}$ alkyl (preferably $C_{1-6}$ alkyl, more preferably $C_{1-3}$ alkyl), $C_{3-8}$ cycloalkyl (preferably $C_{3-6}$ cycloalkyl), halogenated $C_{1-8}$ alkyl (preferably halogenated $C_{1-6}$ alkyl, more preferably halogenated $C_{1-3}$ alkyl), or deuterated $C_{1-8}$ alkyl (preferably deuterated $C_{1-6}$ alkyl, more preferably deuterated $C_{1-3}$ alkyl), wherein the $C_{3-8}$ cycloalkyl was unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, halogenated $C_{1-3}$ alkyl, halogenated $C_{1-3}$ alkoxy, and $NR_{a1}R_{b1}$.

In some embodiments, $R_2$ and $R_3$ were each independently hydrogen, methyl, ethyl, n-propyl, isopropyl, n-butyl, isobutyl, tert-butyl, sec-butyl, n-pentyl, cyclopropyl, cyclobutyl, cyclopentyl, cyclohexyl, 1-methylcyclopropyl, 1-methylcyclobutyl, 1-methylcyclopentyl, 1-methylcyclohexyl, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, monodeuteromethyl, monodeuteroethyl, dideuteromethyl, dideuterethyl, trideuteromethyl, or trideuterethyl.

In some embodiments, the compound represented by formula (III-a) has a structure represented by formula (III-a-1) or formula (III-a-2):

(III-a-1)

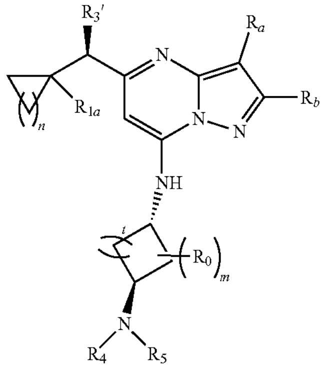

(III-a-2)

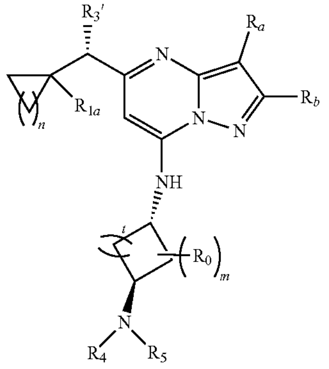

where $R_{3'}$ was $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), cyano, hydroxyl, carboxyl, halogen (preferably fluorine or chlorine), —$C(O)NR_{a0}R_{b0}$, —$C(O)C_{1-8}$ alkyl (preferably —$C(O)C_{1-6}$ alkyl, more preferably —$C(O)C_{1-3}$ alkyl), —$C(O)OC_{1-8}$ alkyl (preferably —$C(O)OC_{1-6}$ alkyl, more preferably —$C(O)OC_{1-3}$ alkyl), or —$OC(O)C_{1-8}$ alkyl (preferably —$OC(O)C_{1-6}$ alkyl, more preferably —$OC(O)C_{1-3}$ alkyl), wherein the $C_{1-8}$ alkyl and the $C_{1-8}$ alkoxy were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, $NR_{a1}R_{b1}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from the substituent group S; the other groups are defined as above.

In some embodiments, the compound represented by formula (III-a) has a structure represented by formula (III-a-3):

(III-a-3)

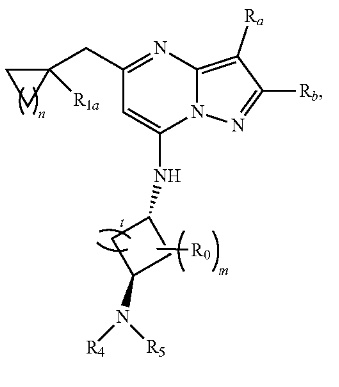

where the groups were as defined above.

In some embodiments, $R_{3'}$ was $C_{1-8}$ alkyl (preferably $C_{1-6}$ alkyl, more preferably $C_{1-3}$ alkyl), halogenated $C_{1-8}$ alkyl (preferably halogenated $C_{1-6}$ alkyl, more preferably halogenated $C_{1-3}$ alkyl), or deuterated $C_{1-8}$ alkyl (preferably deuterated $C_{1-6}$ alkyl, more preferably deuterated $C_{1-3}$ alkyl).

In some embodiments, $R_{3'}$ was methyl, ethyl, n-propyl, isopropyl, n-butyl, isobutyl, tert-butyl, sec-butyl, n-pentyl, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, monodeuteromethyl, monodeuteroethyl, dideuteromethyl, dideuteroethyl, or trideuteromethyl, trideuterioethyl.

In some embodiments, in the structure represented by formula (III-a), formula (III-a-1), or formula (III-a-2), t was 1 or 2, m was 0, $R_4$ was H, and $R_5$ was H, —C(O)$C_{1-3}$ alkyl, —C(O)O$C_{1-3}$ alkyl, —(C═N)—$C_{1-3}$ alkyl, or —(C═N)—$NH_2$.

In some embodiments, $R_a$ and $R_b$ were each independently hydrogen, $C_{1-6}$ alkyl (preferably $C_{1-3}$ alkyl), $C_{3-6}$ cycloalkyl, $C_{1-6}$ alkoxy (preferably $C_{1-3}$ alkoxy), halogenated $C_{1-6}$ alkyl (preferably halogenated $C_{1-3}$ alkyl), cyano, hydroxyl, carboxyl, halogen (preferably fluorine or chlorine), —C(O)$NR_{a0}R_{b0}$, —C(O)$C_{1-6}$ alkyl (preferably —C(O)$C_{1-3}$ alkyl), —C(O)O$C_{1-6}$ alkyl (preferably —C(O)O$C_{1-3}$ alkyl), —OC(O)$C_{1-6}$ alkyl (preferably —OC(O)$C_{1-3}$ alkyl), —$SO_2C_{1-6}$ alkyl (preferably —$SO_2C_{1-3}$ alkyl), or —$SO_2NR_{a0}R_{b0}$, wherein the $C_{1-6}$ alkyl and the $C_{1-6}$ alkoxy were unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, $NR_{a1}R_{b1}$, —$SO_2C_{1-3}$ alkyl, —S(O)$C_{1-3}$ alkyl, —C(O)$NR_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein the phenyl and the five- to six-membered heteroaryl were optionally substituted with 1, 2 or 3 substituents each independently selected from a substituent group S.

In some embodiments, $R_a$ and $R_b$ were each independently hydrogen, methyl, ethyl, n-propyl, isopropyl, n-butyl, isobutyl, tert-butyl, sec-butyl, n-pentyl, cyclopropyl, cyclobutyl, cyclopentyl, cyclohexyl, methoxy, ethoxy, n-propoxy, isopropoxy, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, monodeuteromethyl, monodeuteroethyl, dideuteromethyl, dideuteroethyl, trideuteromethyl, trideuterioethyl, cyano, hydroxyl, carboxyl, halogen (preferably fluorine or chlorine), —C(O)$NH_2$, —C(O)NH($C_{1-3}$ alkyl), —C(O)N($C_{1-3}$ alkyl) 2, —C(O)$C_{1-6}$ alkyl (preferably —C(O)$C_{1-3}$ alkyl), —C(O)O$C_{1-6}$ alkyl (preferably —C(O)O$C_{1-3}$ alkyl), —OC(O)$C_{1-6}$ alkyl (preferably —OC(O)$C_{1-3}$ alkyl), —$SO_2C_{1-6}$ alkyl (preferably —$SO_2C_{1-3}$ alkyl, —$SO_2NH_2$, —$SO_2$NH($C_{1-3}$ alkyl), or —$SO_2$N($C_{1-3}$ alkyl$)_2$.

In some embodiments, $R_4$ and $R_5$ were each independently hydrogen, $C_{1-8}$ alkyl (preferably $C_{1-6}$ alkyl, more preferably $C_{1-3}$ alkyl), —C(O)O$C_{1-8}$ alkyl (preferably —C(O)O$C_{1-6}$ alkyl, more preferably —C(O)O$C_{1-3}$ alkyl); or $R_4$ and $R_5$ together with the nitrogen atom linked thereto form a three- to seven-membered saturated or partially unsaturated monoheterocyclic ring, wherein the three- to seven-membered saturated or partially unsaturated monoheterocyclic ring was unsubstituted or substituted with 1, 2 or 3 substituents each independently selected from the group consisting of deuterium, halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, $NR_{a1}R_{b1}$, —$SO_2C_{1-3}$ alkyl, —S(O)$C_{1-3}$ alkyl, —C(O)$NR_{a1}R_{b1}$, —C(O)O$C_{1-3}$ alkyl, —OC(O)$C_{1-3}$ alkyl, $C_{3-6}$ cycloalkyl, $C_{3-6}$ cycloalkoxy, and three- to six-membered heterocycloalkyl.

In some embodiments, the three- to seven-membered saturated or partially unsaturated monoheterocyclic ring, which was formed by $R_4$ and $R_5$ together with the nitrogen atom linked thereto, was a four- to six-membered saturated monoheterocyclic ring selected from: azetidine, a tetrahydropyrrole ring, a piperidine ring, a piperazine ring, a morpholine ring, a thiomorpholine ring, a thiomorpholine-1,1-dioxide, 1,2-dihydroazetidine ring, a 2,5-dihydro-1H-pyrrole ring, a 2,3-dihydro-TH-pyrrole ring, a 1,2,3,4-tetrahydropyridine ring, or a 1,2,3,6-tetrahydropyridine ring.

In some embodiments, the fused three- to seven-membered saturated or partially unsaturated monoheterocyclic ring formed by joining $R_a$ and $R_b$ was a fused four- to six-membered saturated monoheterocyclic ring selected from: fused azetidine, fused oxetane, a fused tetrahydrofuran ring, a fused tetrahydrothiophene ring, a fused tetrahydropyrrol ring, a fused piperidine ring, a fused piperazine ring, a fused morpholine ring, a fused thiomorpholine ring, a fused thiomorpholine-1,1-dioxide, a fused tetrahydropyran ring, a fused 1,2-dihydroazetidine ring, a fused 1,2-dihydrooxobutadiene ring, a fused 2,5-dihydro-1H-pyrrole ring, a fused 2,5-dihydrofuran ring, a fused 2,3-dihydrofuran ring, a fused 2,3-dihydro-1H-pyrrole ring, a fused 3,4-dihydro-2H-pyran ring, a fused 1,2,3,4-tetrahydropyridine ring, a fused 3,6-dihydro-2H-pyran ring, or a fused 1,2,3,6-tetrahydropyridine ring.

In some embodiments, the fused three- to seven-membered saturated or partially unsaturated monocyclic ring formed by joining $R_a$ and $R_b$ was a fused three- to six-membered saturated monocyclic ring selected from: a fused cyclopropyl ring, a fused cyclobutyl ring, a fused cyclopentyl ring, a fused cyclopentenyl ring, a fused cyclohexyl ring, a fused cyclohexenyl ring, or a fused cyclohexadienyl ring.

In some embodiments, a three- to seven-membered saturated or partially unsaturated monoheterocyclic ring, which was formed by joining any two $R_0$ groups linked to the same ring atom or different ring atoms, was a four- to six-membered saturated monoheterocyclic ring selected from:

azetidine, oxetane, a tetrahydrofuran ring, a tetrahydrothiophene ring, tetrahydropyrrole ring, a piperidine ring, a piperazine ring, a morpholine ring, a thiomorpholine ring, thiomorpholine-1,1-dioxide, or a tetrahydropyran ring.

In some embodiments, a three- to seven-membered saturated or partially unsaturated monocyclic ring, which was formed by joining any two $R_0$ groups linked to the same ring atom or different ring atoms, was a three- to six-membered saturated monocyclic ring selected from: a cyclopropyl ring, a cyclobutyl ring, a cyclopentyl ring, or cyclohexyl ring.

In some embodiments, a four- to six-membered saturated monoheterocyclic ring, which was formed by $R_{a0}$ and $R_{b0}$ together with the nitrogen atom attached thereof, was selected from: azetidine, oxetane, a tetrahydrofuran ring, a tetrahydrothiophene ring, a tetrahydropyrrole ring, a piperidine ring, a piperazine ring, a morpholine ring, a thiomorpholine ring, thiomorpholine-1,1-dioxide, or a tetrahydropyran ring.

In some embodiments, a four- to six-membered saturated monoheterocyclic ring, which was formed by $R_{a1}$ and $R_{b1}$ together with the nitrogen atom attached thereto, was selected from: azetidine, oxetane, a tetrahydrofuran ring, a tetrahydrothiophene ring, a tetrahydropyrrole ring, a piperidine ring, a piperazine ring, a morpholine ring, a thiomorpholine ring, thiomorpholine-1,1-dioxide, or a tetrahydropyran ring.

In some embodiments, in the respective formulas, the five- to six-membered heteroaryl among the respective groups was independently selected from: thienyl, furyl, thiazolyl, isothiazolyl, imidazolyl, oxazolyl, pyrrolyl, pyrazolyl, triazolyl, 1,2,3-triazolyl, 1,2,4-triazolyl, 1,2,5-triazolyl, 1,3,4-triazolyl, tetrazolyl, isoxazolyl, oxadiazolyl, 1,2,3-oxadiazolyl, 1,2,4-oxadiazolyl, 1,2,5-oxadiazolyl, 1,3,4-oxadiazolyl, thiadiazolyl, pyridyl, pyridazinyl, pyrimidinyl, pyrazinyl, triazinyl, or tetrazinyl.

In some embodiments, the five- to six-membered heteroaryl was selected from:

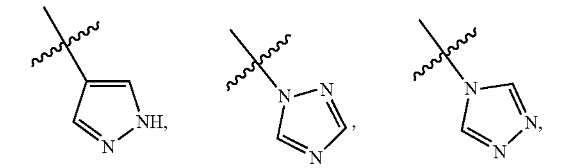

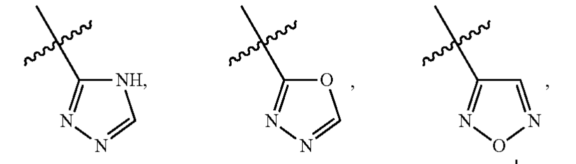

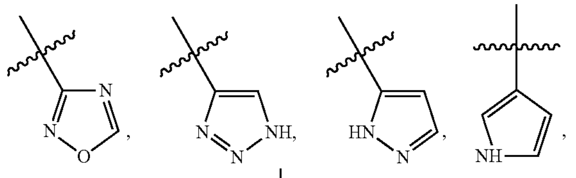

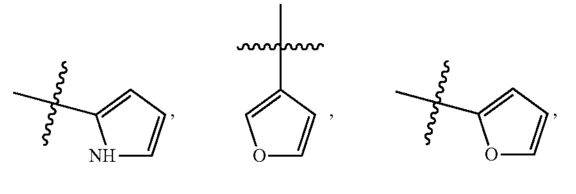

-continued

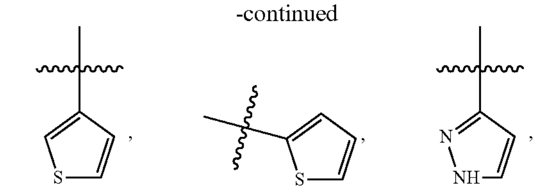

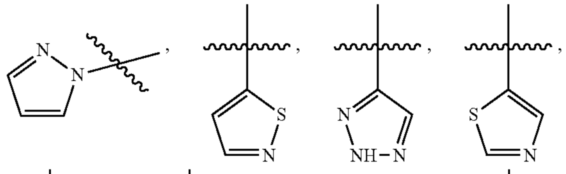

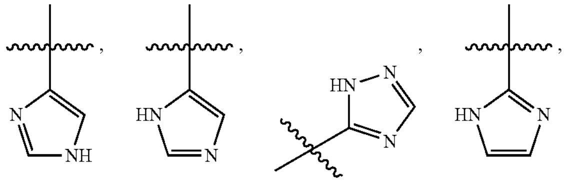

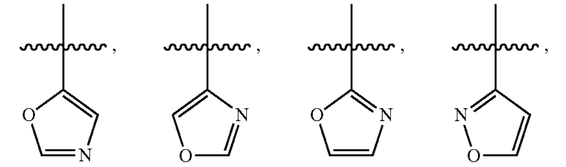

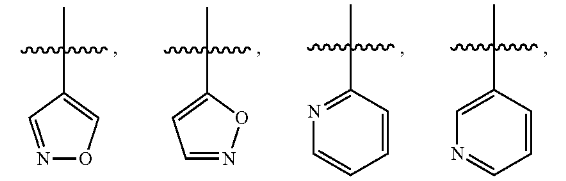

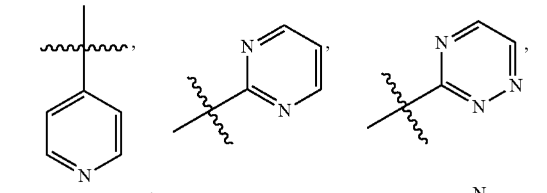

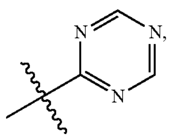

or

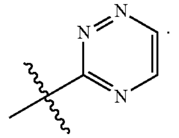

The above-mentioned five- to six-membered heteroaryl was unsubstituted or substituted with 1, 2 or 3 substituents each independently selected from the group consisting of halogen, cyano, hydroxyl, carboxyl, $C_{1-3}$ alkyl, $C_{1-3}$ alkoxy, $C_{2-4}$ alkenyl, $C_{2-4}$ alkynyl, halogenated $C_{1-3}$ alkyl, halogenated $C_{1-3}$ alkoxy, $NR_{a1}R_{b1}$, —$SO_2C_{1-3}$ alkyl, —$S(O)C_{1-3}$ alkyl, —$C(O)NR_{a1}R_{b1}$, —$C(O)OC_{1-3}$ alkyl, —$OC(O)C_{1-3}$ alkyl, $C_{3-6}$ cycloalkyl, $C_{3-6}$ cycloalkoxy, three- to six-membered heterocycloalkyl, phenyl, and five- to six-membered heteroaryl, wherein $R_{a1}$ and $R_{b1}$ were as defined above.

In some embodiments, in the respective formulas, the 8- to 10-membered heteroaryl described among the respective groups was selected from indolyl, isoindolyl, indazolyl, benzotriazolyl, benzothienyl, isobenzothienyl, benzofuranyl, benzoisofuranyl, benzimidazolyl, benzoxazolyl, benzisoxazolyl, benzoxadiazolyl, benzothiazolyl, benzisothiazolyl, benzothiadiazolyl, indanyl, purinyl, pyrido[3,2-d]pyrimidinyl, pyrido[2,3-d]pyrimidinyl, pyrido[3,4-d]pyrimidinyl, pyrido[4,3-d]pyrimidinyl, 1,8-naphthyridinyl, 1, -naphthyridinyl, 1,6-naphthyridinyl, 1,5-naphthyridinyl, pteridinyl, quinolinyl, isoquinolinyl, cinnolinyl, quinoxalinyl, phthalazinyl, or quinazolinyl.

In some embodiments, in the respective formulas, the three- to six-membered heterocycloalkyl group among the respective groups was a four- to six-membered heterocycloalkyl each independently selected from: azetidinyl, oxetanyl, tetrahydrofuranyl, tetrahydrothiophenyl, tetrahydropyrrolyl, oxazolidinyl, dioxolanyl, piperidinyl, piperazinyl, morpholinyl, dioxanyl, thiomorpholinyl, thiomorpholine-1,1-dioxide, tetrahydropyranyl, pyrrolidin-2-one group, dihydrofuran-2(3H)-one group, morpholin-3-one group, piperazin-2-one group, or piperidin-2-one group.

In some embodiments, the compound represented by formula (I) was any one of the following compounds:

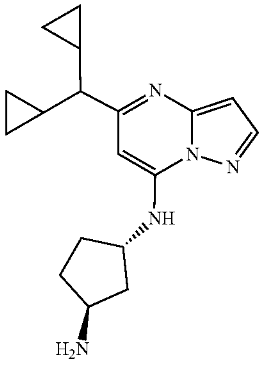

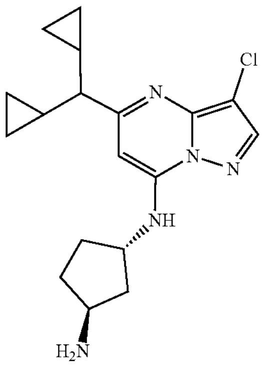

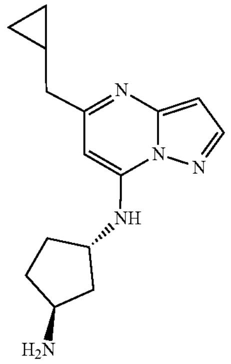

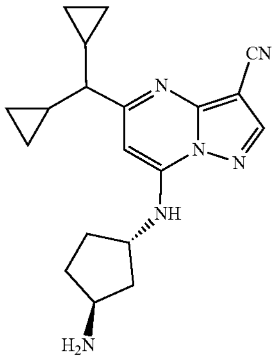

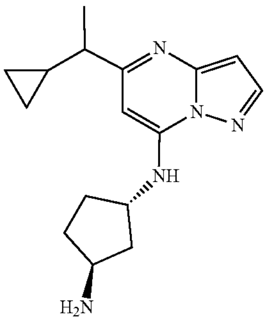

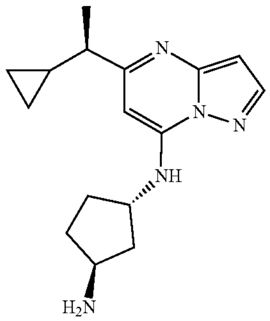

-continued

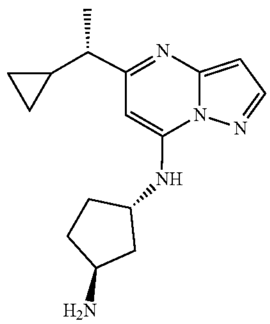

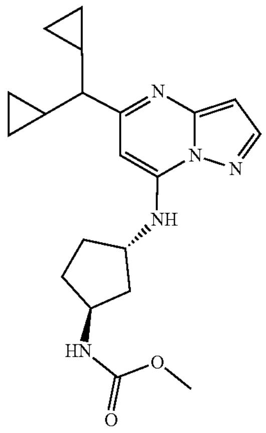

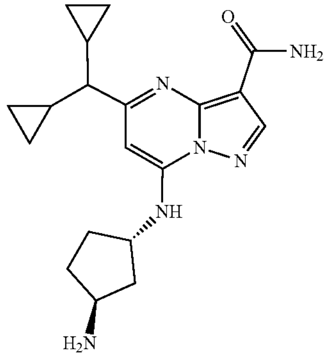

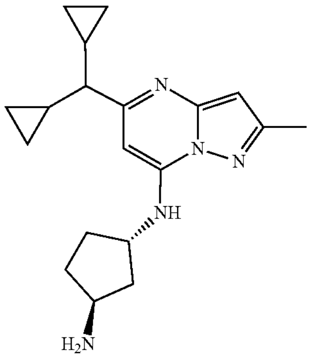

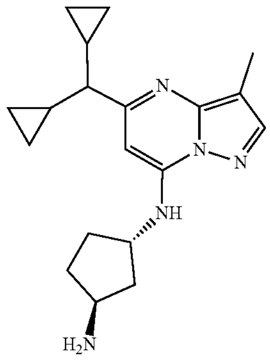

-continued
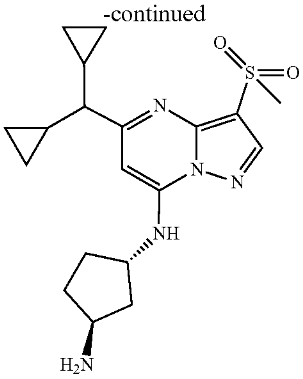
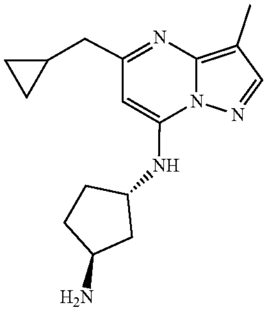
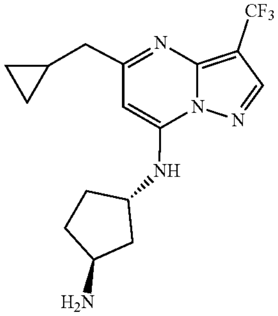
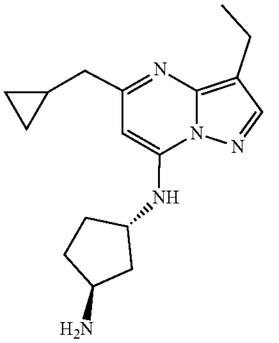
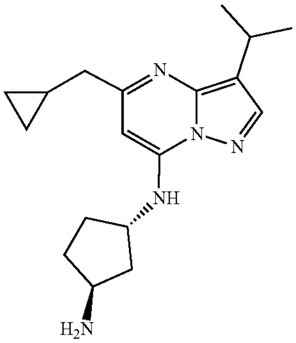
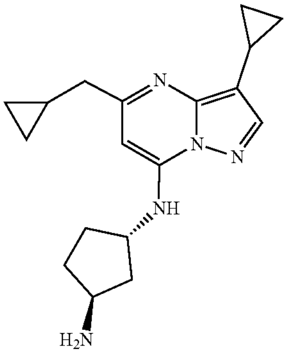
-continued
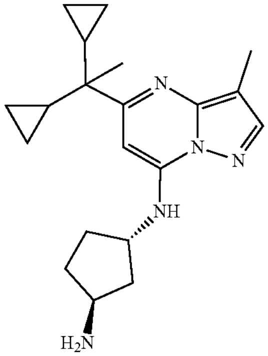
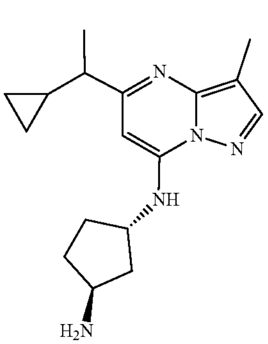
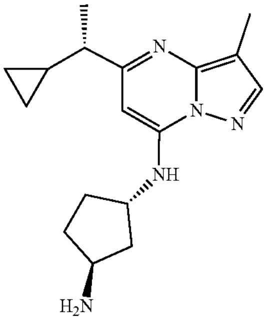
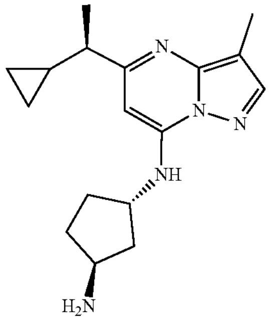
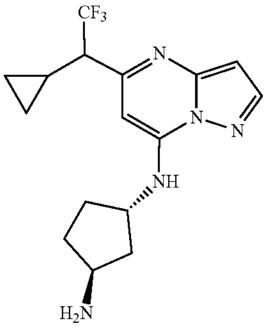
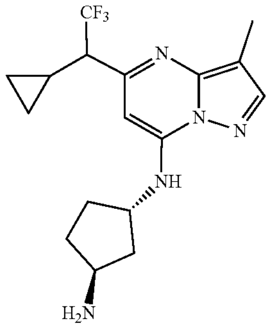
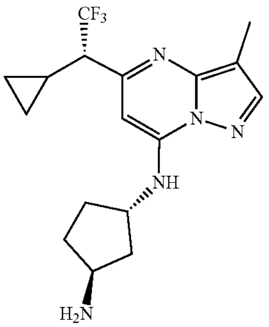
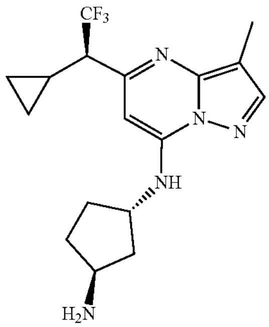
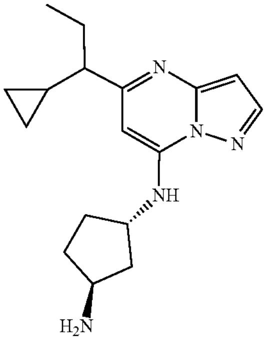
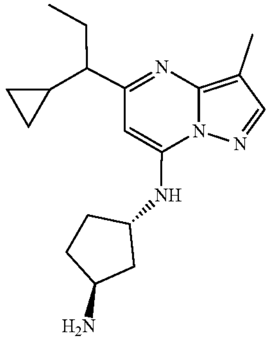

-continued
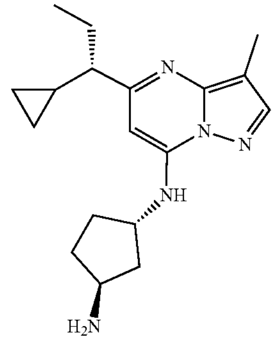
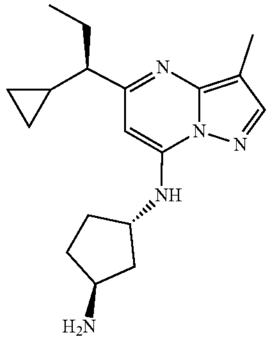
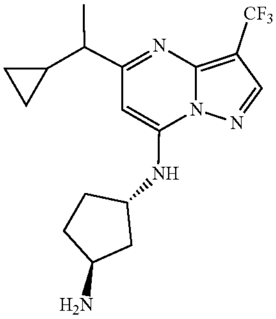
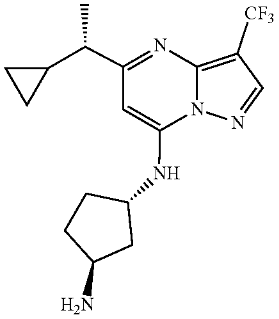
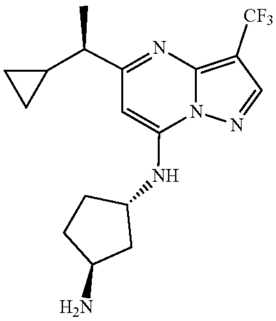
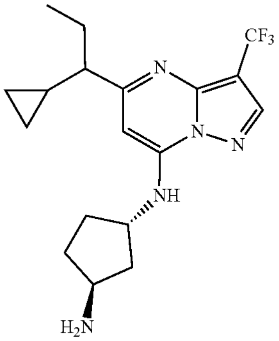
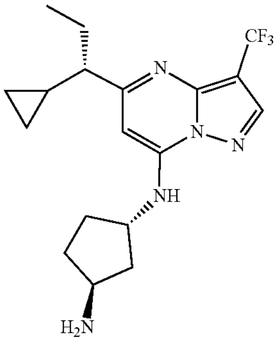
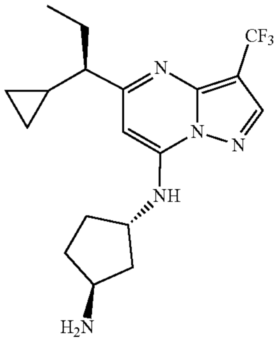
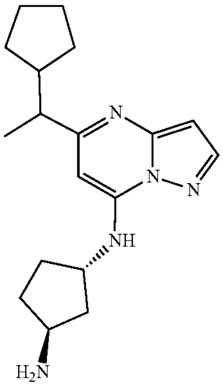
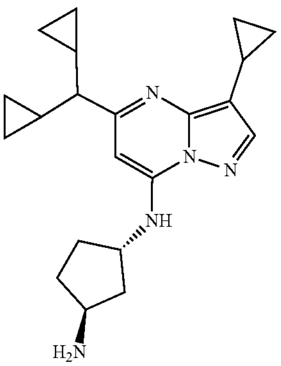
-continued
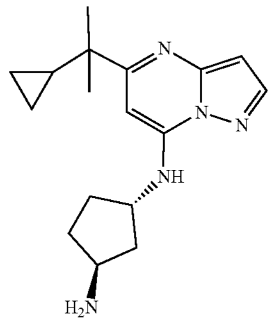
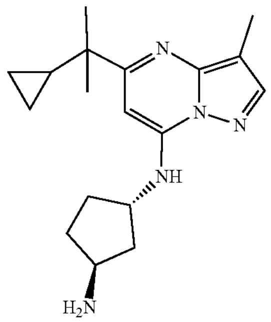
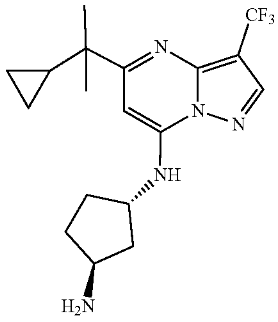
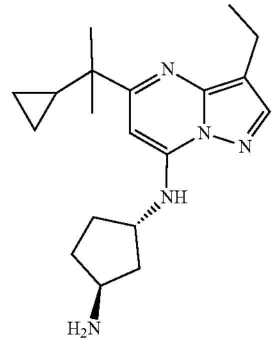
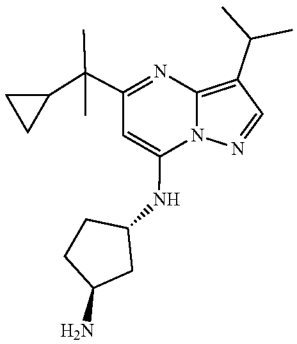
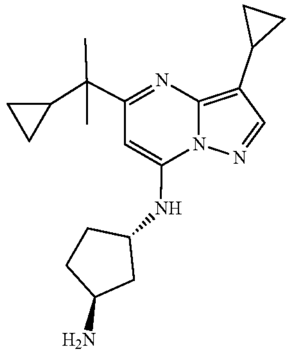
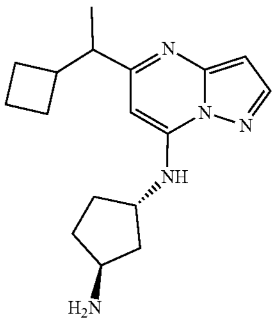
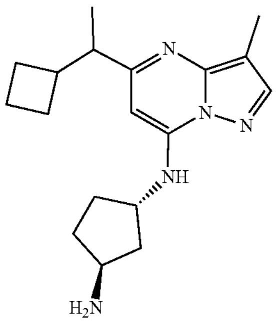

-continued
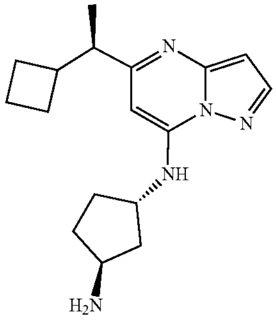
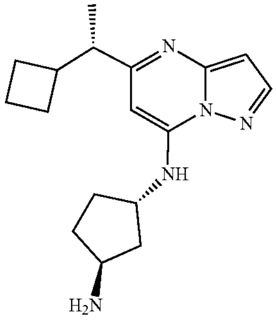
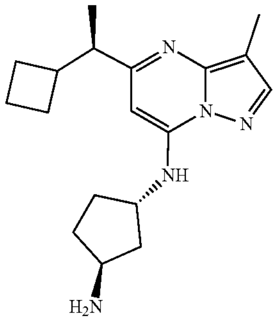
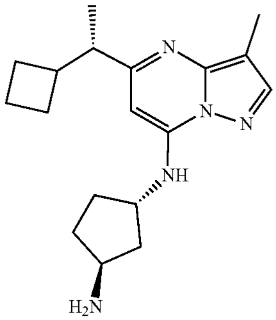
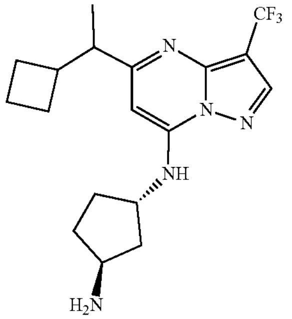
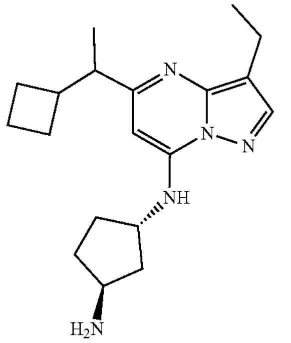
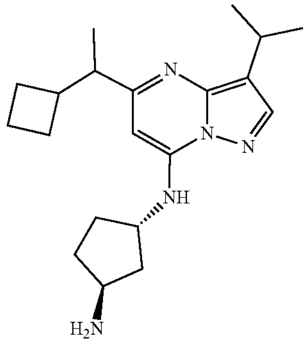
-continued
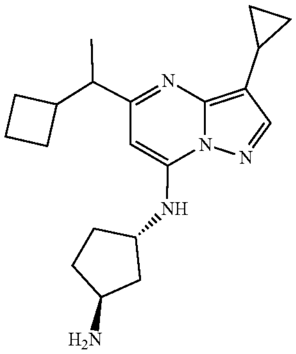
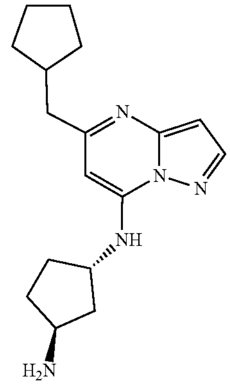
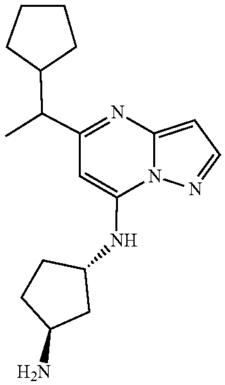
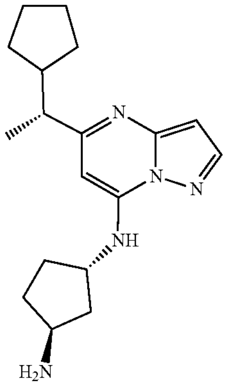
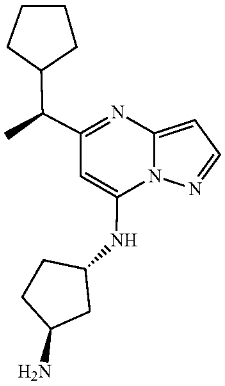
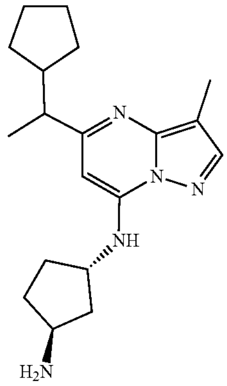
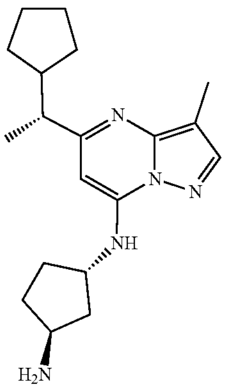
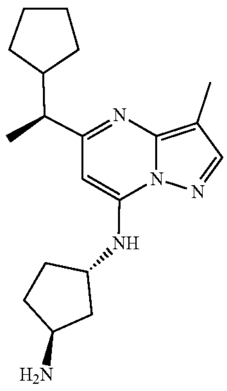

-continued
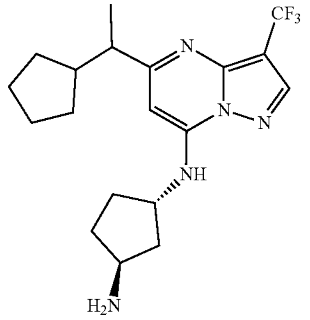
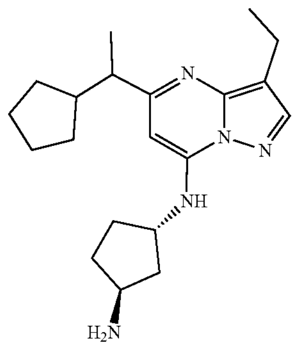
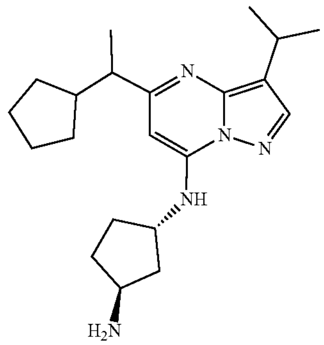
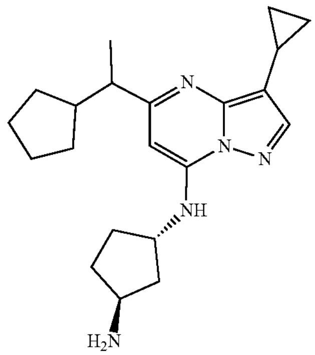
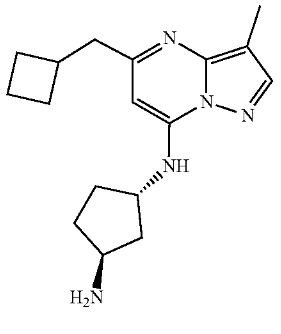
-continued
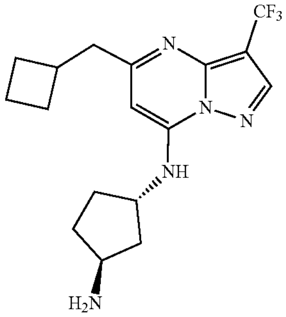
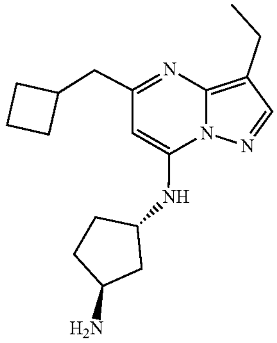
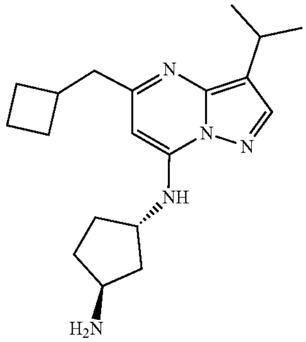
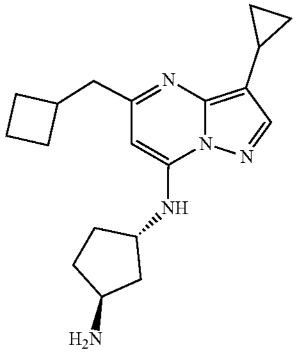
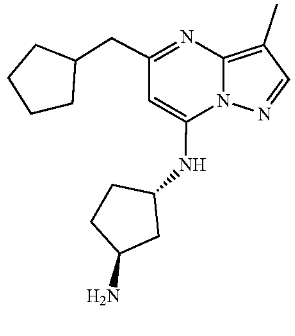

-continued
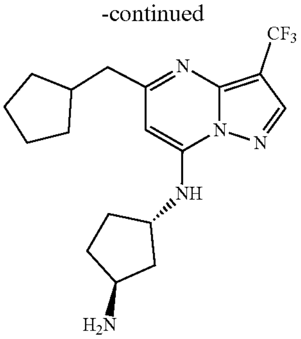
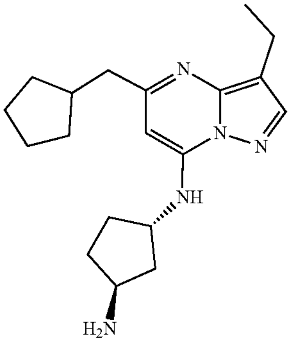
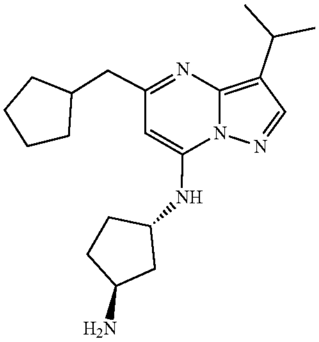
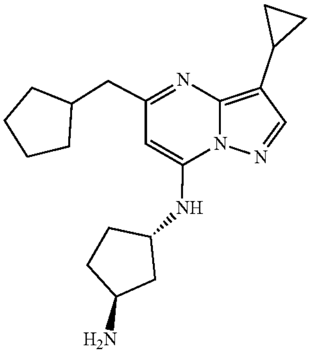
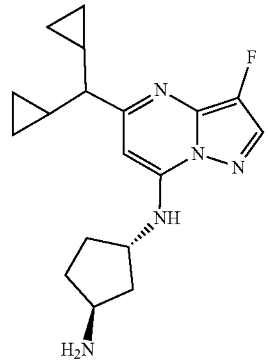
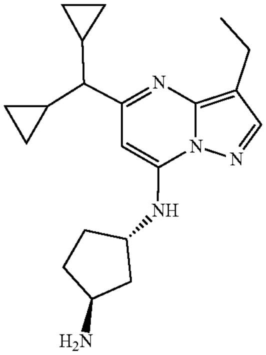
-continued
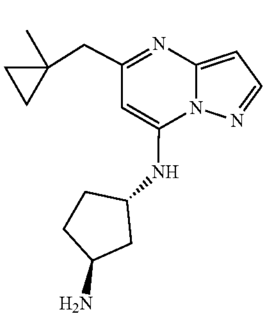
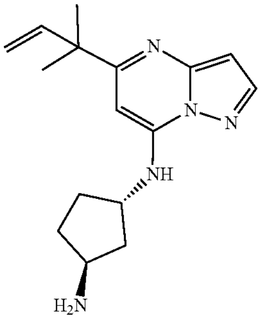
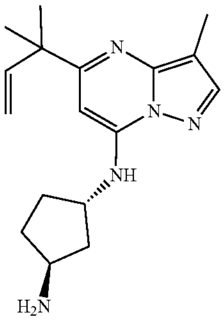
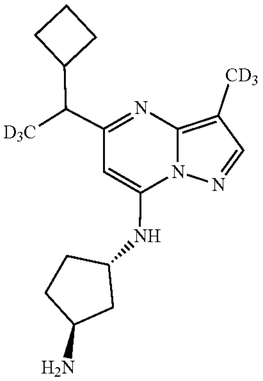
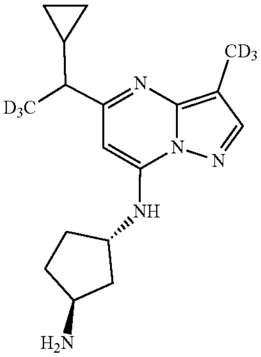
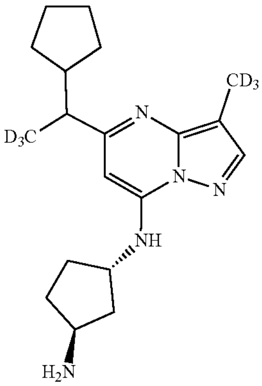
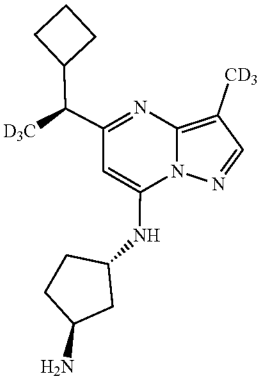
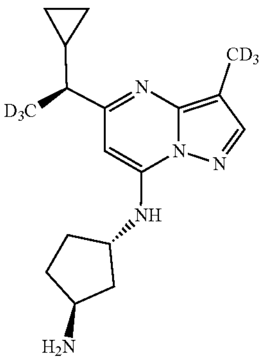

-continued
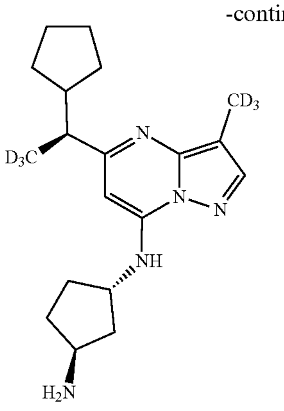
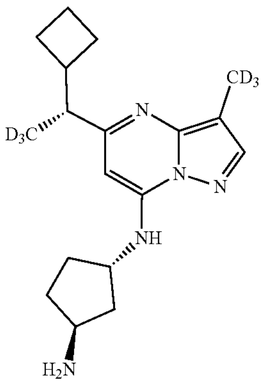
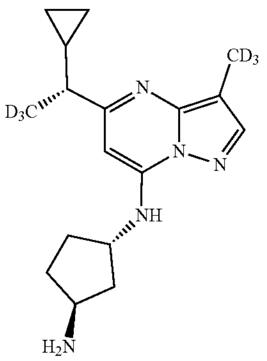
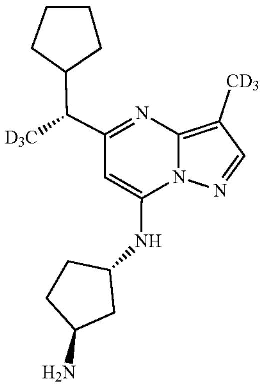
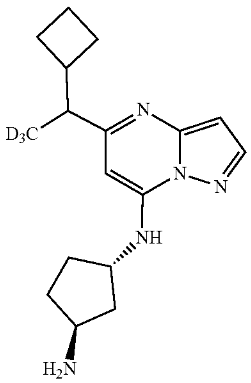
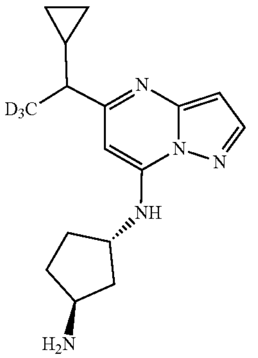
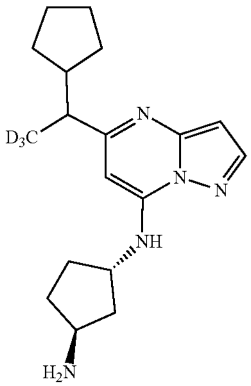
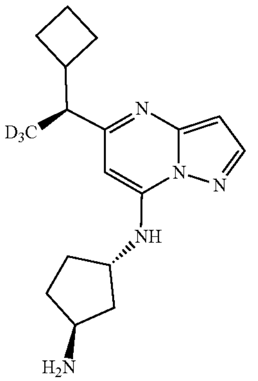
-continued
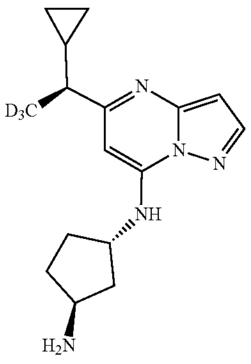
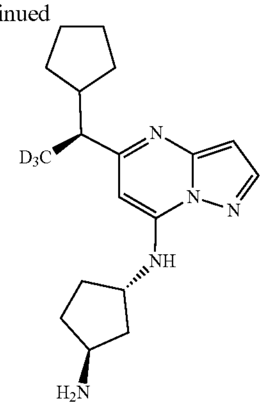
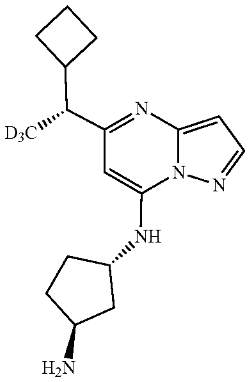
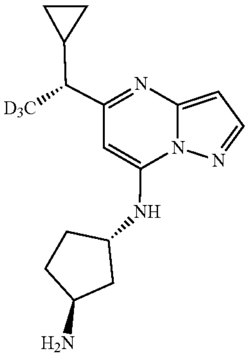
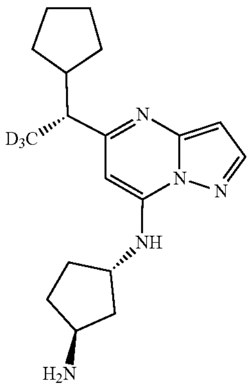
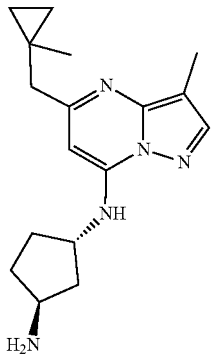
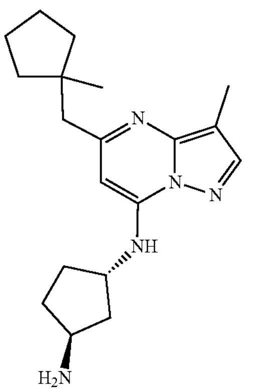
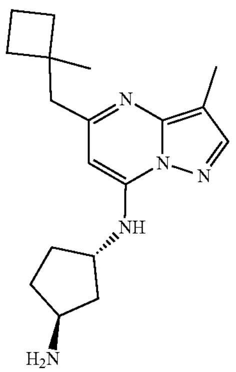

-continued

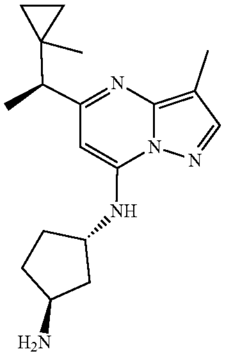

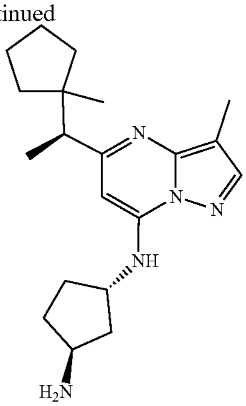

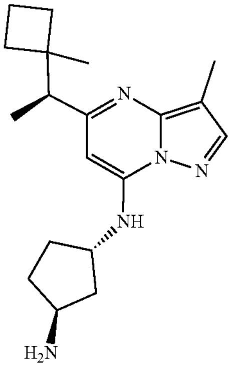

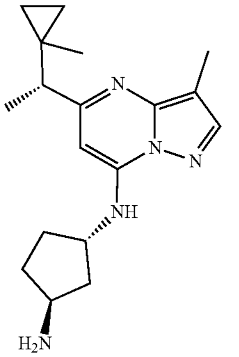

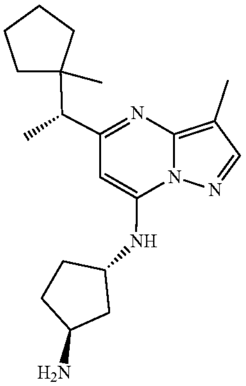

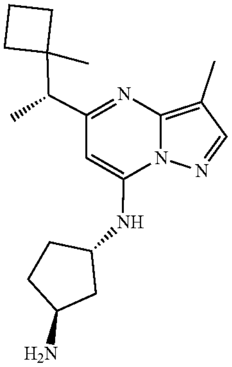

In some embodiments, the compound represented by formula (I) was any one of the compounds of the embodiments.

A second aspect of the disclosure provides a pharmaceutical composition. The pharmaceutical composition includes the compound, or the pharmaceutically acceptable salt thereof, or the stereoisomer thereof, or the solvate thereof, or the prodrug thereof according to the first aspect of the disclosure, and a pharmaceutically acceptable carrier.

A third aspect of the disclosure provides use of the compound, or the pharmaceutically acceptable salt thereof, or the stereoisomer thereof, or the solvate thereof, or the prodrug thereof according to the first aspect of the disclosure, and the pharmaceutical composition according to the second aspect of the disclosure, in the preparation of a medicament for treatment of a disease associated with or mediated by CDK9 activity. The disease was preferably a hyperproliferative disease, a virus-induced infectious disease, and/or a cardiovascular disease, and more preferably the hyperproliferative disease.

A fourth aspect of the present disclosure provides a method for treating a disease associated with or mediated by CDK9 activity. The method includes administering, to a subject, an effective amount of the compound, or the pharmaceutically acceptable salt thereof, or the stereoisomer thereof, or the solvate thereof, or the prodrug thereof according to the first aspect of the disclosure, or an effective amount of the pharmaceutical composition according to the second aspect of the present disclosure. In certain embodiments, the disease associated with CDK9 activity was a hyperproliferative disease, particularly cancer, such as solid tumors and hematological tumors.

In the present disclosure, the diseases associated with or mediated by CDK9 activity include diseases associated with or involving CDK9 activity (e.g., CDK9 overactivity), as well as conditions accompanying these diseases. The CDK9 overactivity refers to increased CDK9 enzymatic activity as compared to normal and non-diseased cells; or increased CDK9 activity leading to undesired cell proliferation, or decreased or insufficient programmed cell death (apoptosis); or mutations leading to constitutive activation of CDK9. The hyperproliferative diseases include diseases involving undesired or uncontrolled proliferation of cells, including the diseases involving reduced or insufficient programmed cell death (apoptosis). The compounds according to the present disclosure can be used to prevent, inhibit, block, reduce, lower, control, etc. cell proliferation and/or cell division, and/or produce apoptosis. The method includes administering, to a subject (including a mammal, including a human) in need thereof, a certain amount, which was effective to treat or prevent the diseases, of the compound, or the pharmaceutically acceptable salt, hydrate, or solvate thereof according to the present disclosure.

For example, the hyperproliferative diseases in the context of the present disclosure include, but were not limited to, angiogenesis or angioproliferative disorders, mesangial cell proliferative diseases, and solid tumors such as cancers of the breast, respiratory tract, brain, reproductive organs, digestive tract, urinary tract, eye, liver, skin, head and neck, thyroid, parathyroid, and their distant metastases. These diseases also include lymphomas, sarcomas, and leukemias. In some embodiments, the cancer was selected from pancreatic cancer, breast cancer, ovarian cancer, cervical cancer, or leukemia.

It was to be understood that, within the scope of the present disclosure, each of the above-described features of the disclosure and each of the features described in detail below (e.g., in the embodiments) may be combined with each other to form new or preferred embodiments, which was will not be described in detail herein for the limited space.

DETAILED DESCRIPTION

Figure 1:
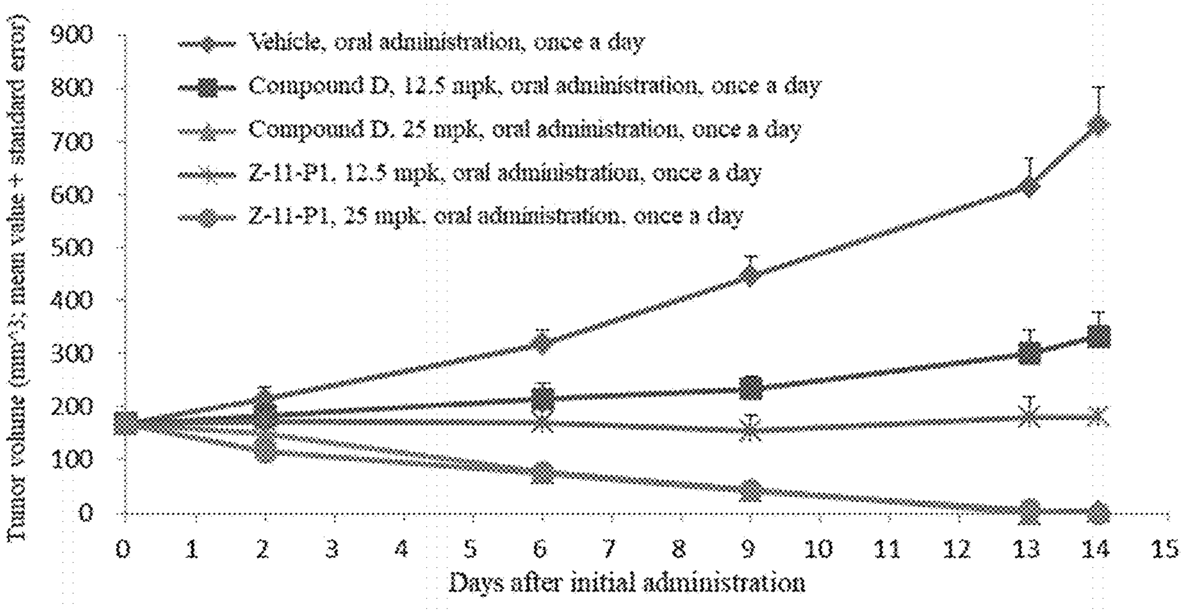
FIG. 1 was a graph depicting tumor volume change following once-daily oral administration of compound D and compound Z-11-PT.
Figure 2:
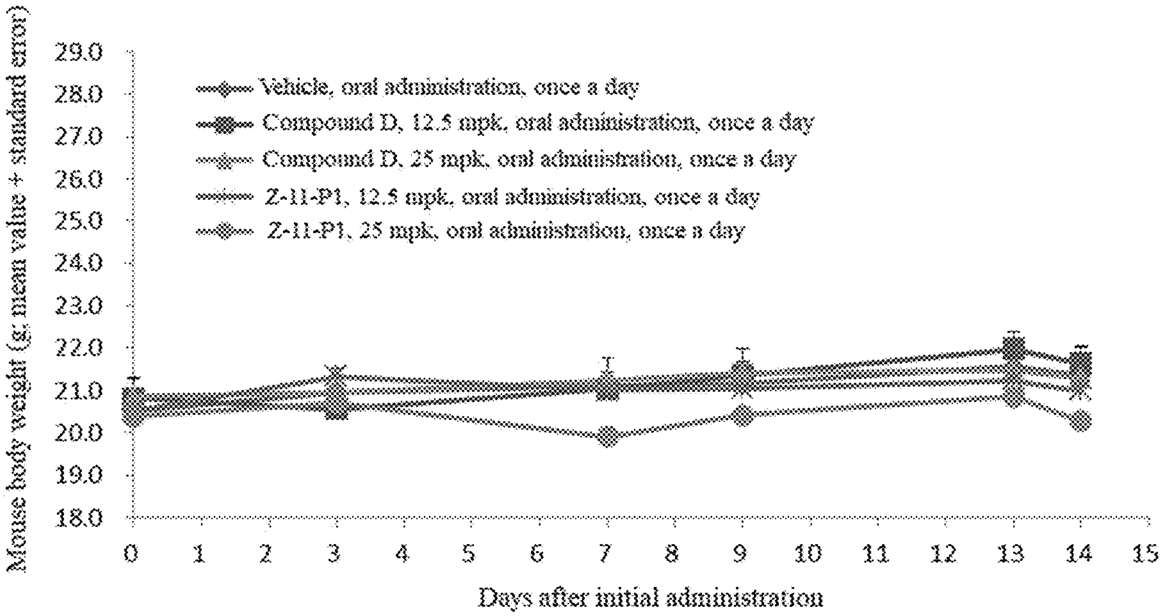
FIG. 2 was a graph of body weight change in mice following once-daily oral administration of compound D and compound Z-11-PT.
Figure 3:
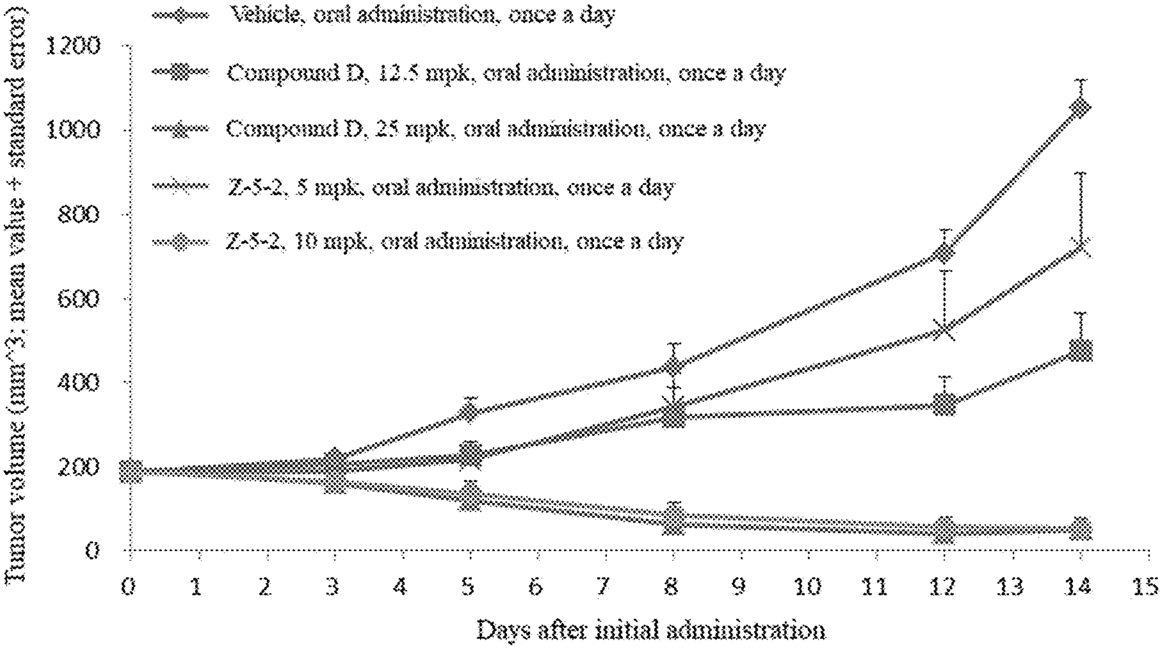
FIG. 3 was a graph depicting tumor volume change following once-daily oral administration of compound D and compound Z-5-2.
Figure 4:
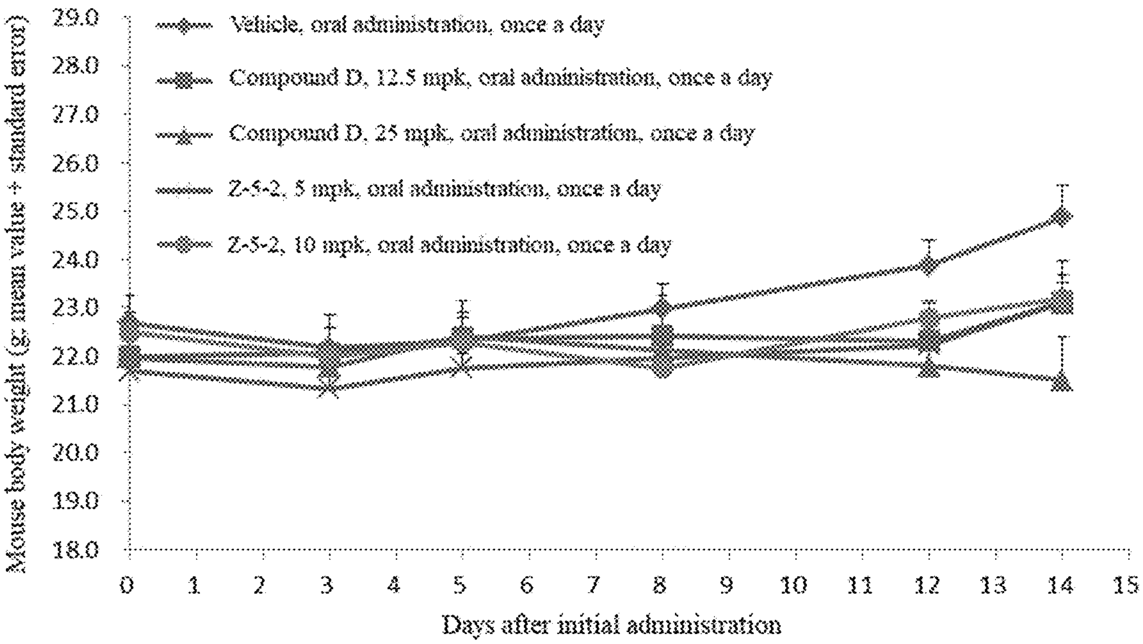
FIG. 4 was a graph of body weight change in mice following once-daily oral administration of compound D and compound Z-5-2.

Through extensive and intensive studies, the inventors have surprisingly found the substituted pyrazolo[1,5-a]pyrimidin-7-amine derivatives having significant CDK9 selective inhibitory activity and excellent in vivo pharmacokinetic activity. The series of compounds were therefore expected to be developed as medicaments for the treatment and/or prevention of the diseases associated with or mediated by CDK9 activity. The present disclosure was based on such facts.

Definition of Terms

In order that the technical contents of the present disclosure can be more clearly understood, the terms of the present disclosure were further described below.

"Alkyl" refers to straight or branched and saturated aliphatic hydrocarbon groups. "$C_{1-8}$ alkyl" refers to alkyl groups having 1 to 8 carbon atoms, preferably $C_{1-6}$ alkyl, and more preferably $C_{1-3}$ alkyl. Examples of alkyl groups include, but not limited to, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, etc.

"Alkenyl" refers to straight or branched unsaturated aliphatic hydrocarbon groups having one or more carbon-carbon double bonds (C═C). "$C_{2-8}$ alkenyl" refers to alkenyl groups having 2 to 8 carbon atoms, preferably $C_{2-6}$ alkenyl, and more preferably $C_{2-4}$ alkenyl, similarly defined. Examples of alkenyl include, but not limited to, ethenyl, propenyl, isopropenyl, n-butenyl, isobutenyl, pentenyl, hexenyl, etc.

"Alkynyl" refers to straight and branched unsaturated aliphatic hydrocarbon groups having one or more carbon-carbon triple bonds. "$C_{2-8}$ alkynyl" refers to alkynyl groups having 2 to 8 carbon atoms, preferably $C_{2-6}$ alkynyl, and more preferably $C_{2-4}$ alkynyl, similarly defined. Examples of alkynyl include, but not limited to, ethynyl, propynyl, n-butynyl, iso-butynyl, pentynyl, hexynyl, etc.

"Cycloalkyl" and "cycloalkyl ring", which may be used interchangeably, both refer to saturated monocyclic, bicyclic, or polycyclic cyclic hydrocarbon groups, or groups fused to an aryl or heteroaryl group, or an optionally substituted form thereof. In certain embodiments, the cycloalkyl ring contains one or more carbonyl, e.g., oxo-substituted groups. "$C_{3-8}$ cycloalkyl" refers to monocyclic cycloalkyl groups having 3 to 8 carbon atoms. Examples of cycloalkyl include, but not limited to, cyclopropyl, cyclobutyl, cyclopentyl, cyclohexyl, cycloheptyl, cyclooctyl, cyclobutanone, cyclopentanone, cyclopentane-1,3-dione, etc. Preferred were $C_{3-6}$ cycloalkyl groups, including cyclopropyl, cyclobutyl, cyclopentyl, and cyclohexyl. "$C_{8-10}$ cycloalkyl" refers to fused bicyclic hydrocarbon groups having 8 to 10 ring atoms. Examples of $C_{8-10}$ cycloalkyl include, but not limited to

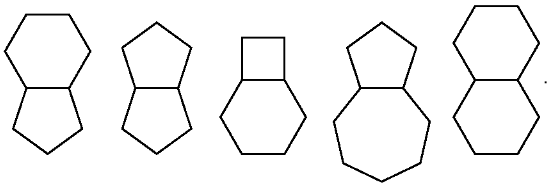

"Spirocyclyl" and "spirocycle" may be used interchangeably and refer to polycyclic cyclic hydrocarbon groups having one carbon atom (referred to as a spiro atom) shared by single rings. A "seven- to eleven-membered spirocyclyl" refers to a spirocycle having 7 to 11 ring atoms. The spirocyclic rings can be divided into double or multiple spiro rings, preferably double spiro rings, depending on the number of rings. More preferred were four-membered/five-membered double spiro rings, five-membered/five-membered double spiro rings, or five-membered/six-membered double spiro rings. For example,

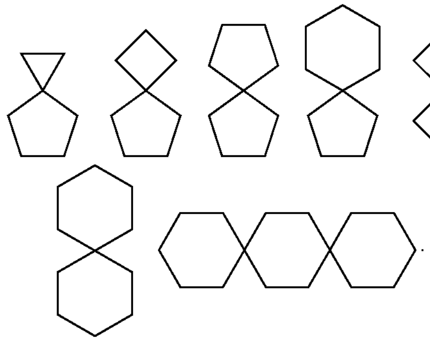

"Cycloalkenyl" and "cycloalkenyl ring", which may be used interchangeably, both refer to monocyclic, bicyclic or polycyclic cyclic hydrocarbon groups containing one or more carbon-carbon double bonds within the ring. These groups may be fused to an aryl or heteroaryl group. A cycloalkenyl ring may be optionally substituted. In certain embodiments, the cycloalkenyl ring contains one or more carbonyl, e.g., oxo-substituted groups. "$C_{3-8}$ cycloalkenyl" refers to monocyclic cycloalkenyl groups having 3 to 8 carbon atoms. Preferred were $C_{3-6}$ cycloalkenyl. Examples of cycloalkenyl include, but not limited to, cyclobutenyl, cyclopentenyl, cyclohexenyl, cyclohexadienyl, cycloheptatrienyl, cyclopentyl-2-en-1-one, cyclohexyl-2,5-dien-1-one, cyclohexyl-2-en-1-one, and cyclohex-2-ene-1,4-dione, etc.

"Heterocycloalkyl" and "heterocycloalkyl ring", which may be used interchangeably, both refer to cycloalkyl groups containing at least one heteroatom such as nitrogen, oxygen and sulfur on a ring atom. These group may be fused to an aryl or heteroaryl group. The heterocycloalkyl ring may be optionally substituted. In certain embodiments, the heterocycloalkyl ring contains one or more carbonyl or thiocarbonyl groups, such as oxo- and thioxo-containing groups. A "three- to eight-membered heterocycloalkyl" refers to a monocyclic cyclic hydrocarbon group having 3 to 8 ring atoms, one, two, or three of which were heteroatoms selected from nitrogen, oxygen and sulfur. Preferred were four- to eight-membered heterocycloalkyl groups. More preferred were three- to six-membered heterocycloalkyl groups having 3 to 6 ring atoms, one or two ring atoms of which were heteroatoms selected from nitrogen, oxygen, and sulfur. More preferred were four- to six-membered heterocycloalkyl groups having 4 to 6 ring, one or two of which were heteroatoms selected from nitrogen, oxygen, and sulfur. Non-limiting examples include aziridinyl, oxiranyl, azetidinyl, oxetanyl, tetrahydrofuranyl, tetrahydrothiophenyl, tetrahydropyrrolyl, oxazolidinyl, dioxolanyl, piperidinyl, piperazinyl, morpholinyl, dioxanyl, thiomorpholinyl, thiomorpholine-1,1-dioxide, tetrahydropyranyl, azetidin-2-one group, oxetan-2-one group, dihydrofuran-2(3H)-one group, pyrrolidin-2-one group, pyrrolidin-2,5-dionyl, dihydrofuran-2,5-dionyl, piperidin-2-one group, tetrahydro-2H-pyran-2-one group, piperazin-2-one group, and morpholin-3-one group, etc. “Six- to twelve-membered heterocycloalkyl” and “six- to twelve-membered fused heterocycloalkyl”, which may be used interchangeably, both refer to fused bicyclic hydrocarbon groups having 6 to 12 ring atoms, one, two or three ring atoms of which were heteroatoms selected from nitrogen, oxygen, and sulfur. “Eight- to ten-membered heterocycloalkyl” and “eight- to ten-membered fused heterocycloalkyl”, which may be used interchangeably, both refer to fused bicyclic hydrocarbon group having 8 to 10 ring atoms, one, two or three ring atoms of which were heteroatoms selected from nitrogen, oxygen, and sulfur. Non-limiting examples include hexahydro-1H-furo[3,4-c]pyrrole, octahydro-1H-cyclopenta[c]pyridine, hexahydro-1H-pyrrolo[2,1-c][1,4]oxazine, octahydropyrrolo[1,2-a]pyrazine, hexahydropyrrolo[1,2-a]pyrazin-4(1H)-one, and octahydrocyclopenta[H]pyrrole, etc. In fused bicyclic heterocycloalkyl groups containing one or more nitrogen atoms, the linking site may be at a carbon or nitrogen atom, as valency permits. Bicyclic heterocycloalkyl systems may include one or more heteroatoms in one or both rings.

“Heterospiro ring group” and “heterospiro ring”, which may be used interchangeably, both refer to a monovalent non-aromatic ring system with two single rings sharing one carbon atom, consisting of carbon atoms and heteroatoms selected from nitrogen, oxygen, sulfur and phosphorus, containing no unsaturation, and being linked to the parent core by a single bond. The heterospiro ring may be optionally substituted. In certain embodiments, the heterospiro ring contains one or more carbonyl or thiocarbonyl groups, such as oxo- and thioxo-containing groups. “seven- to eleven-membered heterospirocyclyl” refers to a heterospirocyclyl group having 7 to 11 ring atoms, one, two or three ring atoms of which were heteroatoms. Non-limiting examples of heterospirocyclyl groups include 2,6-diazaspiro[3.4]octan-5-one group, 2-oxo-6-azaspiro[3.3]heptanyl, 6-oxaspiro[3.3]heptan-2-yl, 7-methyl-7-azaspiro[3.5]nonan-2-yl, 7-methyl-2,7-diazaspiro[3.5]nonan-2-yl, and 9-methyl-9-phosphaspiro[5.5]undecan-3-yl, etc.

“Heterocyclenyl” and “heterocycloalkenyl ring”, which may be used interchangeably, both refer to heterocycloalkyl groups containing one or more carbon-carbon double bonds or carbon-nitrogen double bonds in the ring backbone, but not intended to include heteroaryl moieties as defined herein. The group may be fused to an aryl or heteroaryl group. A heterocycloalkenyl ring may be optionally substituted. In certain embodiments, the heterocycloalkenyl ring contains one or more carbonyl or thiocarbonyl groups, such as oxo- and thioxo-containing groups. “Five- to eight-membered heterocycloalkenyl ring” refers to a heterocycloalkenyl ring having 5 to 8 ring atoms, in which 1, 2, or 3 ring atoms were heteroatoms selected from nitrogen, oxygen, and sulfur. Preferred were five- to six-membered heterocycloalkenyl rings. Non-limiting examples of heterocycloalkenyl rings include a 4,5-dihydro-1H-imidazole ring, a 1,4,5,6-tetrahydropyrimidine ring, a 3,4,7,8-tetrahydro-2H-1,4,6-oxadiazoxazine ring, a 1,6-dihydropyrimidine ring, a 4,5,6,7-tetrahydro-1H-1,3-diazepine ring, and a 2,5,6,7-tetrahydro-1,3,5-oxadiazepine ring.

“Aryl” and “aryl ring”, which may be used interchangeably, both refer to an all-carbon monocyclic or fused polycyclic (i.e., rings sharing a pair of adjacent carbon atoms) group having a conjugated 7-electron system, which may be fused to a cycloalkyl, heterocycloalkyl, cycloalkenyl, heterocycloalkenyl or heteroaryl ring. “$C_{6-10}$ aryl” refers to monocyclic or bicyclic aryl groups having 6 to 10 carbon atoms. Examples of aryl include, but not limited to, phenyl, naphthyl, etc.

“Heteroaryl” and “heteroaryl ring”, which may be used interchangeably, both refer to a monocyclic, bicyclic, or polycyclic 4n+2 aromatic ring system (e.g., having 6 or 10 $\pi$ electrons shared and arranged in a cyclic arrangement) having ring carbon atoms and ring heteroatoms, where each heteroatom was independently selected from nitrogen, oxygen, and sulfur. In the present disclosure, heteroaryl also includes ring systems, in which the above-mentioned heteroaryl rings were fused with one or more cycloalkyl, heterocycloalkyl, cycloalkenyl, heterocycloalkenyl or aryl rings. The heteroaryl ring may be optionally substituted. “Five- to ten-membered heteroaryl” refers to a monocyclic or bicyclic heteroaryl having 5 to 10 ring atoms, one, two, three or four ring atoms of which were heteroatoms. “Five to six-membered heteroaryl” refers to a monocyclic heteroaryl having 5 to 6 ring atoms, one, two, three or four ring atoms of which were heteroatom, and non-limiting examples thereof include thienyl, furanyl, thiazolyl, isothiazolyl, imidazolyl, oxazolyl, pyrrolyl, pyrazolyl, triazolyl, 1,2,3-triazolyl, 1,2,4-triazolyl, 1,2,5-triazolyl, 1,3,4-triazolyl, tetrazolyl, isoxazolyl, oxadiazolyl, 1,2,3-oxadiazolyl, 1,2,4-oxadiazolyl, 1,2,5-oxadiazolyl, 1,3,4-oxadiazolyl, thiadiazolyl, pyridinyl, pyridazinyl, pyrimidinyl, pyrazinyl, triazinyl, and tetrazinyl. “Eight- to ten-membered heteroaryl” refers to a bicyclic heteroaryl group having 8 to 10 ring atoms, one, two, three or four ring atoms of which were heteroatoms, and non-limiting examples thereof include indolyl, isoindolyl, indazolyl, benzotriazolyl, benzothienyl, isobenzothienyl, benzofuranyl, benzoisofuranyl, benzimidazolyl, benzoxazolyl, benzisoxazolyl, benzoxadiazolyl, benzothiazolyl, benzisothiazolyl, benzothiadiazolyl, indoxazinyl, purinyl, pyrido[3,2-d]pyrimidinyl, pyrido[2,3-d]pyrimidinyl, pyrido[3,4-d]pyrimidinyl, pyrido[4,3-d]pyrimidinyl, 1,8-naphthyridinyl, 1,7-naphthyridinyl, 1,6-naphthyridinyl, 1,5-naphthyridinyl, pteridinyl, quinolinyl, isoquinolinyl, cinnolinyl, quinoxalinyl, phthalazinyl and quinazolinyl. “Heteroatom” means nitrogen, oxygen, or sulfur. In heteroaryl groups containing one or more nitrogen atoms, the linking site may be a carbon or nitrogen atom, as valency permits. Heteroaryl bicyclic ring systems may include one or more heteroatoms in one or both rings.

“Fused” refers to a structure in which two or more rings share one or more bonds.

“Phenyl-heterocycloalkyl” refers to a bicyclic, tricyclic or polycyclic ring system formed by fusing a benzene ring to a heterocycloalkyl ring, wherein the heterocycloalkyl ring was as defined above. “Seven- to eleven-membered phenyl-heterocycloalkyl” refers to a bicyclic group having 7 to 11 ring atoms, one, two, three or four ring atoms of which were heteroatoms selected from nitrogen, oxygen and sulfur. Preferred were eight- to ten-membered phenyl heterocycloalkyl groups having 8 to 10 ring atoms, one, two or three ring atoms of which were heteroatoms selected from nitrogen, oxygen and sulfur. Non-limiting examples include indoline, benzo[d][1,3]dioxazole, 1,2,3,4-tetrahydroisoquinoline, or 3,4-dihydro-2H-benzo[b][1,4]oxazine, etc.

"Heteroaryl-heterocycloalkyl" refers to a bicyclic, tricyclic or polycyclic ring system formed by fusing a heteroaryl ring a heterocycloalkyl ring, wherein heterocycloalkyl ring was as defined above. "Seven- to eleven-membered heteroaryl-heterocycloalkyl" refers to a bicyclic group having 7 to 11 ring atoms, one, two, three or four ring atoms of which were heteroatoms selected from nitrogen, oxygen and sulfur. Preferred were eight- to ten-membered heteroaryl-heterocycloalkyl groups having 8 to 10 ring atoms, one, two or three ring atoms of which were heteroatoms selected from nitrogen, oxygen and sulfur. Non-limiting examples include 2,3-dihydro-1H-pyrrolo[2,3-b]pyridine,[1,3]dioxolo[4,5-b]pyridine, 2,3-dihydro-1H-pyrido[3,4-b][1,4]oxazine, 2,3,4,6-tetrahydropyrrolo[3,4-b][1,4]oxazine, or 2,4,5,6-tetrahydropyrano[2,3-c]pyrazole, 5,6,7,8-tetrahydropyrido[3,4-d]pyrimidine, etc.

"Alkoxy" means an —O-alkyl group, in which the alkyl group was as described above. $C_{1-8}$ alkoxy was preferred, $C_{1-6}$ alkoxy was more preferred, and $C_{1-3}$ alkoxy was most preferred. Non-limiting examples of alkoxy include methoxy, ethoxy, n-propoxy, isopropoxy, butoxy, t-butoxy, isobutoxy, and pentoxy, etc.

"Cycloalkoxy" means an —O— cycloalkyl group in which the cycloalkyl group was as described above. $C_{3-8}$ cycloalkoxy was preferred, and $C_{3-6}$ cycloalkoxy was more preferred. Non-limiting examples of cycloalkoxy include cyclopropyloxy, cyclobutyloxy, cyclopentyloxy, and cyclohexyloxy, etc.

"A bond" refers to two groups connected by a covalent bond.

"Halogen" refers to fluorine, chlorine, bromine, or iodine.

"Halogenated" refers to a group in which one or more (e.g., 1, 2, 3, 4, or 5) hydrogens were substituted with a halogen.

For example, "halogenated alkyl" refers to an alkyl group substituted with one or more (e.g., 1, 2, 3, 4, or 5) halogens, where alkyl was as defined above. Halogenated $C_{1-8}$ alkyl was preferred, halogenated $C_{1-6}$ alkyl was more preferred, and halogenated $C_{1-3}$ alkyl was most preferred. Examples of halogenated alkyl include, but were not limited to, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, and trifluoroethyl, etc.

As another example, "halogenated alkoxy" refers to an alkoxy group substituted with one or more (e.g., 1, 2, 3, 4, or 5) halogens, where alkoxy was as defined above. Halogenated $C_{1-8}$ alkoxy was preferred, halogenated $C_{1-6}$ alkoxy was more preferred, and halogenated $C_{1-3}$ alkoxy was most preferred. Examples of halogenated alkoxy includes, but not limited to, trifluoromethoxy, trifluoroethoxy, monofluoromethoxy, monofluoroethoxy, difluoromethoxy, and difluoroethoxy, etc.

As another example, "halogenated cycloalkyl" refers to cycloalkyl substituted with one or more (e.g., 1, 2, 3, 4, or 5) halogens, where cycloalkyl was as defined above. Halogenated $C_{3-8}$ cycloalkyl was preferred, and halogenated and $C_{3-6}$ cycloalkyl was more preferred. Examples of halogenated cycloalkyl groups include, but not limited to, trifluorocyclopropyl, monofluorocyclopropyl, monofluorocyclohexyl, difluorocyclopropyl, and difluorocyclohexyl, etc.

"Deuteroalkyl" refers to alkyl groups substituted with one or more (e.g., 1, 2, 3, 4, or 5) deuterium atoms, where alkyl was as defined above. Deuterated $C_{1-8}$ alkyl was preferred, deuterated $C_{1-6}$ alkyl was more preferred, and deuterated $C_{1-3}$ alkyl was most preferred. Examples of deuterated alkyl groups include, but were not limited to, monodeuteromethyl, monodeuteroethyl, dideuteromethyl, dideuteroethyl, trideuteromethyl, and trideuterioethyl, etc.

"Amino" refers to $NH_2$, "cyano" refers to CN, "nitro" refers to $NO_2$, "benzyl" refers to $—CH_2$-phenyl, "oxo" refers to =O, "carboxyl" refers to —C(O)OH, "acetyl" refers to $—C(O)CH_3$, "hydroxymethyl" refers to $—CH_2OH$, "hydroxyethyl" refers to $—CH_2CH_2OH$ or $—CHOHCH_3$, "hydroxy" refers to —OH, "thiol" refers to SH, and "cyclopropylidene" refer to a structure of

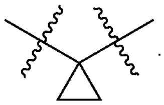 [SMILES: *C1(*)CC1].

"Saturated or partially unsaturated monocyclic" refers to an all-carbon monocyclic ring system that was saturated or partially unsaturated, wherein "partially unsaturated" refers to that a ring moiety includes at least one double or triple bond, and "partially unsaturated" was intended to encompass rings having multiple sites of unsaturation, but was not intended to include aryl or heteroaryl moieties as defined herein. In certain embodiments, a saturated or partially unsaturated monocyclic ring contains one or more carbonyl, e.g., oxo-substituted groups. The "three- to seven-membered saturated or partially unsaturated monocyclic ring" has 3 to 7 ring carbon atoms, preferably a saturated or partially unsaturated monocyclic ring having 3 to 6 ring carbon atoms, more preferably a saturated monocyclic ring having 3 to 6 ring carbon atoms. Non-limiting examples of saturated or partially unsaturated monocyclic rings include cyclopropyl rings, cyclobutyl rings, cyclopentyl rings, cyclopentenyl rings, cyclohexyl rings, cyclohexenyl rings, cyclohexadienyl rings, cycloheptyl rings, cycloheptatrienyl rings, cyclopentanone rings, cyclopentane-1,3-dione rings, and the like.

"Saturated or partially unsaturated monoheterocyclic ring" refers to a saturated or partially unsaturated monocyclic ring in which 1, 2 or 3 ring carbon atoms were replaced by a heteroatom selected from nitrogen, oxygen, or $S(O)_t$ (where t was an integer from 0 to 2), excluding the ring portion of —O—O—, —O—S— or —S—S—, the remaining ring atoms being carbon. The "three- to seven-membered saturated or partially unsaturated monoheterocyclic ring" has 3 to 7 ring atoms of which 1, 2 or 3 were heteroatoms as described above. Preferred was the three to six-membered saturated or partially unsaturated monoheterocyclic ring having 3 to 6 ring, one or two of which were the aforementioned heteroatoms was preferred, and more preferred was five- to six-membered saturated or partially unsaturated monoheterocyclic ring having 5 to 6 ring, one or two of which were the aforementioned heteroatoms, and most preferred was a 5- or 6-membered saturated monoheterocyclic ring. Non-limiting examples of saturated monoheterocyclic rings include a propylene oxide ring, an azetidine ring, an oxetane ring, a tetrahydrofuran ring, a tetrahydrothiophene ring, a tetrahydropyrrole ring, a piperidine ring, a pyrroline ring, an oxazolidine ring, a piperazine ring, a dioxolane ring, dioxane, a morpholine ring, a thiomorpholine ring, a thiomorpholine-1,1-dioxide, a tetrahydropyran ring, an azetidin-2-one ring, an oxetan-2-one ring, a pyrrolidin-2-one ring, a pyrrolidin-2,5-dione ring, a piperidin-2-one ring, a dihydrofuran-2(3H)-one ring, a dihydrofuran-2,5-diketone ring, a tetrahydro-2H-pyran-2-one ring, piperazin-2-one ring, and a morpholin-3-one ring. Non-limiting examples of partially unsaturated monoheterocyclic rings include a 1,2-dihydroazetidinium ring, a 1,2-dihydroxydioxacyclobutadiene ring, a 2,5-dihydro-1H-pyrrole ring, 2,5-dihydrofuran ring, a 2,3-dihydrofuran ring, a 2,3-dihydro-1H-pyrrole ring, a 3,4-dihydro-2H-pyran ring, a 1,2,3,4-tetrahydropyridine ring, a 3,6-dihydro-2H-pyran ring, a 1,2,3,6-tetrahydropyridine ring, a 4,5-dihydro-1H-imidazole ring, a 1,4,5,6-tetrahydropyrimidine ring, a 3,4,7,8-tetrahydro-2H-1,4,6-oxadiazoxazine ring, a 1,6-dihydropyrimidine ring, and a 4,5,6,7-tetrahydro-1H-1,3-diazepine ring, 2,5,6,7-tetrahydro-1,3,5-oxadiazepine ring.

"Substituted" refers to groups in which one or more hydrogen atoms, preferably 1 to 5 hydrogen atoms, and more preferably 1 to 3 hydrogen atoms, were substituted independently of one another by a corresponding number of substituents. It goes without saying that the substituents were only in their possible chemical positions, a person skilled in the art was able to determine (by experiment or theory) possible or impossible substitutions without undue effort. For example, an amino or hydroxyl group having a free hydrogen may be unstable when bound to a carbon atom having an unsaturated (e.g., olefinic) bond.

Unless otherwise defined, "substituents each independently selected from . . . " as used herein means that when one or more hydrogens on a group were replaced with substituents, the substituent species may be the same or different, and the substituents were independently selected.

Unless otherwise defined, the phrase " . . . the same or different, and each independently . . . " as used herein means that when one or more of the same substituent groups were present in a formula, the groups may be the same or different, and were each independently of one another. For example, L was $(CR_{01}R_{02})_s$, and when s was 2, i.e., L was $(CR_{01}R_{02})$—$(CR_{01}R_{02})$, both $R_{01}$ or $R_{02}$ may be the same or different and were independently of each other. For example, L may be $C(CH_3)(CN)$— $C(CH_2CH_3)(OH)$, $C(CH_3)(CN)$—$C(CH_3)(OH)$, or $C(CN)(CH_2CH_3)$—$C(OH)(CH_2CH_3)$.

Unless otherwise defined, any group herein may be substituted or unsubstituted. When the above-mentioned groups were substituted, the substituents were preferably 1 to 5 groups independently selected from the following groups: cyano, halogen (preferably fluorine or chlorine), $C_{1-8}$ alkyl (preferably $C_{1-6}$ alkyl, more preferably $C_{1-3}$ alkyl), $C_{1-8}$ alkoxy (preferably $C_{1-6}$ alkoxy, more preferably $C_{1-3}$ alkoxy), halogenated $C_{1-8}$ alkyl (preferably halogenated $C_{1-6}$ alkyl, more preferably halogenated $C_{1-3}$ alkyl), $C_{3-8}$ cycloalkyl (preferably $C_{3-6}$ cycloalkyl), halogenated $C_{1-8}$ alkoxy (preferably halogenated $C_{1-6}$ alkoxy, more preferably halogenated $C_{1-3}$ alkoxy), $C_{1-8}$ alkyl substituted amino, halogenated $C_{1-8}$ alkyl substituted amino, acetyl, hydroxyl, hydroxymethyl, hydroxyethyl, carboxyl, nitro, $C_{6-10}$ aryl (preferably phenyl), $C_{3-8}$ cycloalkoxy (preferably $C_{3-6}$ cycloalkoxy), $C_{2-8}$ alkenyl (preferably $C_{2-6}$ alkenyl, more preferably $C_{2-4}$ alkenyl), $C_{2-8}$ alkynyl (preferably $C_{2-6}$ alkynyl, more preferably $C_{2-4}$ alkynyl), —$CONR_{a0}R_{b0}$, —C(O)$OC_{1-10}$ alkyl (preferably —C(O)$OC_{1-6}$ alkyl, more preferably —C(O)$OC_{1-3}$ alkyl), —CHO, —OC(O)$C_{1-10}$ alkyl (preferably —OC(O)$C_{1-6}$ alkyl, more preferably —OC(O)$C_{1-3}$ alkyl), —$SO_2C_{1-10}$ alkyl (preferably —$SO_2C_{1-6}$ alkyl, more preferably —$SO_2C_{1-3}$ alkyl, —$SO_2C_{6-10}$ aryl (preferably —$SO_2C_6$ aryl, such as —$SO_2$— phenyl), —$COC_{6-10}$ aryl (preferably —$COC_6$ aryl, such as —CO— phenyl), a four- to six-membered saturated or unsaturated heteromonocyclic ring, a four- to six-membered saturated or unsaturated monocyclic ring, a five- to six-membered monocyclic heteroaryl ring, an eight- to ten-membered bicyclic heteroaryl ring, a spirocycle, a spiroheterocycle, a bridged ring, and a bridged heterocycle, wherein $R_{a0}$ and $R_{b0}$ were each independently hydrogen or $C_{1-3}$ alkyl.

The respective substituent groups described herein above may themselves be substituted with the groups described herein.

When a four- to six-membered saturated monoheterocyclic ring described herein was substituted, the positions of the substituents may be at their possible chemical positions, and representative substitutions of exemplary monoheterocyclic rings were shown below:

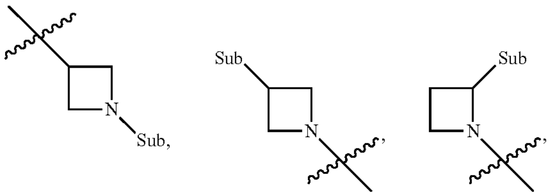

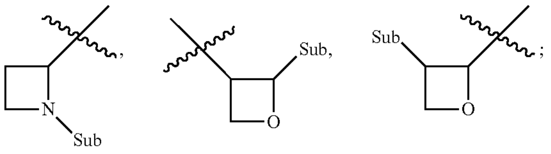

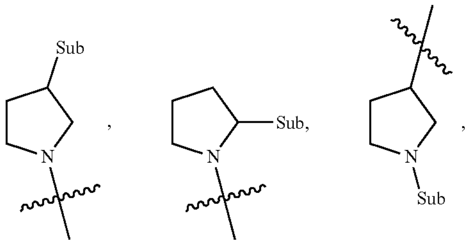

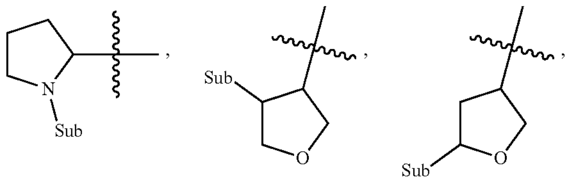

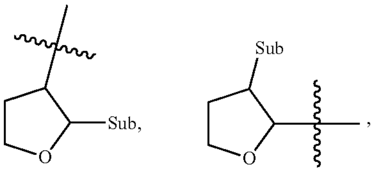

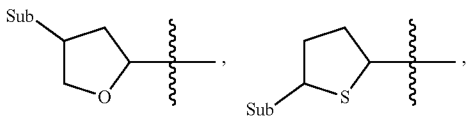

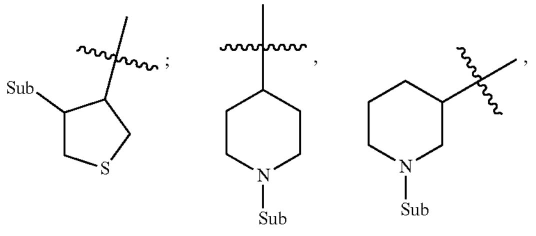

-continued

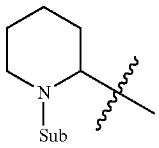,
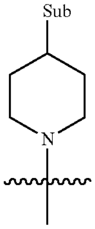,
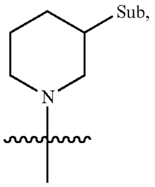

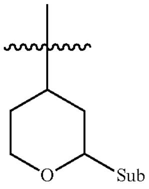,
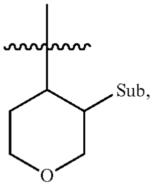
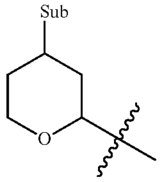,

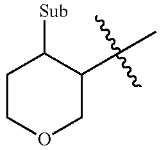,
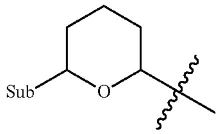,

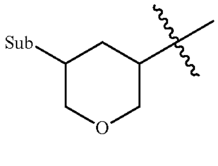,
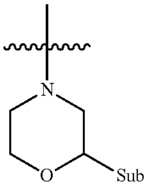,

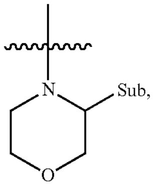
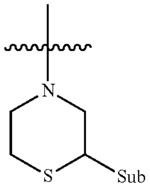,
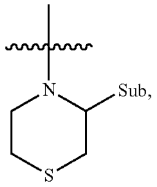

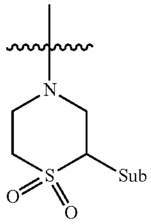,
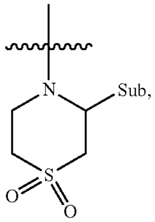
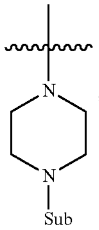,

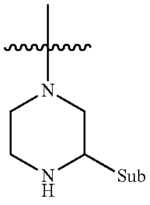,
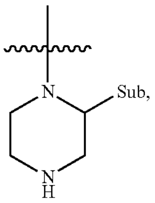
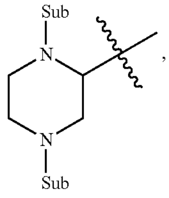,

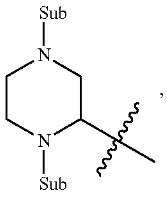, wherein "sub" represents the respective substituents described herein; and "∿∿" represents a bond to other atoms.

Pharmaceutical Compositions

In general, the compounds, or a pharmaceutically acceptable salt thereof, or a solvate thereof, or a stereoisomer thereof, or a prodrug thereof of the disclosure may be administered in a suitable formulation with one or more pharmaceutically acceptable carriers. These formulations were suitable for oral, rectal, topical, oral, and other parenteral (e.g., subcutaneous, intramuscular, intravenous, etc.) administration. For example, the formulations suitable for oral administration include capsules, tablets, granules, syrups, and the like. The compounds according to the present disclosure contained in these formulations may be solid powders or granules; solutions or suspensions in aqueous or non-aqueous liquids; or water-in-oil or oil-in-water emulsions, etc. The above-mentioned formulations can be made from the active compound and one or more carriers or adjuvants through conventional pharmaceutical procedures. The above-mentioned carriers were desirably compatible with the active compound or other adjuvants. For solid formulations, commonly used non-toxic carriers include, but were not limited to, mannitol, lactose, starch, magnesium stearate, cellulose, glucose, and sucrose, etc. The carriers for liquid preparations include water, physiological saline, aqueous dextrose, glycols, and polyethylene glycols, etc. The active compounds may form solutions or suspensions with the aforementioned carriers.

"Pharmaceutically acceptable carrier" means anon-toxic, inert, solid, and semi-solid or liquid filler, diluent, encapsulating material or formulation auxiliary or adjuvant of any type compatible with the subject, preferably a mammal, more preferably a human, to which it was administered and which was suitable for delivering the active agent to the target site without terminating the activity of the agent.

"Active substance of the present disclosure" or "active compound of the present disclosure" means a compound represented by formula (I) of the present disclosure, or a pharmaceutically acceptable salt thereof, or a solvate thereof, or a stereoisomer thereof, or a prodrug thereof, which has a relatively high CDK9 selective inhibitory activity.

The compositions of the present disclosure were formulated, dosed, and administered in a manner consistent with medical practice. The "therapeutically effective amount" of a compound administered will be determined by factors such as the particular condition being treated, the subject being treated, the cause of the condition, the target of the drug, and the mode of administration.

"Therapeutically effective amount" means an amount of a compound of the present disclosure or a pharmaceutically acceptable salt thereof, or a solvate thereof, or a stereoisomer thereof, or a prodrug thereof, which will elicit the biological or medical response of a subject, for example, reducing or inhibiting an enzyme or a protein activity, or ameliorating symptoms, alleviating conditions, slowing or delaying disease progression, or preventing a disease, etc.

Preferably, compound of the present disclosure, or the pharmaceutically acceptable salt thereof, or the solvate thereof, or the stereoisomer thereof, or the prodrug thereof was contained in the pharmaceutical composition or the pharmaceutical composition of the present disclosure in a therapeutically effective amount ranging from 0.1 mg/kg to 5 g/kg (body weight).

"Subject" means an animal, preferably a mammal, and more preferably a human. The term "mammal" refers to warm blood vertebrate mammals including, for example, cats, dogs, rabbits, bears, foxes, wolves, monkeys, deer, mice, pigs, and humans.

"Treatment" refers to alleviating, attenuating, preventing, or maintaining an existing disease or disorder (e.g., cancer). Treatment also includes curing, preventing the development of, or alleviating to some extent one or more of the symptoms of the disease or disorder.

The "pharmaceutically acceptable salt" includes pharmaceutically acceptable acid addition salts and pharmaceutically acceptable base addition salts. Pharmaceutically acceptable acid addition salts were those formed with inorganic or organic acids while maintaining the biological effectiveness of the free bases and have no undesirable effect. These salts can be prepared by methods known in the art.

"Pharmaceutically acceptable base addition salts" include, but were not limited to, salts of inorganic bases such as sodium, potassium, calcium, and magnesium salts, etc. Salts of organic bases include, but were not limited to, ammonium salts, triethylamine salts, lysine salts, and arginine salts, etc. These salts can be prepared by methods known in the art.

Reference herein to a "solvate" refers to a complex formed by the compound of the present disclosure with a solvent, which react in the solvent, or precipitate or crystallize out of the solvent. For example, a complex with water was referred to as a "hydrate". The solvates of the compounds of formula (I) were within the scope of the present disclosure.

When the compounds of formula (I) of the present disclosure contain one or more chiral centers, they may exist in different optically active forms. When the compound represented by formula (I) contains one chiral center, the compound comprises a pair of enantiomers. Both enantiomers of the compounds as well as mixtures of the pair of enantiomers, such as racemic mixtures, were also within the scope of the disclosure. Enantiomers can be resolved by methods known in the art, such as crystallization and chiral chromatography. When the compound represented by formula (I) contains more than one chiral center, the compound includes enantiomers and diastereomers. All enantiomers and diastereomers, as well as mixtures of enantiomers, mixtures of diastereomers, and mixtures of enantiomers and diastereomers of the compounds were also within the scope of the present disclosure. Enantiomers and diastereomers may be resolved by methods known in the art, such as crystallization and preparative chromatography.

The present disclosure includes prodrugs of the compounds described above. Prodrugs include known amino-protecting and carboxy-protecting groups which were hydrolyzed under physiological conditions or released by enzymatic reactions to yield the parent compound. For specific prodrug preparation methods, reference can be made (Saulnier, M. G.; Frennesson, D. B.; Deshpande, M. S.; Hansel, S. B and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M. J. Med. Chem. 2000, 43, 475).

Preparation Method

The present disclosure provides preparation methods for the compounds represented by formula (I), which can be synthesized using standard synthetic techniques known to those skilled in the art or using methods known in the art in combination with the methods described herein. The solvents, temperatures, and other reaction conditions provided herein may vary according to the skill in the art. The reactions may be used sequentially to provide compounds of the disclosure, or they may be used to synthesize fragments that were subsequently added by methods described herein and/or known in the art.

The compounds described herein can be synthesized using methods analogous to those described below or exemplified methods described in the embodiments, or related publications known to those skilled in the art, by using appropriate and alternative starting materials. The starting materials for the synthesis of the compounds described herein may be synthesized or may be commercially obtained. The compounds described herein and other related compounds having various substituents can be synthesized using techniques and starting materials known to those skilled in the art. General methods for preparing the compounds disclosed herein can be derived from reactions known in the art, and these reactions can be modified by reagents and conditions deemed appropriate by those skilled in the art to introduce various moieties in the molecules provided herein.

The main advantages of the present disclosure compared to the conventional art were as follows.

Provided were a series of structurally novel substituted pyrazolo[1,5-a]pyrimidin-7-amine derivatives having relatively high selective inhibitory activity against CDK9 as well as excellent in vivo pharmacokinetic activity with $IC_{50}$ values smaller than 100 nM, preferably smaller than 50 nM, and more preferably smaller than 10 nM. Therefore, they can be used as medicaments for treatment and/or prevention of diseases associated with or mediated by CDK9 activity.

The present disclosure was further illustrated in combination with the following specific examples. It should be understood that, these examples were illustrative only and were not intended to limit the scope of the disclosure. Experimental procedures without specifying the specific conditions in the following embodiments were generally those in accordance with conventional conditions, such as the conditions described in Molecular Cloning: Laboratory Manual, Sambrook et al. (New York: Cold Spring Harbor Laboratory Press, 1989), or as recommended by the manufacturer. Percentages and parts were percentages by weight, unless otherwise indicated. Unless otherwise defined, the terms used herein have the same meanings that were familiar to those skilled in the art. Moreover, any methods and materials similar or equivalent to those described herein can be used in the present disclosure.

Known starting materials may be employed or synthesized according to methods known in the art, or may be purchased from companies such as ABCR GmbH & Co. KG, Acros Organics, Aldrich Chemical Company, Accela ChemBio Inc, and Darry Chemicals.

Unless otherwise specified, the reactions in the embodiments were carried out under nitrogen or argon atmosphere.

DMF: dimethylformamide, DMSO: dimethyl sulfoxide, THF: tetrahydrofuran, DIEA: N,N-diisopropylethyl amine, EA: ethyl acetate, PE: petroleum ether, BINAP: (2R,3S)-2,2'-Bis-diphenylphosphino-1,1'-binaphthyl, NBS: N-bromosuccinimide, NCS: N-chlorosuccinimide, CDI: N,N'-carbonyldiimidazole, $Pd_2(dba)_3$: tris(dibenzylideneacetone) dipalladium, $Pd(dppf)Cl_2$:[1,1'-bis(diphenylphosphino) ferrocene]dichloropalladium, DPPA: diphenylphosphoryl azide, DBU: 1,8-diazabicycloundec-7-ene, TBAF: tetrabutylammonium fluoride, Na Ascorbate: sodium ascorbate, t-BuXPhosPd-G3:(2-Di-tert-butylphosphino-2',4',6'-triisopropyl-1,1'-biphenyl) (2'-amino-1,1'-biphenyl-2-yl) palladium (II) methanesulfonate.

As used herein, room temperature refers to about 20° C. to 30° C.

Intermediates

Preparation of Intermediate V1

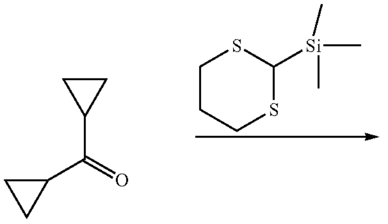

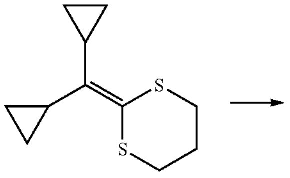

V1-1

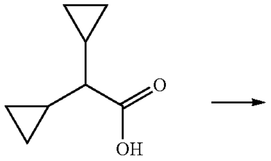

V1-2

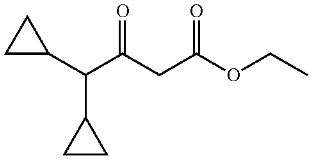

V1

Step 1: 1,3-dithian-2-yl (trimethyl) silane (4.23 g, 21.97 mmol) was dissolved in tetrahydrofuran (20 mL), cooled to −78° C., added with n-butyllithium (2.5 M, 8.79 mL), reacting for 0.5 h, then added dropwise with bicyclopropyl ketone (2.2 g, 19.97 mmol) in tetrahydrofuran (10 mL) solution, stirred at −78° C. for 1.5 h, then the mixture was warmed to room temperature for 16 h. Saturated sodium chloride solution (100 mL) was added. The mixture was extracted with ethyl acetate (100 mL), and the organic phase was dried over anhydrous sodium sulfate, filtered, and concentrated under reduced pressure. The residue was subjected to column chromatography on silica gel (40 g, 100% petroleum ether) to afford compound V1-1 (3.0 g, light-yellow liquid) in yield of 70.7%. MS m/z (ESI): 213.0 [M+1].

Step 2: compound V1-1 (3.0 g, 14.13 mmol) was dissolved in acetonitrile (50 mL) and water (12.5 mL), then trifluoroacetic acid (4.83 g, 42.38 mmol) and 30% hydrogen peroxide (20.82 g, 183.64 mmol) were added. The mixture was stirred at 80° C. for 1 h, cooled to 40° C., 2N of NaOH solution (40 mL) was added to the solution, stirring was continued for 0.5 h. Hydrochloric acid (40 mL) was added to neutralize the solution, followed by extraction with ethyl acetate (60 mL×3). The organic phase was dried over anhydrous sodium sulfate, and dried by means of a rotary dryer under reduced pressure. The residue was purified with silica gel column chromatography (40 g, 0 to 60% ethyl acetate/petroleum ether) to afford compound V1-2 (1.5 g, colorless oil) in yield of 75.8%. MS m/z (ESI): 139.0[M−1]

Step 3: 2,2-dicyclopropylacetic acid (1.50 g, 10.70 mmol) was dissolved in tetrahydrofuran (30 mL) in a reaction flask, CDI (2.31 g, 16.05 mmol) was added and reacted at room temperature for 16 h (as solution A). In another reaction flask, potassium (3-ethoxy-3-oxopropanoyl)oxy (2.73 g, 16.05 mmol) and magnesium chloride (1.02 g, 10.70 mmol) were added and heated to 50° C. for 16 h (as solution B). The solution A was added dropwise to the solution B (in about 5 minutes), and the mixture was stirred at room temperature for 16 h. The mixture was added with ethyl acetate (100 mL), washed with saturated sodium chloride solution (80 mL×3). The organic phase was dried over anhydrous sodium sulfate, filtered, and concentrated under reduced pressure. The residue was purified with silica gel column chromatography (40 g, 0~30% ethyl acetate in petroleum ether) to afford compound V1 (800 mg, colorless oil) in yield of 33.6%. MS m/z (ESI): 211.1 [M+1]

Preparation of Intermediate V2

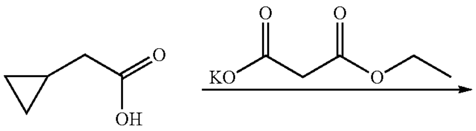

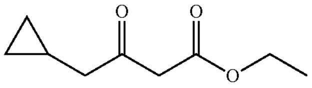

V2

The intermediate V2 (light-yellow oil, yield: 88.2%) can be prepared with reference to the scheme of step 3 for preparation of intermediate V1, merely different in that 2,2-dicyclopropylacetic acid was replaced with 2-cyclopropylacetic acid (CAS.NO: 5239-82-7). MS m/z (ESI): 171.1 [M+1]

Preparation of Intermediate V3

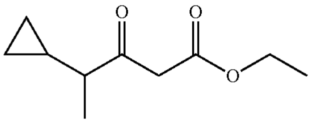

V3

The intermediate V3 (light-yellow liquid, yield 47.50%) can be prepared with reference to the scheme for preparation of intermediate V1, merely different in that bicyclopropyl ketone was replaced with 1-cyclopropylethanone. MS m/z (ESI): 185.1 [M+1].

Preparation of Intermediate V4

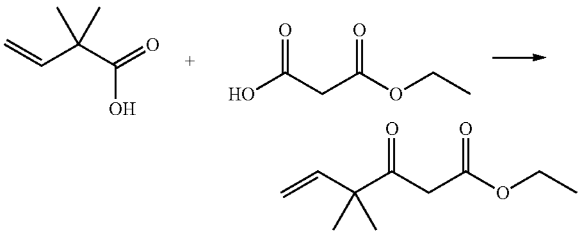

V4

Sulfuryl chloride (919.31 mg, 7.73 mmol) was added to 2,2-dimethyl-3-butynoic acid (588 mg, 5.15 mmol) and reacted under nitrogen at 80° C. for 2 h. The reaction solution was concentrated to obtain a yellow oil. N-butyllithium (2.5 M, 6.42 mL) was added to a solution of 3-ethoxy-3-oxopropanoic acid (1.14 g, 8.60 mmol) and tetrahydrofuran (15 mL) at −65° C. under nitrogen protection and reacted for 1 h at −10° C. solution A of the above yellow oil in tetrahydrofuran (15 mL) was added, and reacted at −65° C. for 1 h and at room temperature for 1 h. The reaction was poured into a solution of tetrahydrofuran/1N hydrochloric acid (20/20 mL) and stirred at room temperature for 2 h. The organic layer was separated, washed with saturated sodium carbonate, washed with saturated sodium chloride, concentrated and purified with column chromatography (petroleum ether: ethyl acetate=97.5%: 2.5%) to afford intermediate V4 (380 mg, 2.06 mmol, 71.97% yield) as a colorless oil, MS m/z (ESI): 185.2 [M+1].

Preparation of Intermediate V5

V5

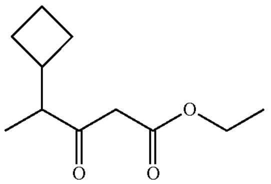

The intermediate V5 can be prepared with reference to the scheme of step 3 for preparation of intermediate V1, merely different in that 2,2-dicyclopropylacetic acid was replaced with 2-cyclobutylpropanoic acid (CAS. NO: 1082453-55-1).

Preparation of Intermediate V6

V6

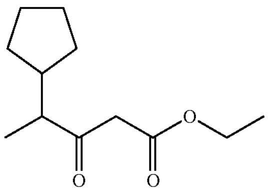

The intermediate V6 can be prepared with reference to the method for preparation of intermediate V1, merely different in that bicyclopropyl ketone was replaced with 1-cyclopropylethanone.

Preparation of Intermediate V7

V7

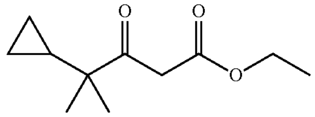

The intermediate V7 can be prepared with reference to the method for preparation of intermediate V4, merely different in that 2,2-dimethyl-3-butynoic acid was replaced with 2-cyclopropyl-2-methylpropanoic acid.

Preparation of Intermediate V8

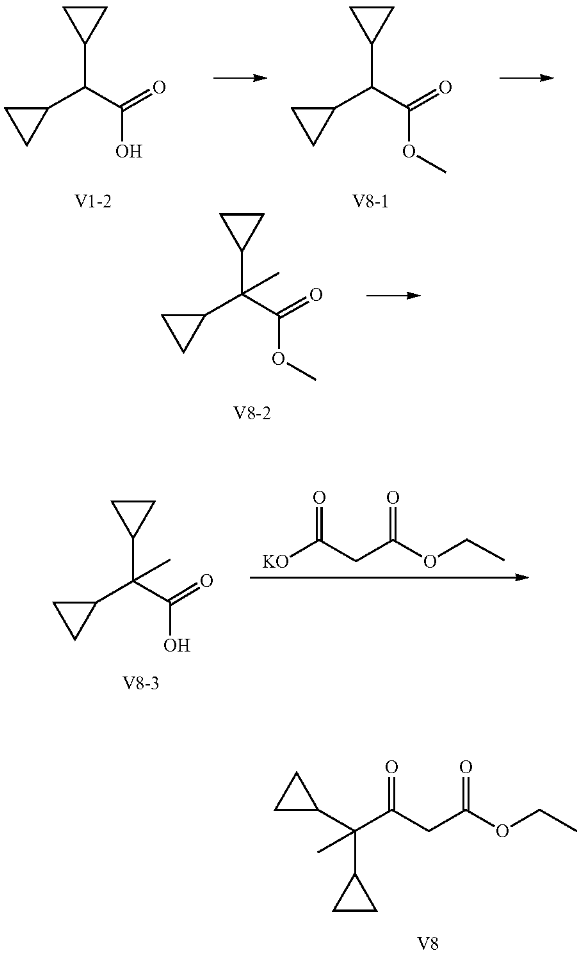

V1-2 V8-1 V8-2 V8-3 V8

Step 1: 2.2-dicyclopropylacetic acid (2.5 g, 17.83 mmol) was dissolved in methanol (50 mL), and then thionyl chloride (2.6 mL, 35.67 mmol) was added. The reaction solution was stirred at 70° C. for 6 h. The solvent was evaporated under reduced pressure. Ethyl acetate (60 mL) was added, washed with saturated sodium chloride solution (50 mL×3). The organic phase was dried over anhydrous sodium sulfate, filtered, and concentrated under reduced pressure. The residue was purified with silica gel column chromatography to afford methyl 2,2-dicyclopropyl acetate (1.6 g, colorless oil) in yield of 51.2%. $^1$H NMR (400 MHz, DMSO-d6) δ 3.60 (s, 3H), 1.17-1.08 (m, 1H), 1.02-0.88 (m, 2H), 0.53-0.43 (m, 2H), 0.41-0.31 (m, 2H), 0.26-0.20 (m, 2H), 0.14-0.06 (m, 2H).

Step 2: Methyl 2,2-dicyclopropyl acetate (1.5 g, 9.73 mmol) was dissolved in tetrahydrofuran (30 mL), cooled to −78° C., and lithium diisopropylamide (2 M, 14.59 mL) was added thereto. The reaction solution was stirred at −78° C. for 0.5 h, then slowly warmed to −20° C. and stirred for 0.5 h. After cooling to −78° C. again, iodomethane (4.14 g, 29.18 mmol) was added dropwise, and the mixture was slowly warmed to room temperature for 5 h. Then, the mixture was then cooled to −78° C. and added with lithium diisopropylamide (2 M, 14.59 mL). The reaction solution was stirred at −78° C. for 0.5 h, then slowly warmed to −20° C. and stirred for 0.5 h. After cooling to −78° C., iodomethane (4.14 g, 29.18 mmol) was added dropwise, and the mixture was slowly warmed to room temperature for 16 h. Ethyl acetate (80 mL) was added, and washed with saturated sodium chloride solution (80 mL×2). The organic phase was dried over anhydrous sodium sulfate, filtered, and concentrated under reduced pressure. The crude product methyl 2,2-dicyclopropyl propionate (1.5 g, light-yellow oil) was obtained in yield of 91.7%. It was used in the next step without further purification.

Step 3: Methyl 2,2-dicyclopropyl propionate (1.5 g, 8.92 mmol) was dissolved in methanol (10 mL), and then sodium hydroxide (1.43 g, 35.66 mmol) was dissolved in water (4 mL) and added therein. The reaction solution was stirred at room temperature for 16 h. The reaction was terminated, pH was adjusted to about 2 with 2N of hydrochloric acid, and extracted with ethyl acetate (50 mL×2). The organic phase was dried over anhydrous sodium sulfate, filtered, and concentrated under reduced pressure. The residue was purified with silica gel column chromatography to afford 2,2-dicyclopropylpropionic acid (900 mg, light-yellow oil) in yield of 65.5%. MS m/z (ESI): 155.1 [M+1]. $^1$H NMR (400 MHz, DMSO-d6) δ 1.01-0.89 (m, 2H), 0.66 (s, 3H), 0.33-0.20 (m, 8H).

Step 4: 2,2-dicyclopropyl propionic acid (900 mg, 5.84 mmol) was dissolved in tetrahydrofuran (15 mL) in a reaction flask, then N,N'-carbonyldiimidazole (1.26 g, 8.75 mmol) was added thereto, and the mixture reacted at room temperature for 16 h (as solution A). In another reaction flask, potassium (3-ethoxy-3-oxopropanoyl)oxy (2.48 g, 14.59 mmol) was dissolved in tetrahydrofuran (25 mL) and added with magnesium chloride (1.11 g, 11.67 mmol), and the mixture was heated to 50° C. for 16 h (as solution B). The solution A was added dropwise to the solution B (in about 5 minutes), and the mixture was stirred at 30° C. for 16 h. The reaction was terminated. Ethyl acetate (50 mL) was added, and washed with saturated sodium chloride solution (50 mL×3). The organic phase was dried over anhydrous sodium sulfate, filtered, and concentrated under reduced pressure. The residue was purified with silica gel column chromatography to afford ethyl 4,4-dicyclopropyl-3-carbonyl-pentanoate (600 mg, light-yellow oil) in yield of 45.8%. MS m/z (ESI): 225.1 [M+1].

Preparation of Intermediate V9

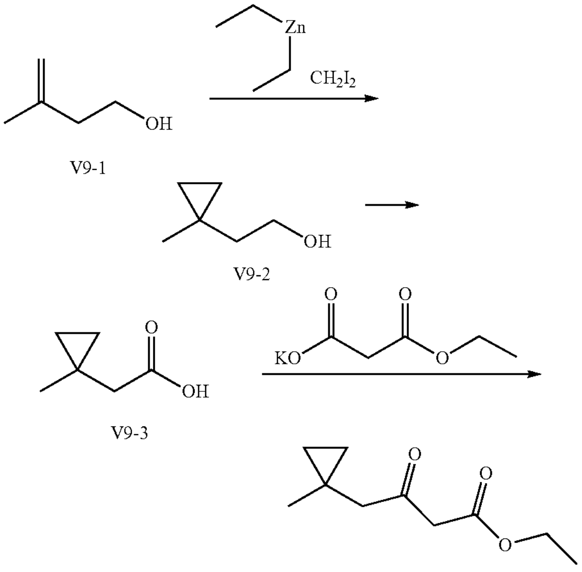

V9-1

V9-2

V9-3

V9

Step 1: 3-methyl-3-buten-1-ol (8.6 g, 99.85 mmol) was dissolved in dichloromethane (200 mL) at −20° C., diethylzinc (1 M, 299.54 mL) and diiodomethane (79.98 g, 299.54 mmol) were added, and the mixture reacted for 4 h at −20° C. The reaction solution was slowly added with saturated aqueous ammonium chloride solution, extracted with 200 mL of dichloromethane twice, dried over anhydrous sodium sulfate and dried by means of a rotary dryer. The crude was purified with column chromatography (petroleum ether: ethyl acetate=80%: 20%) to afford 2-(1-methylcyclopropyl) ethanol (5.6 g, yield of 56.0%) as light-yellow liquid. $^1$H NMR (400 MHz, DMSO-d6) δ4.27 (s, 1H), 3.46 (dd, J=6.8, 4.8 Hz, 2H), 1.40-1.32 (m, 2H), 0.97 (s, 3H), 0.23 (t, J=4.8 Hz, 2H), 0.15 (dd, J=5.2, 4.0 Hz, 2H).

Step 2: 2-(1-methylcyclopropyl) ethanol (4.6 g, 45.93 mmol) was dissolved in acetone in ice bath, and Jones reagent (2.2 M, 62.63 mL) was added. After reacting 16 h at room temperature, the reaction solution was added with water (70 mL), extracted with 50 mL of dichloromethane twice, washed with brine twice, dried over anhydrous sodium sulfate, and dried by means of a rotary dryer at low temperature. The residue was purified with column chromatography (petroleum ether: ethyl acetate=70%: 30%) to afford 2-(1-methylcyclopropyl) acetic acid (1.7 g, yield 32.43%) as a light-yellow liquid. MS m/z (ESI): 113.1[M−1].

Step 3: N,N'-carbonyldiimidazole (1.92 g, 11.83 mmol) was added to a solution of 2-(1-methylcyclopropyl) acetic acid (900 mg, 1.67 mmol) and tetrahydrofuran (30 mL) at 0° C. under nitrogen, and the mixture was stirred at room temperature for 16 h (Solution 1). Potassium (3-ethoxy-3-oxopropanoyl)oxy (2.01 g, 11.83 mmol), magnesium chloride (749.07 mg, 7.88 mmol), and tetrahydrofuran (30 mL) were heated to 50° C. for 16 h under nitrogen. After cooling to 0° C., the Solution 1 was added dropwise into the reaction solution, and the mixture was stirred at room temperature for 16 h. The reaction solution was added to ice water and extracted with ethyl acetate (50 mL*3), and the organic layer was concentrated to dryness to obtain the crude product. The crude was purified with column chromatography (petroleum ether: ethyl acetate=90%: 10%) to afford ethyl 4-(1-methylcyclopropyl)-3-oxobutanoate (1.2 g, yield of 82.61%) as a light-yellow liquid. MS m/z (ESI): 185.1 [M+1].

Preparation of Intermediate V10

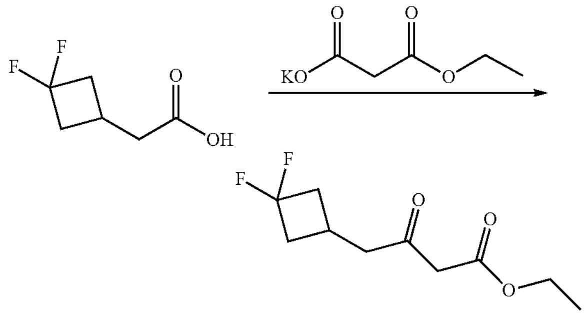

V10

N,N'-carbonyldiimidazole (404.67 mg, 2.50 mmol) was added to a solution of 2-(3,3-difluorocyclobutyl) acetic acid (250 mg, 1.67 mmol) and tetrahydrofuran (15 mL) at 0° C. under nitrogen, and the mixture was stirred at room temperature for 16 h (Solution 1). Potassium (3-ethoxy-3-oxopropanoyl)oxy (425.16 mg, 2.50 mmol), magnesium chloride (158.20 mg, 1.67 mmol), and tetrahydrofuran (15 mL) were heated to 50° C. for 16 h under nitrogen protection. After cooling to 0° C., the Solution 1 was added dropwise into the reaction solution, and the mixture was stirred at room temperature for 16 h. The reaction solution was added to ice water and extracted with ethyl acetate (15 mL*3), and the organic layer was concentrated to dryness to obtain the crude product. The crude was purified with column chromatography (petroleum ether: ethyl acetate=90%: 10%) to afford ethyl 4-(3,3-difluorocyclobutyl)-3-oxobutanoate (290 mg, 79.08% yield) as a light-yellow liquid. MS m/z (ESI): 221.1 [M+1].

Preparation of Intermediate V11

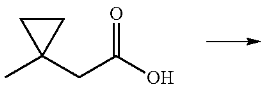

V9-3

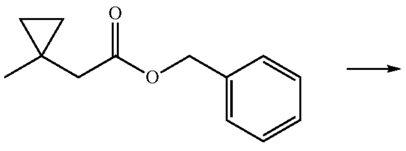

V11-3

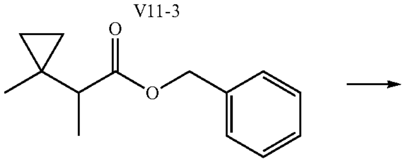

V11-4

-continued

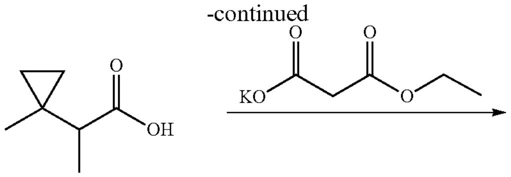

V11-5

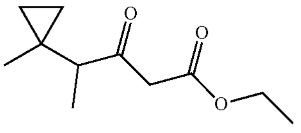

V11

Step 1: 2-(1-Methylcyclopropyl) acetic acid (1.7 g, 14.89 mmol) was dissolved in N,N-dimethylformamide (15 mL), and potassium carbonate (6.18 g, 44.68 mmol) and benzyl bromide (3.06 g, 17.87 mmol) were added. The reaction was allowed to proceed overnight at 25° C. The reaction solution was added with water 50 mL, extracted with 30 mL of ethyl acetate twice, washed with saturated brine twice, dried over anhydrous sodium sulfate, and dried by means of a rotary dryer. The crude was purified with column chromatography (petroleum ether: ethyl acetate=95%: 5%) to afford benzyl 2-(1-methylcyclopropyl) acetate (2.1 g, yield: 69.03%) as light-yellow liquid. $^1$H NMR (400 MHz, DMSO-d6) δ 7.45-7.24 (m, 5H), 5.10 (s, 2H), 2.29 (s, 2H), 1.06 (s, 3H), 0.41 (t, J=4.8 Hz, 2H), 0.30 (dd, J=5.6, 4.0 Hz, 2H).

Step 2: benzyl 2-(1-methylcyclopropyl) acetate (1.6 g, 7.83 mmol) was dissolved in THF (20 mL), and iodomethane (5.52 g, 39.17 mmol) was added at −78° C. The mixture was stirred for 30 min, and lithium bis(trimethylsilyl)amide (1 M, 15.67 mL) was added. The temperature slowly returned to room temperature, and stirred for 2 h. The reaction solution was added with saturated ammonium chloride, and extracted with 50 mL of ethyl acetate twice. The organic phases were combined, washed with saturated common salt twice, dried over anhydrous sodium sulfate, and dried by means of a rotary dryer. Residue was purified with column chromatography (petroleum ether: ethyl acetate=95%: 5%) to afford benzyl 2-(1-methylcyclopropyl) propanoate (1.6 g, yield 93.57%) as a light-yellow liquid.

Step 3: benzyl 2-(1-methylcyclopropyl) propanoate (2.1 g, 9.62 mmol) was dissolved in methanol (20 mL) and added to a solution of sodium hydroxide (3.85 g, 96.20 mmol) in water (10 mL). The mixture reacted at 30° C. for 16 h. The reaction solution was dried by means of a rotary dryer to remove most of methanol, extracted with methyl tert-butyl ether (2*30 mL), adjusted to about pH=4 with hydrochloric acid, extracted with methyl tert-butyl ether (2*40 mL), washed with saturated brine twice, dried over anhydrous sodium sulfate, and dried by means of a rotary dryer to obtain 2-(1-methylcyclopropyl)propanoic acid (1.1 g, yield: 89.21%) as a light-yellow liquid. MS m/z (ESI): 127.1[M−1].

Step 4: preparation was performed according to step 4 of intermediate V8. MS m/z (ESI): 199.1 [M+1].

Preparation of Intermediate V12

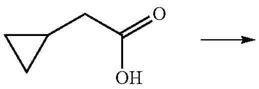

-continued

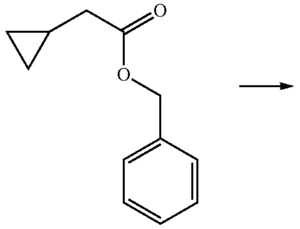

V12-1

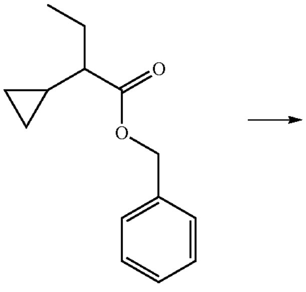

V12-2

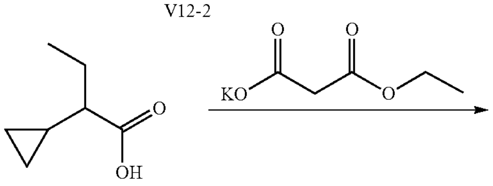

V12-3

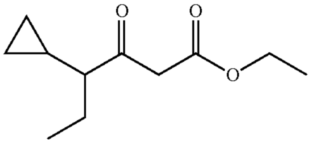

V12

Step 1: 2-cyclopropylacetic acid (50 g, 499.42 mmol) was dissolved in N,N-dimethylformamide (500 mL), potassium carbonate (207.07 g, 1.50 mol) and benzyl bromide (111.04 g, 649.25 mmol) were added, and the mixture reacted at 30° C. for 16 h. The reaction solution was added with 2 L of water, and extracted with ethyl acetate (3*500 mL). The organic phases were combined, washed with saturated brine for 3 times, dried over anhydrous sodium sulfate, filtered and dried by means of a rotary dryer. Residue was purified by means of combi-flash chromatography using petroleum ether: ethyl acetate=10:1 was obtained to afford compound V12-1 (89 g, yield: 93.68%) as a light-yellow liquid. $^1$H NMR (400 MHz, DMSO-d6) δ 7.42-7.25 (m, 5H), 5.08 (s, 2H), 2.27 (d, J=4 Hz, 2H), 1.01-0.90 (m, 1H), 0.51-0.38 (m, 2H), 0.19-0.05 (m, 2H).

Step 2: lithium bis(trimethylsilyl)amide (1 M, 78.85 mL) was added to a three-neck flask, and compound V12-1 (5 g, 26.28 mmol) and iodoethane (41.00 g, 262.83 mmol) in tetrahydrofuran (70 mL) were added dropwise under argon protection at −78° C. The mixture reacted at −40° C. for 2 h. The reaction solution was added with saturated ammonium chloride solution, and extracted with ethyl acetate (2*200 mL). The organic phases were combined, and washed with saturated common salt twice, followed by drying over anhydrous sodium sulfate, filtration, and drying by means of a rotary dryer. Residue was purified by means of combi-flash chromatography using petroleum ether: ethyl acetate=10:1 was obtained to afford compound V12-2 (2.85 g, yield: 49.67%) as a light-yellow liquid. $^1$H NMR (400 MHz, DMSO-d6) δ 7.40-7.26 (m, 5H), 5.10 (s, 2H), 1.57-1.65 (m, 3H), 0.90-0.79 (m, 4H), 0.52-0.43 (m, 1H), 0.43-0.35 (m, 1H), 0.21-0.12 (m, 2H).

Step 3: compound V12-2 (22 g, 100.78 mmol) was dissolved in methanol (200 mL) and added with a solution of sodium hydroxide (32.25 g, 806.26 mmol) in water (100 mL) dropwise under ice bath. After the addition was completed, the mixture reacted at 30° C. for 16 h. Rotary drying was performed to remove methanol from the reaction solution, 200 mL of water was added to the residue, extraction was performed with 150 mL of methyl tert-butyl ether 3 times, the pH of the aqueous phase was adjusted to 4, extraction was performed with 150 mL of methyl tert-butyl ether 3 times. The organic phases were combined, washed with saturated salt water twice, dried over anhydrous sodium sulfate, followed by filtration and drying by means of a rotary dryer at low temperature. Compound V12-3 (12 g, yield: 90.2%) was obtained as light-yellow liquid. MS m/z (ESI): 127.2[M−1].

Step 4: carbonyl diimidazole (18.96 g, 117.03 mmol) was dissolved in tetrahydrofuran (200 mL) and compound V12-3 (10 g, 78.02 mmol) was added at 0° C. The mixture was stirred at room temperature for 16 h. Potassium (3-ethoxy-3-oxopropanoyl)oxy (39.84 g, 234.07 mmol) was dissolved in tetrahydrofuran (200 mL) and magnesium chloride (22.24 g, 234.07 mmol) was added. The mixture was stirred at 50° C. for 16 h. The liquid in the first flask was then slowly added into the second flask dropwise. The mixture was stirred at room temperature for 16 h. The reaction solution was added with water, and extracted with ethyl acetate (3*150 mL). The organic phases were combined, washed with saturated brine twice, dried over anhydrous sodium sulfate, and dried by means of a rotary dryer. Residue was purified by means of combi-flash chromatography using petroleum ether: ethyl acetate=10:1 was obtained to afford compound V12 (14.8 g, yield: 95.68%) as a yellow liquid. MS m/z (ESI): 199 [M+1].

Preparation of Intermediate V13

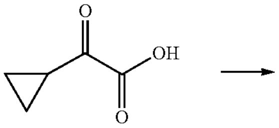

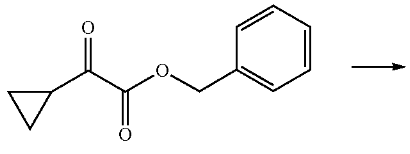

V13-1

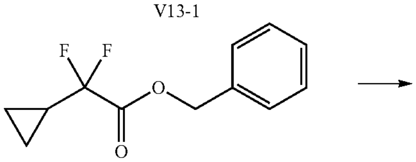

V13-2

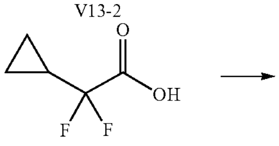

V13-3

-continued

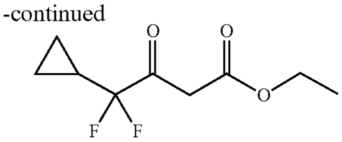

V13

Step 1: oxalyl chloride (1.78 g, 14.02 mmol, 1.20 mL) was added dropwise to a solution of 2-cyclopropyl-2-oxoacetic acid (1 g, 8.76 mmol) and dichloromethane (15 mL) at 0° C. under nitrogen protection. Thereafter, N,N-dimethylformamide (6.41 mg, 87.64 μmol) was added, and the mixture was warmed to room temperature and reacted for 1 h. After the reaction solution was concentrated to dryness, dichloromethane (15 mL) was added, a solution of benzyl alcohol (1.33 g, 12.27 mmol, 1.27 mL), triethylamine (2.22 g, 21.91 mmol, 3.06 mL) and dichloromethane (15 mL) were added dropwise at 0° C., and the mixture reacted at room temperature for 1 h. The reaction solution was poured into ice water and extracted with dichloromethane (15 mL*2). The organic layers were combined and washed with saturated brine, dried over anhydrous sodium sulfate, and concentrated to afford the crude product. The crude was purified with column chromatography (petroleum ether: ethyl acetate=90%: 10%) to afford compound V13-1 (1.26 g, yield of 67.56%) as a colorless liquid (no ion flux).

Step 2: bis(2-methoxyethyl)aminosulfur trifluoride (3.90 g, 17.63 mmol) was added to compound V13-1 (900 mg, 4.41 mmol) and dichloromethane (30 mL) at room temperature under nitrogen protection, and the mixture was heated to 50° C. and reacted for 16 h. The reaction solution was poured into ice, and extracted with dichloromethane (50 mL*2). The organic layers were combined and washed with saturated aqueous sodium bicarbonate solution, dried over anhydrous sodium sulfate, and concentrated to afford the crude product. The crude was purified with column chromatography (petroleum ether: ethyl acetate=70%: 30%) to afford compound V13-2 (555 mg, yield of 55.67%) as a colorless liquid (no ion flux).

Step 3: compound V13-2 (555 mg, 2.45 mmol), sodium hydroxide (490.64 mg, 12.27 mmol), methanol (5 mL), and water (5 mL) were mixed and reacted at room temperature for 16 h. The methanol was removed under reduced pressure, the aqueous phase was washed with methyl tert-butyl ether (15 mL*2). The collected aqueous phase was cooled to 0° C., added with concentrated hydrochloric acid to pH=2, and extracted with dichloromethane (15 mL*2). The organic layers were combined, dried over anhydrous sodium sulfate, and concentrated to afford compound V13-3 (320 mg, 2.35 mmol, yield 95.84%) as a yellow liquid. MS m/z (ESI): 135.1[M−1].

Step 4: N,N'-carbonyldiimidazole (507.70 mg, 3.53 mmol) was added to a solution of compound V13-3 (320 mg, 2.35 mmol) in tetrahydrofuran (20 mL) at 0° C. under nitrogen protection, and the mixture reacted at room temperature for 16 h. Potassium (3-ethoxy-3-oxopropanoyl)oxy (1.00 g, 5.88 mmol), magnesium chloride (447.73 mg, 4.70 mmol), and tetrahydrofuran (20 mL) were heated to 50° C. and reacted for 16 h under nitrogen protection. After cooling to 0° C., the solution 1 was added dropwise into the reaction solution, and the mixture was reacted at room temperature for 16 h. The reaction solution was added with ethyl acetate (50 mL) and water (50 mL), the organic layer was separated and washed with saturated sodium bicarbonate solution and saturated sodium chloride solution, dried over anhydrous sodium sulfate, and concentrated to dryness to obtain the crude product. The crude was purified with column chromatography (petroleum ether: ethyl acetate=80%: 20%) to afford compound V13 (100 mg, yield of 20.63%) as a yellow oil.

Preparation of Intermediate V14

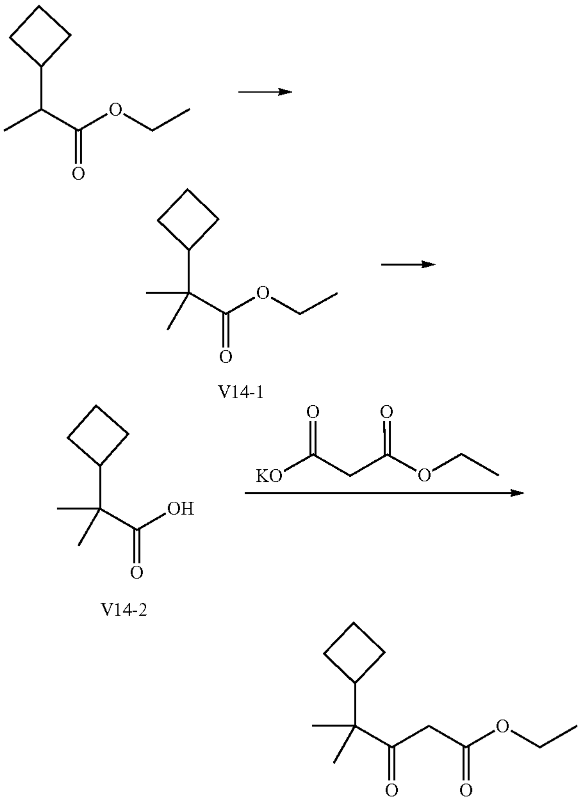

V14-1

V14-2

V14

Preparation was performed according to the scheme of intermediate V12 to afford compound V14. MS m/z (ESI): 213.1 [M+1].

Preparation of Intermediate V15

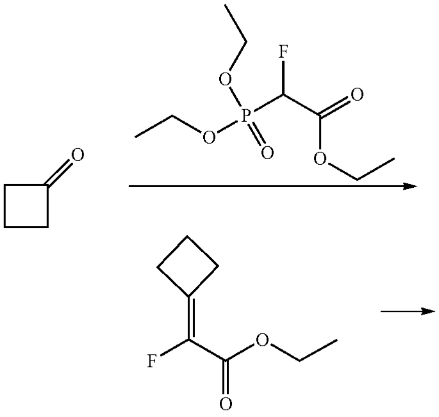

V15-1

-continued

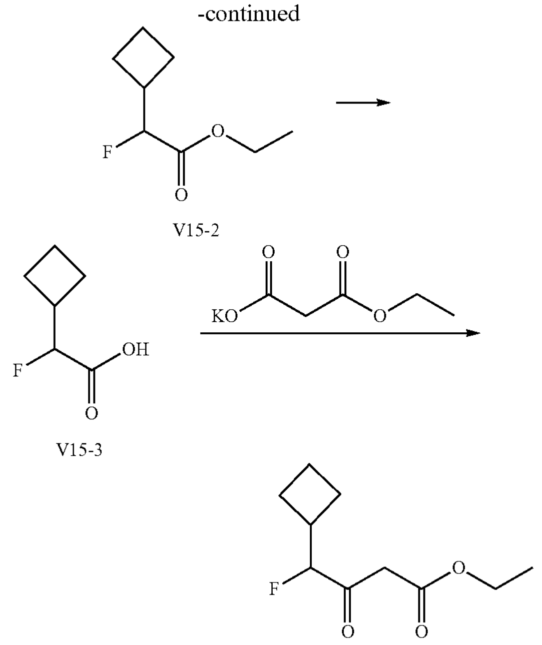

V15-2

V15-3

V15

Step 1: triethyl 2-fluoro-2-phosphorylacetate (1.90 g, 7.85 mmol) was dissolved in 10 mL of THF, replaced with nitrogen three times, then cooled to −70° C., while n-butyllithium (2.5 M, 3.42 mL) was slowly added dropwise and stirred at −70° C. for 0.5 h. The mixture was warmed to 0° C. and stirred for 0.5 h. Cyclobutanone (0.5 g, 7.13 mmol) was then slowly added dropwise at −70° C. and then stirred at room temperature for 3 h. The reaction was quenched with water (20 mL), extracted with ethyl acetate (20 mL×2), the organic phase was washed with saturated sodium chloride solution (10 mL), dried over anhydrous sodium sulfate, filtered, and concentrated under reduced pressure. The resulting residue was purified with silica gel column chromatography with an eluent of 0-20% ethyl acetate in petroleum ether to afford compound V15-1 (0.8 g, light-yellow liquid) in yield of 70.9%.

Step 2: compound V15-1 (0.8 g, 5.06 mmol) was dissolved in methanol (15 mL), and 10% wet Pd/C (538.26 mg, 505.79 μmol) was added, and then hydrogen replacement was performed three times. The mixture was stirred under hydrogen (15 Psi) at 25° C. for 1 h. The catalyst was filtered off and concentrated under reduced pressure to afford compound V15-2 (0.7 g, colorless liquid) in yield of 86.40%, which was used in the next step of reaction without further purification.

Step 3: compound V15-2 (0.7 g, 4.37 mmol) and sodium hydroxide (524.39 mg, 13.11 mmol) were dissolved in methanol (5 mL) and water (2 mL). The mixture was stirred at 30° C. for 2 h. The pH was adjusted to 5 with 2 M of dilute hydrochloric acid, and extracted with dichloromethane (10 mL×3). The organic phases were combined and dried by means of a rotary dryer. The resulting residue was purified with silica gel column chromatography with an eluent of 0-20% ethyl acetate in petroleum ether to afford compound V15-3 (400 mg, colorless liquid) in yield of 69.27%. MS m/z (ESI): 131.1[M−1].

Step 4: compound V15-3 (0.4 g, 3.03 mmol) was dissolved in tetrahydrofuran (6 mL) in a reaction flask, and then DCI (736.30 mg, 4.54 mmol) was added thereto, followed by reacting at room temperature for 16 h (as solution A). Potassium (3-ethoxy-3-oxopropanoyl)oxy (2.06 g, 12.11 mmol) was added to anhydrous magnesium chloride (864.68 mg, 9.08 mmol) and tetrahydrofuran (20 mL) and heated to 50° C. under argon protection for 16 h (as solution B). The solution A was slowly added dropwise to the solution B, and the mixture was stirred at 30° C. for 16 h. The reaction solution was added with 30 mL of water and extracted with ethyl acetate (30 mL×3). The organic phases were combined and washed with brine, dried over anhydrous sodium sulfate, and dried by means of a rotary dryer under reduced pressure. The resulting residue was purified with silica gel column chromatography with an eluent of 0-10% ethyl acetate in petroleum ether to afford compound V15 (230 mg, light-yellow oil) in yield of 37.57%. MS m/z (ESI): 203.2 [M+1].

Preparation of Intermediate V16

V16

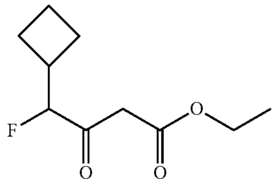

Preparation was performed according to the scheme of intermediate V15, merely different in that cyclobutanone was replaced with cyclopentanone. MS m/z (ESI): 217.1 [M+1].

Preparation of Intermediate V17

V17

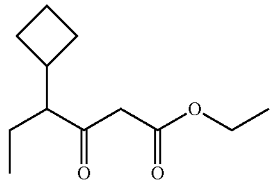

Preparation was performed according to the scheme of intermediate V15, merely different in that triethyl 2-fluoro-2-phosphorylacetate was replaced with ethyl 2-(diethoxyphosphoryl)butanoate. MS m/z (ESI): 213.1 [M+1].

Preparation of Intermediate V18

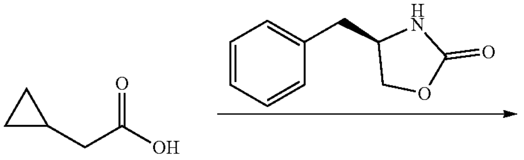

-continued

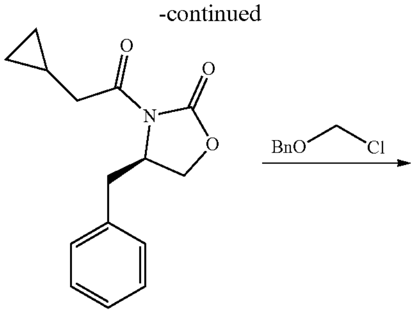

V18-1

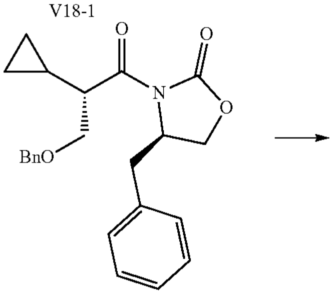

V18-2

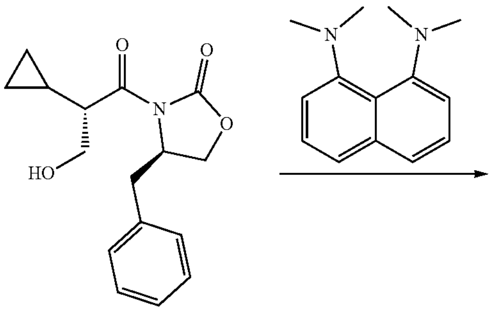

V18-3

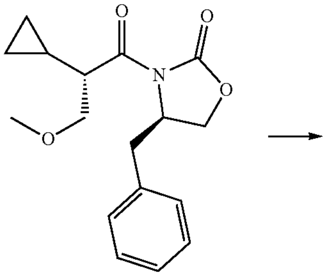

V18-4

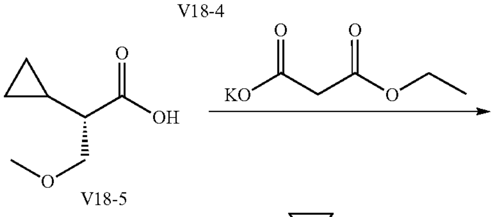

V18-5

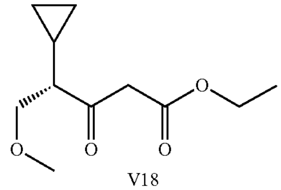

V18

Step 1: triethylamine (6.06 g, 59.93 mmol, 8.36 mL) was added dropwise to a solution of 2-cyclopropylacetic acid (5 g, 49.94 mmol) and tetrahydrofuran (100 mL) at −78° C. under nitrogen protection. Upon completion of addition, pivaloyl chloride (6.62 g, 54.94 mmol, 6.76 mL) was added dropwise at −78° C., and the reaction solution turned from a clear yellow solution to a white suspension. After completion of addition, the reaction solution was warmed to 0° C. and reacted for 1.5 h (Solution 1). N-butyllithium (1.6 M, 37.46 mL) was added dropwise to a solution of (R)-4-benzyl-2-oxazolidinone (8.85 g, 49.94 mmol) and tetrahydrofuran (50 mL) at −78° C. under nitrogen protection, and the reaction solution turned from a clear colorless solution to a white suspension. After the addition was complete, the reaction rises to 0° C. and becomes a yellow suspension. The reaction solution reacted at 0° C. for 0.5 h. This solution was slowly added dropwise to the Solution 1 at 0° C., and then the mixture was stirred at room temperature for 2 h. The reaction was quenched with water (200 mL), and extracted with ethyl acetate (300 mL×3). The organic phases were combined and washed with brine, dried over anhydrous sodium sulfate, and concentrated under reduced pressure to obtain the crude product. The resulting residue was purified with silica gel column chromatography with an eluent of 0-20% ethyl acetate in petroleum ether to afford compound V18-1 (8.5 g, colorless oil) in yield of 65.64%. MS m/z (ESI): 260.1 [M+1].

Step 2: compound V18-1 (7.5 g, 28.92 mmol) was dissolved in dichloromethane (200 mL), cooled to 0° C. under argon protection, then anhydrous titanium tetrachloride (6.03 g, 31.82 mmol, 3.49 mL) was slowly added dropwise. After completion of adding, the solution was yellow at 0° C., stirred for 5 min, then N,N-diisopropylethyl amine (4.30 g, 33.26 mmol, 5.79 mL) was slowly added dropwise, and the solution turned black at the end, while stirring at the maintained temperature for 1 h. Finally, benzyl chloromethyl ether (9.06 g, 57.85 mmol, 8.05 mL) was added dropwise and stirred at 0° C. for 6 h. The reaction was quenched with saturated aqueous ammonium chloride solution (150 mL), and then extracted with dichloromethane (100 mL×3). The organic phases were combined, washed with brine, dried over anhydrous sodium sulfate, filtered, and concentrated under reduced pressure to afford the crude product. The resulting residue was purified with silica gel column chromatography with eluent of 0-15% ethyl acetate in petroleum ether to afford compound V18-2 (9 g, yield: 82%) as white solid. MS m/z (ESI): 380.2 [M+1].

Step 3: compound V18-2 (9 g, 23.72 mmol) was dissolved in methanol (120 mL), 10% wet Pd/C (2.37 g, 4.74 mmol) was added, and then hydrogen replacement was performed three times. The mixture was stirred under hydrogen (15 Psi) at room temperature for 2 h. The catalyst was filtered off, and the organic phase was concentrated under reduced pressure to afford compound V18-3 (6 g, white solid) in yield of 87.43%. MS m/z (ESI): 290.1[M+H]+.

Step 4: compound V18-3 (3 g, 10.37 mmol) was dissolved in dichloromethane (50 mL), cooled to 0° C. under argon, then 1,8-bisdimethylaminonaphthalene (5.56 g, 25.92 mmol) and trimethyloxonium tetrafluoroborate (3.07 g, 20.74 mmol) were slowly added. The mixture was warmed slowly to room temperature and stirred for 16 h. The reaction was quenched with saturated aqueous ammonium chloride solution (50 mL), and extracted with dichloromethane (50 mL×3). The organic phases were combined and washed with diluted hydrochloric acid, dried over anhydrous sodium sulfate, and concentrated under reduced pressure to afford the crude product. The resulting residue was purified with silica gel column chromatography with an eluent of 0-15% ethyl acetate in petroleum ether to afford compound V18-4 (2.6 g, white solid) in yield of 66%. MS m/z (ESI): 304.2 [M+1].

Step 5: compound V18-4 (2.6 g, 8.57 mmol) was dissolved in tetrahydrofuran (25 mL) and water (15 mL), cooled to 0° C., and then 33% hydrogen peroxide (3.89 g, 34.28 mmol, 3.44 mL) and lithium hydroxide monohydrate (720.47 mg, 17.14 mmol) were added dropwise. The mixture was slowly warmed to room temperature and stirred for 1 h. The reaction was quenched by slowly adding aqueous sodium sulfite solution under ice bath, and the reaction solution was extracted with methyl tert-butyl ether (20 mL×2) to remove impurities. The aqueous phase was adjusted to pH of about 5 with dilute hydrochloric acid, and extracted with methyl tert-butyl ether (20 mL×3). The organic phases were combined and dried over anhydrous sodium sulfate, concentrated, and dried by means of a rotary dryer to afford crude compound V18-5 (1.2 g, colorless oil) in yield of 97.12%. MS m/z (ESI): 143.1[M−1].

Step 6: compound V18-5 (0.7 g, 4.86 mmol) was dissolved in tetrahydrofuran (10 mL) in a reaction flask, and then CDI (1.18 g, 7.28 mmol) was added thereto, followed by reacting room temperature for 16 h (as solution A). Potassium (3-ethoxy-3-oxopropanoyl)oxy (3.31 g, 19.42 mmol) was added to anhydrous magnesium chloride (1.39 g, 14.57 mmol) and tetrahydrofuran (20 mL) and heated to 50° C. under argon protection for 16 h (as solution B). The solution A was added dropwise to the solution B (in about 10 minutes), and the mixture was stirred at 70° C. for 16 h. The reaction solution was added with 30 mL of water and extracted with ethyl acetate (30 mL×3). The combined organic phases were washed with brine, dried over anhydrous sodium sulfate, and dried by means of a rotary dryer under reduced pressure. The resulting residue was purified with silica gel column chromatography with an eluent of 0-15% ethyl acetate in petroleum ether to afford compound V18 (0.9 g, light-yellow oil) in yield of 86.51%. MS m/z (ESI): 215.2 [M+1].

Preparation of Intermediate V19

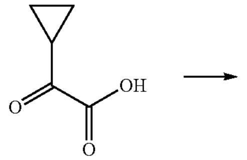

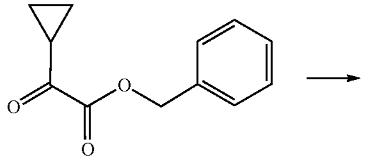

V19-1

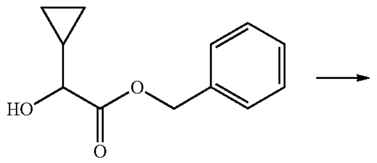

V19-2

-continued

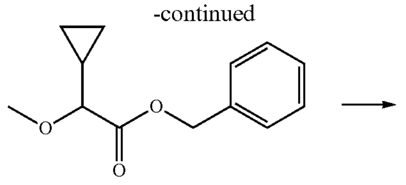

V19-3

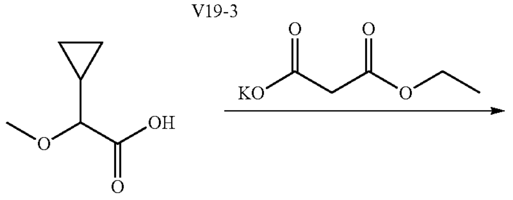

V19-4

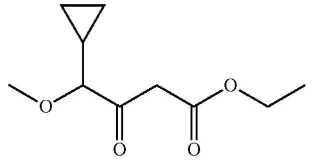

V19

Step 1: oxalyl chloride (3.56 g, 28.05 mmol, 2.39 mL) was added dropwise to a solution of 2-cyclopropyl-2-oxoacetic acid (2 g, 17.53 mmol) and dichloromethane (50 mL) at 0° C. under nitrogen protection. After completion of the addition, N,N-dimethylformamide (12.81 mg, 175.29 μmol, 13.57 μL) was added, and the mixture was warmed to room temperature and reacted for 1 h. The reaction solution, after being concentrated to dryness and redissolved in dichloromethane (50 mL), was added into a solution of benzyl alcohol (2.65 g, 24.54 mmol, 2.54 mL), triethylamine (4.43 g, 43.82 mmol, 6.11 mL), and dichloromethane (50 mL) dropwise at 0° C. After the adding was completed, the mixture reacted at room temperature for 1 h. The reaction solution was poured into ice water and extracted with dichloromethane (30 mL*2). The organic layers were combined and washed with saturated brine, dried over anhydrous sodium sulfate, and concentrated to afford the crude product. The resulting residue was purified with silica gel column chromatography with an eluent of 0-10% ethyl acetate in petroleum ether to afford compound V19-1 (2.1 g, colorless liquid) in yield of 58.66%. The desired product was carried on to the next step without MS, TLC plate detection.

Step 2: compound V19-1 (1.9 g, 9.30 mmol) was dissolved in methanol (30 mL), and sodium borohydride (422.38 mg, 11.16 mmol) was slowly added under cooling to −10° C., and the mixture was stirred at −10° C. for 30 min. The reaction was quenched by adding water. The reaction solution was extracted with ethyl acetate (40 mL×3), washed with brine, dried over anhydrous sodium sulfate, and concentrated under reduced pressure. The resulting residue was purified with silica gel column chromatography with an eluent of 0-20% ethyl acetate in petroleum ether to afford compound V19-2 (1.5 g, colorless oil) in yield of 78.18%. MS m/z (ESI): 207.1 [M+1].

Step 3: compound V19-2 (1.5 g, 7.27 mmol), iodomethane (5.16 g, 36.37 mmol, 2.35 mL), and silver oxide (3.37 g, 14.55 mmol, 472.12 μL) were dissolved in acetonitrile (15 mL) in a sealed tube, sparged with argon for a while, sealed well, heated to 70° C. and stirred overnight. The reaction solution was filtered to remove solid and dried by means of a rotary dryer under reduced pressure to afford the crude product. The resulting residue was purified with silica gel column chromatography with an eluent of 0-10% ethyl acetate in petroleum ether to afford compound V19-3 (1.1 g, colorless oil) in yield of 68.66%. MS m/z (ESI): 221.1 [M+1].

Step 4: compound V19-3 (1.1 g, 4.99 mmol) and sodium hydroxide (599.24 mg, 14.98 mmol) were dissolved in methanol (15 mL) and water (5 mL). The mixture was warmed to 30° C. and stirred for 4 h. The solvent was removed under reduced pressure, the pH was adjusted to 3 with 2 M of dilute hydrochloric acid, followed by extraction with ethyl acetate (15 mL×3). The organic phases were combined, dried over anhydrous sodium sulfate, and concentrated under reduced pressure. The resulting residue was purified with silica gel column chromatography with an eluent of 0-20% ethyl acetate in petroleum ether to afford compound V19-4 (0.6 g, colorless oil) in yield of 92.32%. MS m/z (ESI): 129.1[M−1].

Step 5: preparation was performed according to the step 6 of intermediate V18 to afford compound V19. MS m/z (ESI): 201.1 [M+1].

Preparation of Intermediate V20

V20

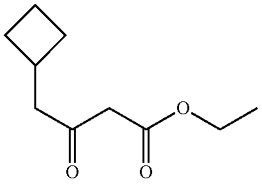

Preparation was performed according to the scheme of intermediate V2 to afford compound V20. MS m/z (ESI): 185.1 [M+1].

Preparation of Intermediate V21

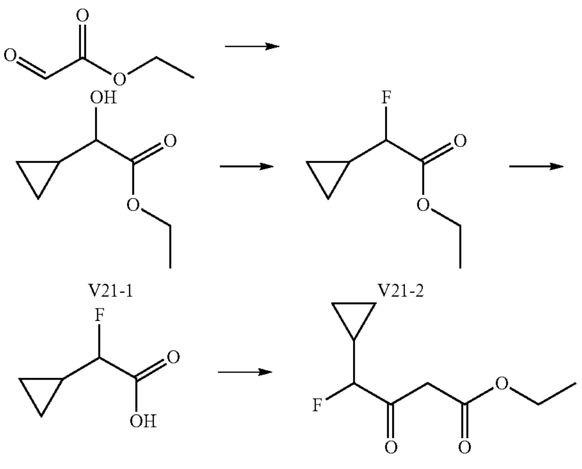

V21-1

V21-2

V21-3

V21

Step 1: ethyl glyoxylate (5 g, 24.49 mmol) was dissolved in tetrahydrofuran (30 mL) under nitrogen protection. Cyclopropyl magnesium bromide (1.78 g, 12.24 mmol) was added slowly while cooling to −78° C. The mixture reacted at −20° C. for 3 h. The reaction was quenched with ice water, extracted with ethyl acetate (30 mL×2), the combined organic phases were dried over anhydrous sodium sulfate, and concentrated under reduced pressure. Separation was performed by column chromatography (PE:EA=4:1) to afford compound V21-1 (620 mg, colorless liquid) in yield of 17.56%. MS m/z (ESI): 145.0 [M+1].

Step 2: compound V21-1 (620 mg, 4.30 mmol) was dissolved in 8 mL of dichloromethane. DAST (1.39 g, 8.60 mmol) was added slowly at −70° C. under nitrogen protection. The reaction solution was stirred at room temperature for 12 h, then added with 20 ml of water, and extracted with dichloromethane (20 mL×2). The organic phases were combined, dried over anhydrous sodium sulfate, and concentrated under reduced pressure to afford compound V21-2 (448 mg, brown liquid) in yield of 78%. MS m/z (ESI): 147.2 [M+1].

Step 3: compound V21-2 (448 mg, 3.07 mmol) was dissolved in water (3 mL) and methanol (1 mL). Lithium hydroxide (293.62 mg, 12.26 mmol) was added followed by nitrogen protection, and the reaction solution was stirred at room temperature for 2 h. After completion of the reaction, the reaction solution was concentrated under reduced pressure, adjusted to pH 1 with hydrochloric acid, and extracted with dichloromethane (20 mL×2). The organic phases were combined, dried over anhydrous sodium sulfate, and concentrated under reduced pressure to afford compound V21-3 (380 mg, brown liquid) in yield of 78%. MS m/z (ESI): 117.1[M−1].

Step 4: preparation was performed according to the step 6 of intermediate V18 to afford compound V21. MS m/z (ESI): 189.1 [M+1].

Preparation of Intermediate V22

V22

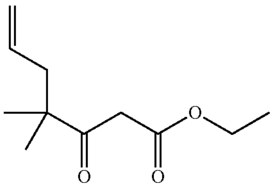

Preparation was performed according to the scheme of intermediate V4 to afford compound V22. MS m/z (ESI): 199.1[M+H$^+$].

Preparation of Intermediate 3-2

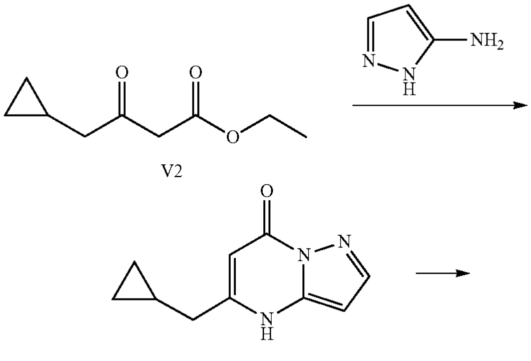

V2

3-1

-continued

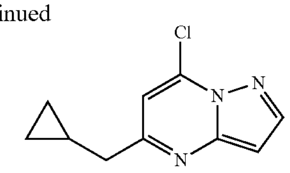

3-2

Step 1: compound V2 (1.2 g, 7.05 mmol) and 1H-pyrazol-5-amine (585.8 mg, 7.05 mmol) were dissolved in acetic acid (8 mL), and the reaction solution was stirred at 70° C. for 4 h. The solvent was evaporated under reduced pressure, ethyl acetate (15 ml) was added, and the solid was precipitated, filtered and dried to afford compound 3-1 (800 mg, brown solid) in yield of 60.0%. MS m/z (ESI): 190.1 [M+1].

Step 2: compound 3-1 (500 mg, 2.64 mmol) was dissolved in phosphorus oxychloride (6 mL) and heated to 120° C., followed by stirring for 3 h. The reaction was terminated, cooled to room temperature. The reaction solution was poured into ice water (60 g), extracted with dichloromethane (80 mL), and the organic phase was dried over anhydrous sodium sulfate, filtered, and concentrated under reduced pressure. The residue was purified with silica gel column chromatography (20 g, 0%-40% ethyl acetate in petroleum ether) to afford compound 3-2 (300 mg, light-yellow oil) in yield of 54.7%. MS m/z (ESI): 208.1 [M+1].

Intermediate 4-2 to Intermediate 23-2

Intermediates 4-2 to 23-2 were prepared using ethyl oxobutanoate as starting material, with reference to the schemes of intermediate 3-2.

| Structures of intermediates | MS m/z (ESI) [M + 1] |
| --- | --- |
| 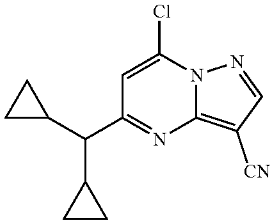 4-2 | 273.1 |
| 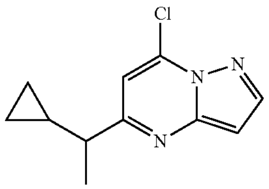 5-2 | 222.0 |
| 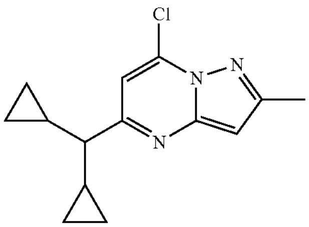 8-2 | 262.0 |

-continued

| Structures of intermediates | MS m/z (ESI) [M + 1] |
| --- | --- |
| 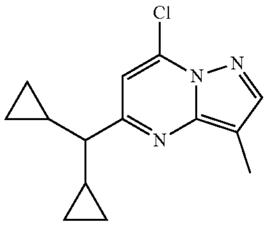 9-2 | 262.0 |
| 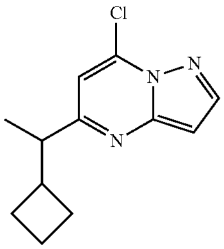 11-2 | 236.1 |
| 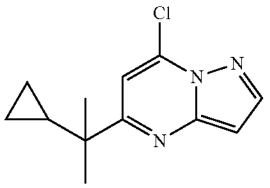 12-2 | 236.1 |
| 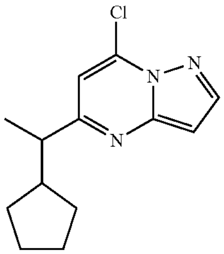 13-2 | 250.1 |
| 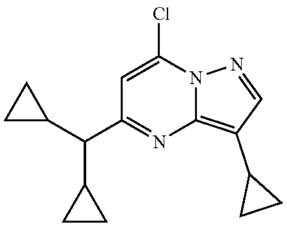 14-2 | 288.0 |

-continued
| Structures of intermediates | MS m/z (ESI) [M + 1] |
|---|---|
| 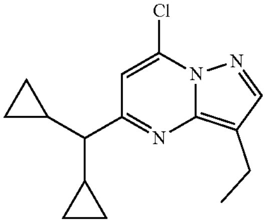<br>16-2 | 276.1 |
| 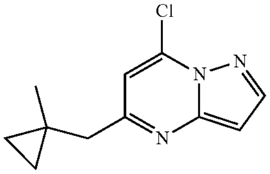<br>17-2 | 222.1 |
| 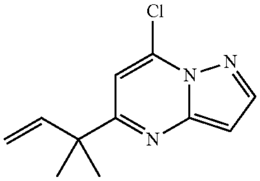<br>18-2 | 222.1 |
| 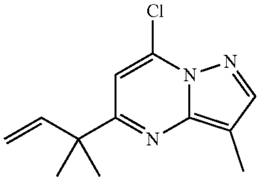<br>19-2 | 236.1 |
| 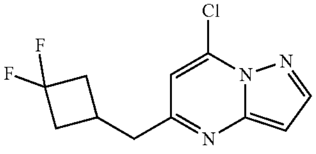<br>20-2 | 258.0 |
| 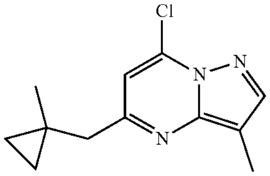<br>21-2 | 236.1 |
-continued
| Structures of intermediates | MS m/z (ESI) [M + 1] |
|---|---|
| 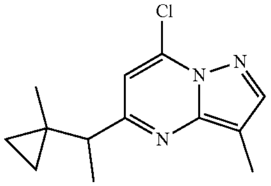<br>22-2 | 250.1 |
| 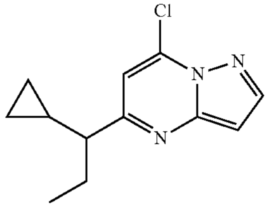<br>23-2 | 236.1 |
Preparation of Intermediate 24-2
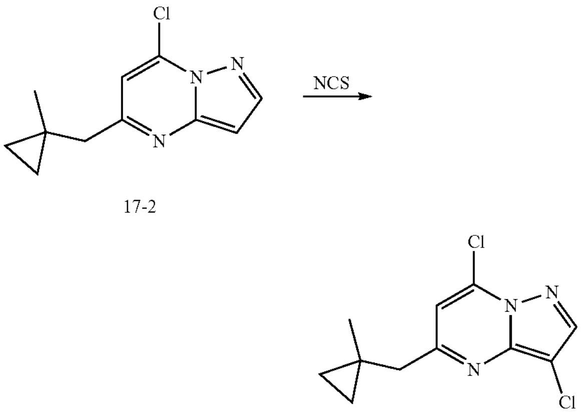
17-2
24-2
Intermediate 24-2 was prepared according to the scheme of compound 2-1. MS m/z (ESI): 256.0 [M+1].
Preparation of Intermediate 27-3
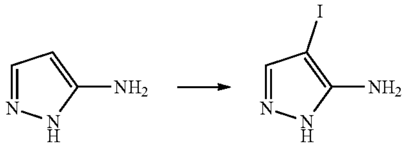

-continued

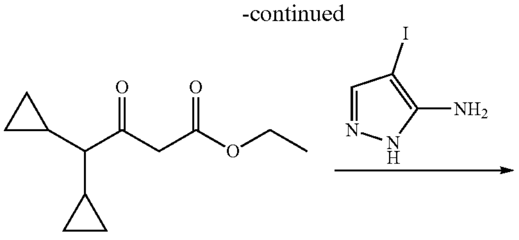

V1

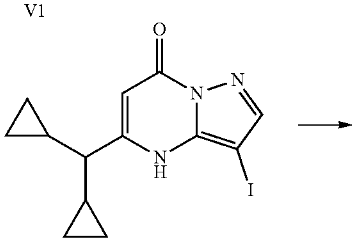

27-1

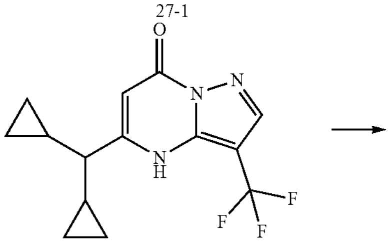

27-2

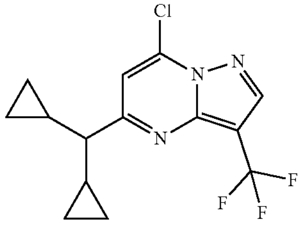

27-3

Step 1: hydrogen peroxide (818.72 mg, 7.22 mmol, purity of 30%) and iodine (1.53 g, 6.02 mmol) were added to a solution of 1H-pyrazol-5-amine (1 g, 12.03 mmol) and water (10 mL) at room temperature, and thereafter, the mixture reacted at room temperature for 1 h. 20 mL of saturated sodium sulfite solution was added into the reaction solution. After stirring for 10 minutes, the reaction solution was filtered, and the filter cake was washed with water and dried to obtain 4-iodo-1H-pyrazol-5-amine (1.3 g, 51.69% yield). The crude product was directly used for the next step. MS m/z (ESI): 210.0 [M+1].

Step 2: compound V1 (1 g, 4.76 mmol), 4-iodo-1H-pyrazol-5-amine (993.91 mg, 4.76 mmol), and acetic acid (35 mL) were mixed and reacted at 70° C. for 1 h under nitrogen protection. The reaction solution was concentrated to dryness to afford the crude product. The crude product was purified with column chromatography (dichloromethane:dichloromethane/tetrahydrofuran/ethyl acetate (volume ratio 2/1/1)=70%: 30%) to afford compound 27-1 (300 mg, yield 17.76%) as a yellow solid. MS m/z (ESI): 356.0 [M+1].

Step 3: cuprous iodide (257.38 mg, 1.35 mmol) and potassium fluoride (78.51 mg, 1.35 mmol) were added to a reaction flask and nitrogen replacement was performed. Then, compound 27-1 (240 mg, 675.73 μmol), N,N-dimethylformamide (12 mL), and trimethyl (trifluoromethyl)silane (288.25 mg, 2.03 mmol) were added thereto, followed by reacting at 90° C. for 16 h (condenser tube+nitrogen balloon). After cooling, cuprous iodide (257.38 mg, 1.35 mmol), potassium fluoride (78.51 mg, 1.35 mmol), and trimethyl (trifluoromethyl)silane (288.25 mg, 2.03 mmol) were supplementally added, and the mixture was heated to 90° C. again and reacted for 16 h. The reaction vessel was replaced with a large sealed tube, and reaction was further performed at 95° C. for 6 h. The reaction solution was poured into ice water, filtered to remove the insoluble matter, and extracted with ethyl acetate (20 mL*2). The organic layers were combined, washed with water (10 mL*3) and saturated brine (15 mL), dried over anhydrous sodium sulfate, and concentrated to afford the crude product. The crude was purified with column chromatography (petroleum ether: ethyl acetate=70%: 30%) to afford compound 27-2 (137 mg, 293.70 μmol, yield 43.46%) as a tan solid. MS m/z (ESI): 298.2 [M+1].

Step 4: compound 27-2 (127 mg, 427.21 μmol) and phosphorus oxychloride (655.06 mg, 4.27 mmol) were heated to 110° C. and reacted for 3 h. The excessive phosphorus oxychloride in the reaction solution was evaporated to dryness, the residue was added into ice water and extracted with dichloromethane (20 mL*3), and the organic layer was washed with saturated brine, dried over anhydrous sodium sulfate, and concentrated to dryness to obtain the crude product. The crude was purified with column chromatography (petroleum ether: ethyl acetate=70%: 30%) to afford compound 27-3 (86 mg, yield 39.30%) as a light-yellow solid. MS m/z (ESI): 316.1 [M+1].

Intermediate 25-2 to Intermediate 50-2

Intermediates 25-2 to 50-2 were prepared using ethyl oxobutanoate as starting material with reference to the above-mentioned schemes.

| Structures of intermediates | MS m/z (ESI) [M + 1] |
|---|---|
| 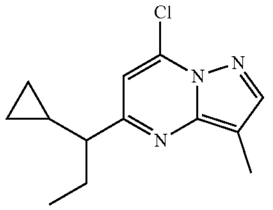 25-2 | 250.1 |
| 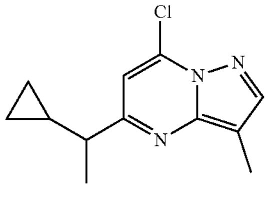 26-2 | 236.1 |
| 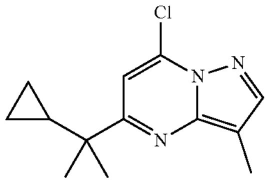 28-2 | 250.2 |

-continued
| Structures of intermediates | MS m/z (ESI) [M + 1] |
|---|---|
| 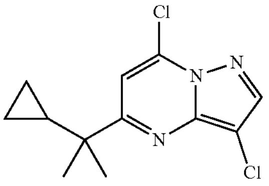 29-2 | 270.0 |
| 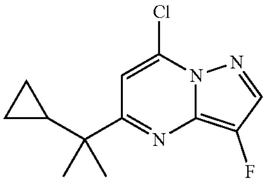 30-2 | 254.0 |
| 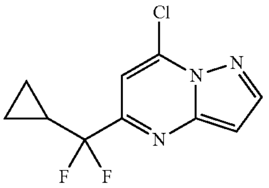 31-2 | 244.1 |
| 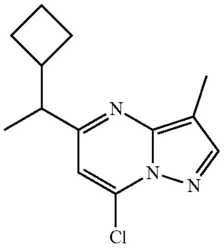 32-2 | 250.1 |
| 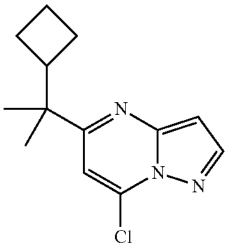 33-2 | 250.1 |
-continued
| Structures of intermediates | MS m/z (ESI) [M + 1] |
|---|---|
| 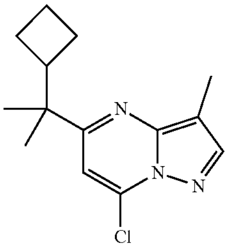 34-2 | 264.1 |
| 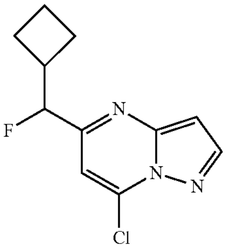 35-2 | 240.1 |
| 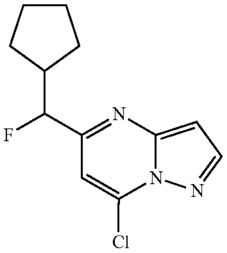 36-2 | 254.1 |
| 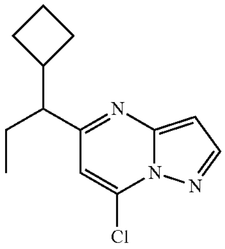 37-2 | 250.1 |
| 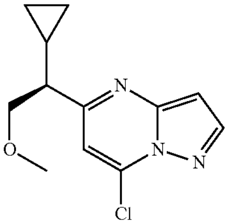 38-2 | 252.1 |

-continued
| Structures of intermediates | MS m/z (ESI) [M + 1] |
| --- | --- |
| 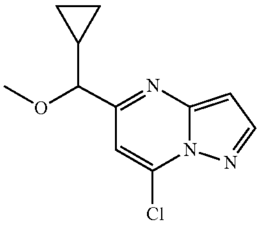 39-2 | 238.1 |
| 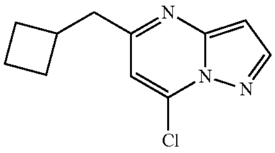 40-2 | 222.1 |
| 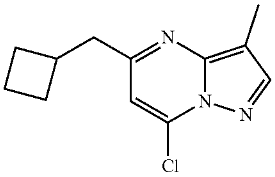 41-2 | 236.1 |
| 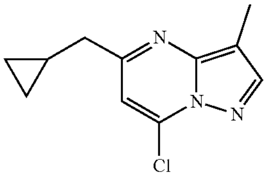 42-2 | 222.1 |
| 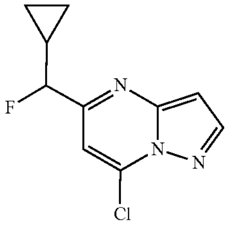 43-2 | 226.1 |
| 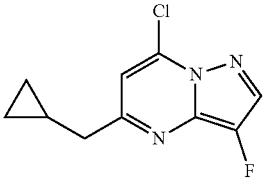 44-2 | 226.1 |
-continued
| Structures of intermediates | MS m/z (ESI) [M + 1] |
| --- | --- |
| 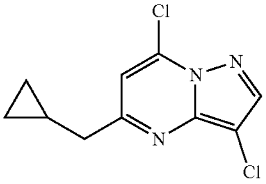 45-2 | 242 |
| 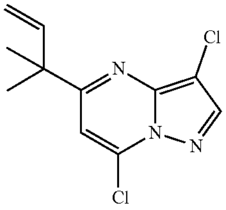 46-2 | 256 |
| 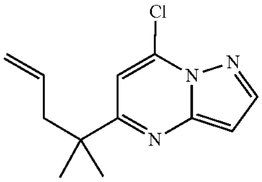 47-2 | 236.1 |
| 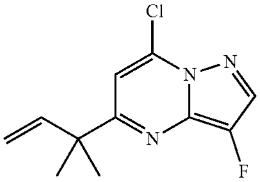 48-2 | 240.1 |
| 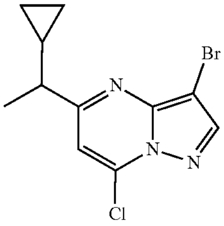 49-2 | 300.0 |
| 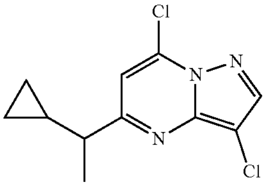 50-2 | 256.0 |

-continued

| Structures of intermediates | MS m/z (ESI) [M + 1] |
|---|---|
| 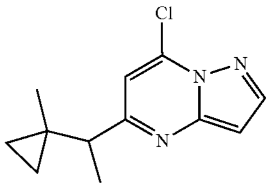 51-2 | 236.1 |

Example 1: Preparation of Compound Z-1

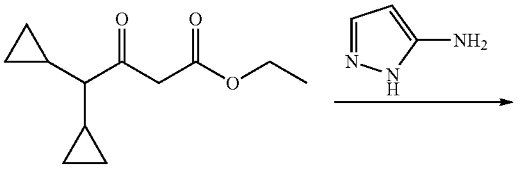

V1

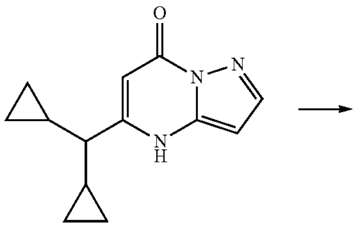

1-1

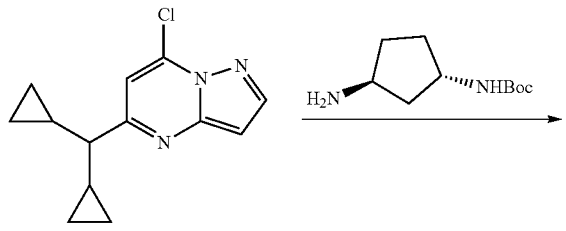

1-2

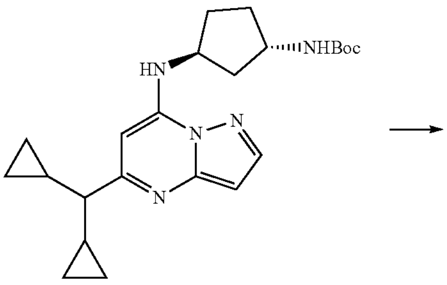

1-3

-continued

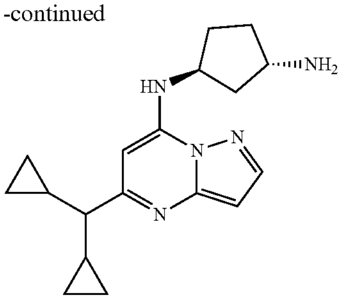

Z-1

Step 1: compound V1 (0.7 g, 3.33 mmol) and 1H-pyrazol-5-amine (276.6 mg, 3.33 mmol) were dissolved in acetic acid (6 mL) and the reaction solution was stirred at 70° C. for 4 h. The solvent was evaporated under reduced pressure, ethyl acetate (15 ml) was added, and the solid was precipitated, filtered and dried to afford compound 1-1 (500 mg, brown solid) in yield of 65.5%. MS m/z (ESI): 230.1 [M+1]

Step 2: compound 1-1 (500.0 mg, 2.18 mmol) was dissolved in phosphorus oxychloride (6 mL) and heated to 120° C., followed by stirring for 3 h. The reaction solution was cooled to room temperature, poured into ice water (60), extracted with dichloromethane (80 mL), and the organic phase was dried over anhydrous sodium sulfate, filtered, and concentrated under reduced pressure. The residue was purified with silica gel column chromatography (20 g, 0%-40% EA/DCM) to afford compound 1-2 (350 mg, light-yellow oil) in yield of 64.8%. MS m/z (ESI): 248.0 [M+1].

Step 3: compound 1-2 (150.0 mg, 605.5 μmol) and tert-butyl ((1S,3S)-3-aminocyclopentyl) carbamate (121.27 mg, 605.52 μmol) were dissolved in acetonitrile (20 mL), and potassium carbonate (251.0 mg, 1.81 mmol) was added thereto. The reaction solution was stirred at 90° C. for 16 h. The reaction solution was diluted with ethyl acetate (80 mL), and washed with saturated sodium chloride solution (80 mL×3), and the organic phase was dried over anhydrous sodium sulfate, filtered, and concentrated under reduced pressure to afford compound 1-3 (180 mg, light-yellow oil) in yield of 72.2%. MS m/z (ESI): 412.2 [M+1].

Step 4: compound 1-3 (180 mg, 437.38 μmol) was dissolved in 1,4-dioxane (3 mL), 4 M of hydrochloric acid solution (3.0 mL) was added, and the mixture was stirred at room temperature for 3 h. The solvent was evaporated under reduced pressure. The reaction solution was added with water (60 mL) and extracted with ethyl acetate (50 mL). The aqueous phase was adjusted to pH=9-10 with saturated sodium carbonate solution, and extracted with ethyl acetate (60 mL×2). The organic phase was dried over anhydrous sodium sulfate, filtered, and concentrated under reduced pressure. Compound Z-1 (43.5 mg) was separated by preparative HPLC chromatography, with yield of 31.3%. MS m/z (ESI): 312.2 [M+1]; $^1$H NMR (400 MHz, DMSO-d6) δ 7.96 (d, J=2.4 Hz, 1H), 7.39 (d, J=7.2 Hz, 1H), 6.27 (d, J=2.4 Hz, 1H), 6.00 (s, 1H), 4.25-4.10 (m, 1H), 3.42-3.35 (m, 1H), 2.26-2.10 (m, 1H), 2.04-1.53 (m, 6H), 1.34-1.09 (m, 4H), 0.59-0.47 (m, 2H), 0.36-0.16 (m, 4H), 0.13-0.02 (m, 2H).

Example 2: Preparation of Compound Z-2

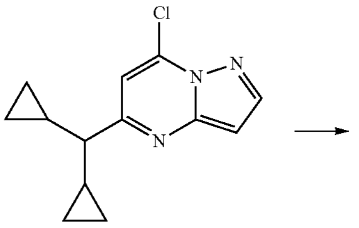

1-2

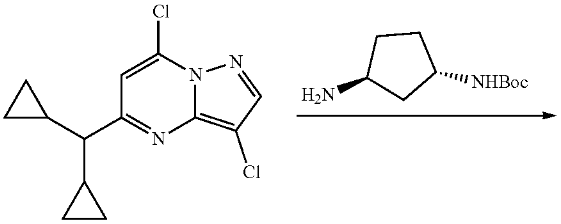

2-1

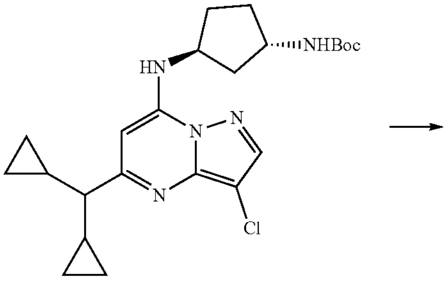

2-2

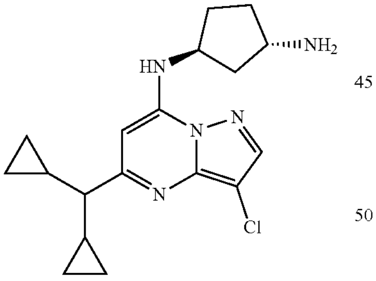

Z-2

Step 1: compound 1-2 (100 mg, 403.68 μmol) was dissolved in acetonitrile (6 mL), added with NCS (53.9 mg, 403.7 μmol), and the mixture was stirred at 20° C. for 2 h. The reaction solution was added with ethyl acetate (100 mL), washed with saturated sodium chloride solution (80 mL×3), and the organic phase was dried over anhydrous sodium sulfate, filtered, and concentrated under reduced pressure. The residue was purified with silica gel column chromatography (20 g, 0~30% ethyl acetate/petroleum ether) to afford compound 2-1 (100 mg, light-yellow oil) in yield of 87.8%. MS m/z (ESI): 282.0 [M+1]

Step 2: with reference to the scheme of step 3 of Example 1, except that compound 1-2 was replaced with compound 2-1, compound 2-2 (120 mg, light-yellow oil) was prepared in yield of 75.9%. MS m/z (ESI): 446.1 [M+1]

Step 3: with reference to the scheme of step 4 of embodiment 1, except that compound 1-3 was replaced with compound 2-2, compound Z-2 (22.3 mg) was prepared in yield of 23.4%. MS m/z (ESI): 346.1 [M+1]; $^1$H NMR (400 MHz, DMSO-d6) δ 8.13 (s, 1H), 7.68 (bs, 1H), 6.12 (s, 1H), 4.28-4.15 (m, 1H), 3.45-3.30 (m, 1H), 2.24-2.13 (m, 1H), 2.13-1.78 (m, 4H), 1.77-1.70 (m, 1H), 1.68-1.58 (m, 1H), 1.37-1.13 (m, 4H), 0.58-0.49 (m, 2H), 0.40-0.18 (m, 4H), 0.12-0.02 (m, 2H).

Example 3: Preparation of Compound Z-3

Z-3

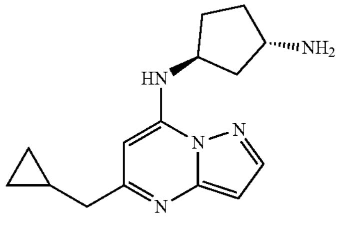

With reference to the preparation scheme of compound Z-1, except that compound V2 was used instead of compound V1, compound Z-3 (33.6 mg) was prepared in yield of 37.7%. MS m/z (ESI): 272.1 [M+1]; $^1$H NMR (400 MHz, DMSO-d6) δ 7.96 (d, J=2.0 Hz, 1H), 6.80 (s, 1H), 6.26 (d, J=2.0 Hz, 1H), 6.08 (s, 1H), 4.19-4.10 (m, 1H), 3.98-3.91 (m, 1H), 2.50 (d, J=7.2 Hz, 2H), 2.17-2.08 (m, 1H), 2.05-1.80 (m, 3H), 1.72-1.62 (m, 1H), 1.50-1.38 (m, 1H), 1.13-1.02 (m, 1H), 0.49-0.40 (m, 2H), 0.26-0.16 (m, 2H).

Example 4: Preparation of Compound Z-4

Z-4

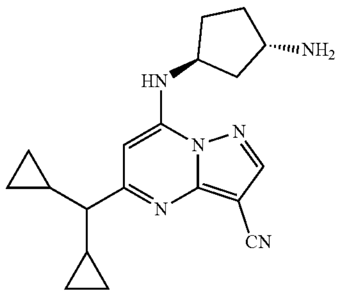

With reference to the preparation scheme of compound Z-1, except that 1H-pyrazole-5-amine was replaced with 3-amino-1H-pyrazole-4-carbonitrile, the compound Z-4 (9.4 mg) was obtained in a yield of 15.2%. MS m/z (ESI): 337.1 [M+1]; $^1$H NMR (400 MHz, DMSO-d6) δ 8.55 (s, 1H), 8.20 (bs, 1H), 6.34 (s, 1H), 4.30-4.20 (m, 1H), 3.45-3.35 (m, 1H), 2.26-2.07 (m, 1H), 2.00-1.82 (m, 2H), 1.79-1.58 (m, 2H), 1.49-1.13 (m, 4H), 0.67-0.44 (m, 2H), 0.43-0.18 (m, 4H), 0.11-0.02 (m, 2H).

Example 5: Preparation of Compound Z-5 and its Stereoisomers Compound Z-5-1, Compound Z-5-2

Z-5

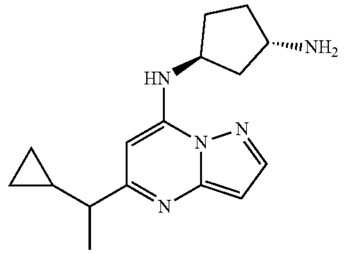

Z-5-1

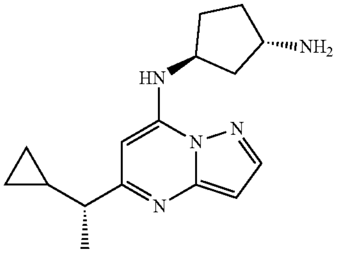

Z-5-2

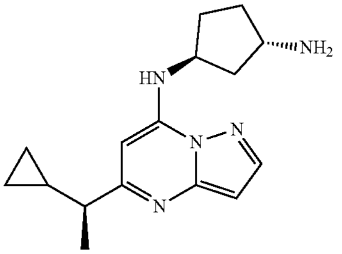

With reference to the preparation scheme of compound Z-1, except that compound V1 was replaced with compound V3, compound Z-5 was prepared (in yield of 41.29%). MS m/z (ESI): 286.1 [M+1]; $^1$H NMR (400 MHz, DMSO-d6) δ 7.96 (d, J=2.2 Hz, 1H), 7.41 (s, 1H), 6.27 (d, J=2.2 Hz, 1H), 6.03 (s, 1H), 4.24-4.16 (m, 1H), 3.43-3.37 (m, 1H), 2.22-2.13 (m, 1H), 2.01-1.82 (m, 3H), 1.78-1.71 (m, 1H), 1.68-1.58 (m, 1H), 1.32-1.22 (m, 4H), 1.06-0.97 (m, 1H), 0.51-0.45 (m, 1H), 0.35-0.30 (m, 1H), 0.22-0.14 (m, 2H).

Compound Z-5 (50 mg) was subjected to chiral resolution (instrument: SFC-150 (Waters); column: IC 20*250 mm, 10 um (Daicel); co-solvents: $CO_2$/IPA [0.5% $NH_3$(7 M in MeOH)]=60/40, wavelength: 214 Nm) to afford two single configuration products Z-5-1 (with retention time: 2.704 min) and Z-5-2 (with retention time: 3.175 min):

Compound Z-5-1 (yield 21.93%), MS m/z (ESI): 286.1 [M+1]; $^1$H NMR (400 MHz, DMSO-d6) δ 8.00 (d, J=2.2 Hz, 1H), 7.49 (d, J=7.6 Hz, 1H), 6.31 (d, J=2.2 Hz, 1H), 6.07 (s, 1H), 4.28-4.19 (m, 1H), 3.49-3.40 (m, 1H), 2.26-2.18 (m, 1H), 2.05-1.87 (m, 3H), 1.82-1.75 (m, 1H), 1.72-1.63 (m, 1H), 1.37-1.23 (m, 4H), 1.11-1.00 (m, 1H), 0.56-0.48 (m, 1H), 0.40-0.31 (m, 1H), 0.27-0.15 (m, 2H);

Compound Z-5-2 (yield 22.62%), MS m/z (ESI): 286.1 [M+1]; $^1$H NMR (400 MHz, DMSO-d6) δ 8.00 (d, J=2.2 Hz, 1H), 7.48 (d, J=7.4 Hz, 1H), 6.31 (d, J=2.2 Hz, 1H), 6.07 (s, 1H), 4.29-4.18 (m, 1H), 3.48-3.40 (m, 1H), 2.25-2.17 (m, 1H), 2.05-1.87 (m, 3H), 1.81-1.75 (m, 1H), 1.70-1.61 (m, 1H), 1.35-1.23 (m, 4H), 1.11-1.01 (m, 1H), 0.55-0.48 (m, 1H), 0.40-0.32 (m, 1H), 0.26-0.17 (m, 2H).

Example 6: Preparation of Compound Z-6

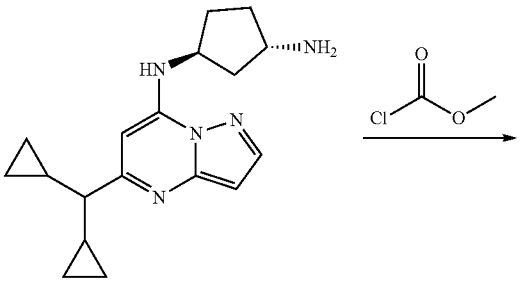

Z-1

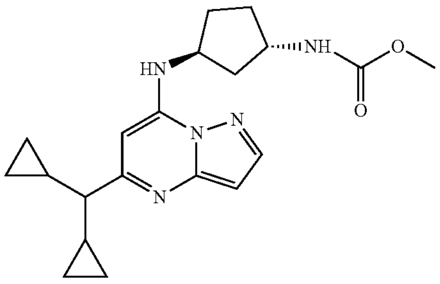

Z-6

Compound Z-1 (60.0 mg, 192.66 μmol) was dissolved in dichloromethane (10 mL), then triethylamine (195.0 mg, 1.93 mmol, 0.27 mL) and methyl chloroformate (91.0 mg, 963.32 μmol) were added thereto, and the mixture was stirred at room temperature for 1 h. Saturated sodium chloride solution (50 mL) was added, followed by extraction with ethyl acetate (60 mL). The organic phase was dried over anhydrous sodium sulfate, filtered, and concentrated under reduced pressure. The residue was subjected to preparative HPLC chromatography to afford compound Z-6 (40.3 mg) in yield of 56.4%. MS m/z (ESI): 370.2 [M+1]; $^1$H NMR (400 MHz, DMSO-d6) δ 7.97 (d, J=2.0 Hz, 1H), 7.57 (d, J=8.0 Hz, 1H), 7.20 (d, J=6.8 Hz, 1H), 6.28 (d, J=2.0 Hz, 1H), 6.01 (s, 1H), 4.18-4.12 (m, 1H), 4.02-3.96 (m, 1H), 3.48 (s, 3H), 2.19-2.08 (m, 1H), 2.06-1.83 (m, 3H), 1.69-1.64 (m, 1H), 1.52-1.36 (m, 1H), 1.29-1.10 (m, 3H), 0.58-0.45 (m, 2H), 0.41-0.14 (m, 4H), 0.13-0.02 (m, 2H).

Example 7: Preparation of Compound Z-7

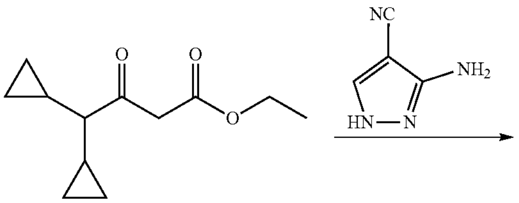

V1

-continued

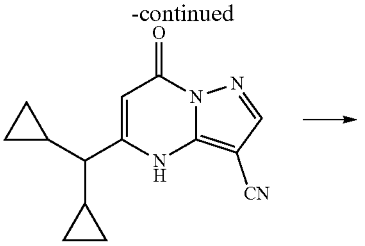

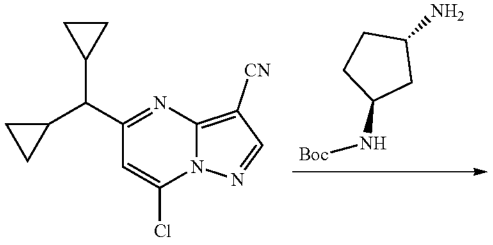

7-1

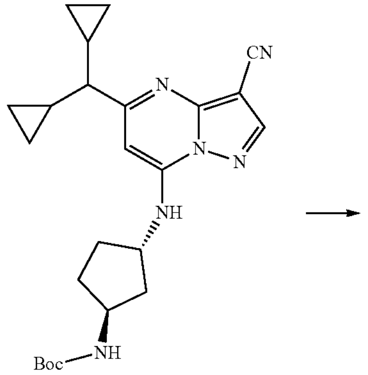

7-2

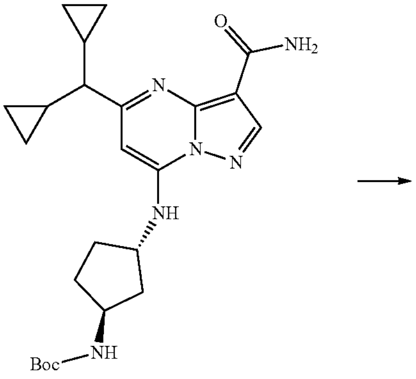

7-3

-continued

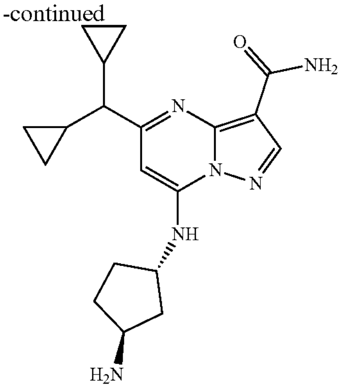

Z-7

Step 1-2: with reference to the scheme of step 1-2 of Example 1, except that 1H-pyrazol-5-amine was replaced with 3-amino-1H-pyrazole-4-carbonitrile, compound 7-1 (light-yellow oil, yield: 46.6%) was prepared, MS m/z (ESI): 273.1 [M+1].

Step 3: compound 7-1 (31 mg, 0.11 mmol), tert-butyl ((1S,3S)-3-aminocyclopentyl)carbamate (22.76 mg, 0.11 mmol), and potassium carbonate (22.76 mg, 0.11 mmol) were dissolved in 3 mL of acetonitrile. The reaction solution was stirred at 60° C. for 3 h. The reaction solution was concentrated under reduced pressure, added with 20 mL of water, and extracted with dichloromethane (20 mL×2). The organic phases were combined, dried over anhydrous sodium sulfate, and concentrated under reduced pressure to afford compound 7-2 (30 mg, yellow oil) in yield of 60.46%. MS m/z (ESI): 437.2 [M+1].

Step 4: compound 7-2 (30 mg, 0.068 mmol) and 5 M of sodium hydroxide solution (0.5 mL) were dissolved in ethanol (1 mL) and dimethylsulfoxide (1 mL). The reaction solution was stirred at 60° C. for 3 h. After completion of the reaction, extraction was performed with dichloromethane (20 mL×2), the organic phases were combined, dried over anhydrous sodium sulfate, and concentrated under reduced pressure to afford compound 7-3 (30 mg, yellow oil) in yield of 91.23%. MS m/z (ESI): 455.2 [M+1].

Step 5: compound 7-3 (30 mg, 0.07 mmol) was dissolved in 3 mL of hydrochloric acid/1,4-dioxane solution and the reaction solution was stirred at room temperature for 2 h. The reaction solution was concentrated under reduced pressure and subjected to preparative HPLC chromatography to afford compound Z-7 (4.57 mg) in yield of 19.46%. MS m/z (ESI): 355.1 [M+1]; $^{1}$H NMR (400 MHz, DMSO-d6) δ 8.34 (s, 1H), 8.10 (s, 1H), 7.77 (s, 1H), 7.27 (s, 1H), 6.28 (s, 1H), 4.35-4.22 (m, 1H), 3.55-3.43 (m, 1H), 2.30-2.18 (m, 1H), 2.10-1.90 (m, 3H), 1.89-1.65 (m, 3H), 1.46-1.24 (m, 4H), 0.62-0.53 (m, 2H), 0.41-0.30 (m, 4H), 0.20-0.08 (m, 2H).

Example 8: Preparation of Compound Z-8

Z-8

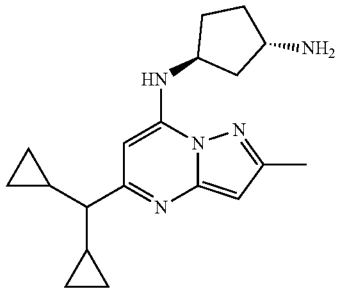

With reference to the preparation scheme of compound Z-1, except that 1H-pyrazol-5-amine was replaced with 5-methyl-1H-pyrazol-3-amine, compound Z-8 was prepared (yield: 33.4%). MS m/z (ESI): 326.2 [M+1]; $^1$H NMR (400 MHz, DMSO-d6) δ 7.23 (s, 1H), 6.07 (s, 1H), 5.95 (s, 1H), 4.24-4.08 (m, 1H), 3.46-3.36 (m, 1H), 2.35 (s, 3H), 2.25-2.10 (m, 1H), 1.99-1.80 (m, 3H), 1.80-1.55 (m, 3H), 1.35-1.12 (m, 4H), 0.56-0.48 (m, 2H), 0.39-0.19 (m, 4H), 0.15-0.02 (m, 2H).

Example 9: Preparation of Compound Z-9

Z-9

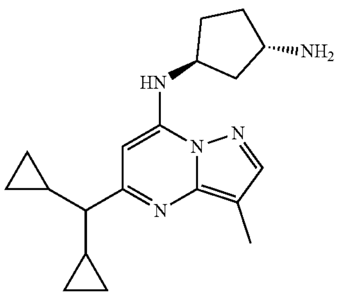

With reference to the preparation scheme of compound Z-1, except that 1H-pyrazol-5-amine was replaced with 4-methyl-1H-pyrazol-3-amine, compound Z-9 was prepared. MS m/z (ESI): 326.2 [M+1]; $^1$H NMR (400 MHz, DMSO-d6) δ 7.83 (s, 1H), 7.30 (d, J=7.6 Hz, 1H), 5.98 (s, 1H), 4.25-4.16 (m, 1H), 3.43-3.35 (m, 1H), 2.24-2.14 (m, 4H), 1.96-1.83 (m, 2H), 1.79-1.57 (m, 4H), 1.33-1.16 (m, 4H), 0.57-0.48 (m, 2H), 0.38-0.22 (m, 4H), 0.13-0.03 (m, 2H).

Example 10: Preparation of Compound Z-10

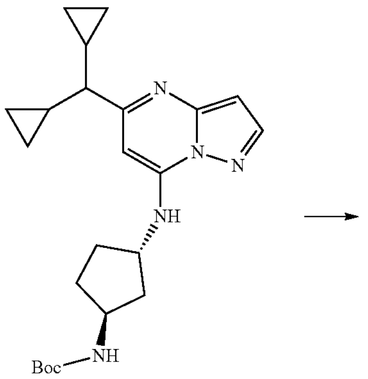

1-3

-continued

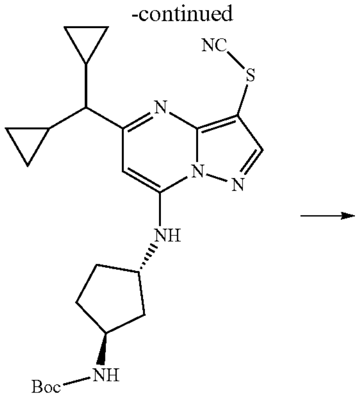

10-1

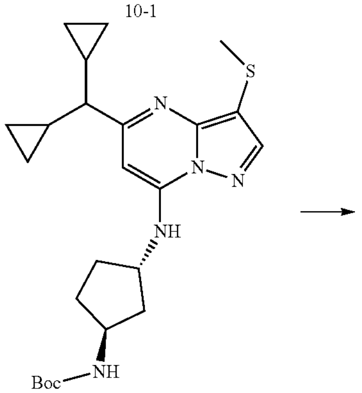

10-2

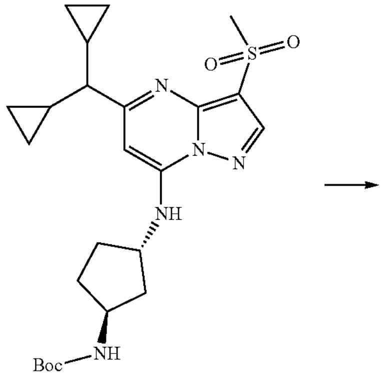

10-3

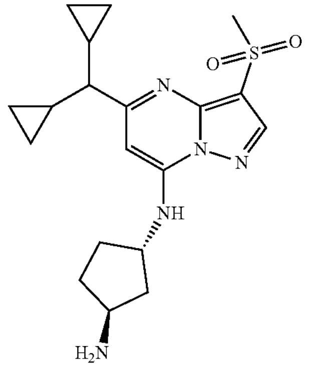

Z-10

Step 1: compound 1-3 (200 mg, 0.485 mmol) and potassium thiocyanate (141.68 mg, 1.46 mmol) were dissolved in methanol (5 mL), and the reaction solution was stirred at room temperature for 3 h. Then, the reaction solution was extracted with dichloromethane (15 mL×2), and the organic phases were combined and dried over anhydrous sodium sulfate, and concentrated under reduced pressure. Separation was performed by column chromatography (PE:EA=4:1) to afford compound 10-1 (169 mg, yellow solid), yield: 74.21%. MS m/z (ESI): 469.2 [M+1].

Step 2: compound 10-1 (169 mg, 0.36 mmol) was dissolved in 3 mL of tetrahydrofuran. 3 M solution of methyl magnesium chloride (0.2 mL) was added at 0° C. The reaction solution was stirred at 0° C. for 2 h, and then acetic acid (43.31 mg, 0.72 mmol) was added. The reaction solution was concentrated under reduced pressure, added with 20 mL of water, and extracted with ethyl acetate (15 mL×3). The organic phases were combined, dried over anhydrous sodium sulfate, and concentrated under reduced pressure to afford compound 10-2 (105 mg, yellow solid) in yield of 63.62%, MS m/z (ESI): 458.2 [M+1].

Step 3: compound 10-2 (105 mg, 0.229 mmol) was dissolved in dichloromethane (3 mL). M-chloroperoxybenzoic acid (73.31 mg, 0.482 mmol) was added under stirring. The reaction solution was stirred at room temperature for 2 h. After the reaction was completed, the reaction solution was extracted with ethyl acetate (15 mL×3), and the organic phases were combined, dried over anhydrous sodium sulfate, and concentrated under reduced pressure. Separation was performed by column chromatography (PE:EA=4:1) to afford compound 10-3 (83 mg, light-yellow solid) in yield of 79.44%. MS m/z (ESI): 490.2 [M+1].

Step 4: compound 10-3 (83 mg, 0.17 mmol) was dissolved in 3 mL of hydrochloric acid/1,4-dioxane solution and the reaction solution was stirred at room temperature for 3 h. The reaction solution was concentrated under reduced pressure and subjected to preparative HPLC chromatography to afford compound Z-10 (24.27 mg) in yield of 33.45%. MS m/z (ESI): 390.1 [M+1]; $^1$H NMR (400 MHz, DMSO-d6) δ 8.37 (s, 1H), 6.85 (s, 1H), 6.43 (s, 1H), 6.05 (s, 2H), 4.31-4.21 (m, 1H), 4.00-4.92 (m, 1H), 3.28 (s, 3H), 2.25-2.09 (m, 1H), 2.06-1.87 (m, 3H), 1.78-1.66 (m, 1H), 1.51-1.34 (m, 2H), 1.29-1.17 (m, 2H), 0.62-0.50 (m, 2H), 0.45-0.25 (m, 4H), 0.16-0.06 (m, 2H).

Example 11: Preparation of Compound Z-11

Z-11

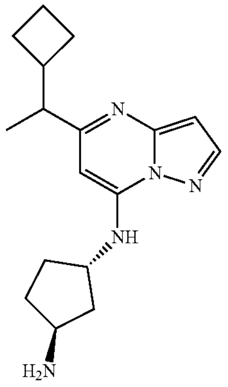

With reference to the preparation of compound Z-1, except that intermediate V1 was replaced with intermediate V5, compound Z-11 was prepared. MS m/z (ESI): 300.2 [M+1]; $^1$H NMR (400 MHz, DMSO-d6) δ 7.97 (s, 1H), 7.54 (s, 1H), 6.28 (s, 1H), 5.99 (s, 1H), 4.13-4.22 (m, 1H), 3.90-3.99 (m, 1H), 2.75-2.6.3 (m, 1H), 2.51-2.57 (m, 1H), 2.20-1.96 (m, 3H), 1.85-1.94 (m, 2H), 1.60-1.78 (m, 6H), 1.40-1.49 (m, 1H), 1.11 (d, J=6.8 Hz, 3H).

Example 11a: Preparation of Compound Z-11-P1

Z-11-P1

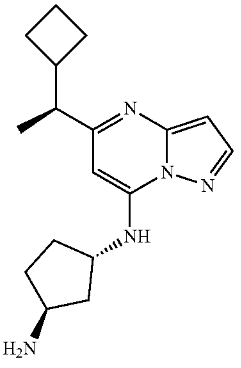

Compound Z-11 (94.46 mg, 315.48 μmol) was subjected to chiral resolution (column type: IC-3 4.6*100 mm 3 μm; co-solvent: IPA [1% $NH_3$(7 M in MeOH)]; injection volume: 5.00 μl; wavelength: 220.0 nm; run time: 6.0 minutes; flow rate: 3.0 mL/min; pressure: 2000 psi; column temperature: 40° C.) to afford compound Z-11-P1 (9.70 mg, retention time 2.471 min), yield: 9.89%, purity: 96.34%. MS m/z (ESI): 300.2[M+H$^+$]. $^1$H NMR (400 MHz, DMSO-d6) δ 7.96 (d, J=2.0 Hz, 1H), 7.41 (d, J=7.6 Hz, 1H), 6.27 (d, J=2.0 Hz, 1H), 5.96 (s, 1H), 4.21 (q, J=7.2 Hz, 1H), 3.42 (q, J=6.0 Hz, 1H), 2.65-2.74 (m, 1H), 2.58-2.50 (m, 1H), 2.16-2.24 (m, 1H), 2.03-2.09 (m, 1H), 1.83-1.95 (m, 2H), 1.80-1.61 (m, 7H), 1.35-1.25 (m, 1H), 1.11 (d, J=6.8 Hz, 3H).

Example 11b: Preparation of Compound Z-11-P2

Z-11-P2

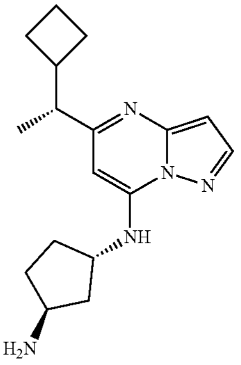

Compound Z-11 (94.46 mg, 315.48 μmol) was subjected to chiral resolution (column type: IC-3 4.6*100 mm 3 μm; co-solvent: IPA [1% $NH_3$(7 M in MeOH)]; injection volume: 5.00 μl; wavelength: 220.0 nm; run time: 6.0 minutes; flow rate: 3.0 mL/min; pressure: 2000 psi; column temperature: 40° C.) to afford compound Z-11-P2 (9.37 mg, retention time 2.012 min), yield: 9.55%, purity: 96.24%. MS m/z (ESI): 300.2[M+H$^+$]. $^1$H NMR (400 MHz, DMSO-d6) δ

7.96 (d, J=2.0 Hz, 1H), 7.42 (d, J=7.6 Hz, 1H), 6.27 (d, J=2.0 Hz, 1H), 5.96 (s, 1H), 4.21 (q, J=7.2 Hz, 1H), 3.44-3.37 (m, 1H), 2.65-2.74 (m, 1H), 2.58-2.50 (m, 1H), 2.15-2.25 (m, 1H), 2.02-2.08 (m, 1H), 1.82-1.95 (m, 2H), 1.79-1.60 (m, 7H), 1.35-1.24 (m, 1H), 1.10 (d, J=6.8 Hz, 3H).

Examples 12: Preparation of Compound Z-12

Z-12

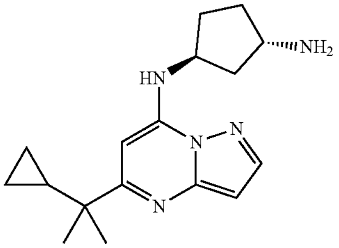

With reference to the preparation of compound Z-1, except that intermediate V1 was replaced with intermediate V7, compound Z-12 was prepared. MS m/z (ESI): 300.2 [M+1]; $^1$H NMR (400 MHz, DMSO-d6) δ 8.01 (d, J=2.0 Hz, 1H), 7.43 (d, J=6.0 Hz, 1H), 6.34 (d, J=2.0 Hz, 1H), 6.23 (s, 1H), 4.30-4.18 (m, 1H), 3.46-3.40 (m, 1H), 2.26-2.18 (m, 1H), 1.99-1.86 (m, 2H), 1.83-1.74 (m, 1H), 1.73-1.64 (m, 1H), 1.37-1.27 (m, 1H), 1.17 (s, 6H), 1.15-1.11 (m, 1H), 0.39-0.34 (m, 4H).

Examples 13: Preparation of Compound Z-13

Z-13

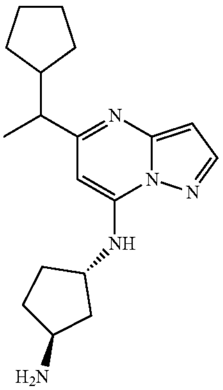

With reference to the preparation of compound Z-1, except that intermediate V1 was replaced with intermediate V6, compound Z-13 was prepared. MS m/z (ESI): 314.2 [M+1]; $^1$H NMR (400 MHz, DMSO-d6) δ 7.99 (d, J=2.4 Hz, 1H), 7.50 (d, J=38.8 Hz, 1H), 6.30 (d, J=2.4 Hz, 1H), 6.02 (d, J=8.0 Hz, 1H), 4.23 (s, 1H), 3.50-3.38 (m, 1H), 2.52-2.55 (m, 1H), 2.07-2.25 (m, 2H), 1.99-1.77 (m, 4H), 1.71-1.29 (m, 7H), 1.26-1.16 (m, 4H), 1.12-1.01 (m, 1H).

Examples 14: Preparation of Compound Z-14

Z-14

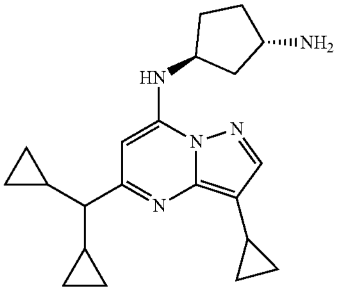

With reference to the preparation scheme of compound Z-1, except that 1H-pyrazol-5-amine was replaced with 4-cyclopropyl-1H-pyrazol-3-amine, compound Z-14 was prepared. MS m/z (ESI): 352.2 [M+1]; $^1$H NMR (400 MHz, DMSO-d6) δ 7.74 (s, 1H), 7.29 (d, J=7.2 Hz, 1H), 5.98 (s, 1H), 4.24-4.12 (m, 1H), 3.45-3.36 (m, 1H), 2.27-1.79 (m, 6H), 1.76-1.70 (m, 1H), 1.67-1.56 (m, 1H), 1.35-1.14 (m, 4H), 0.89-0.71 (m, 4H), 0.57-0.48 (m, 2H), 0.39-0.20 (m, 4H), 0.15-0.06 (m, 2H).

Example 15: Preparation of Compound Z-15

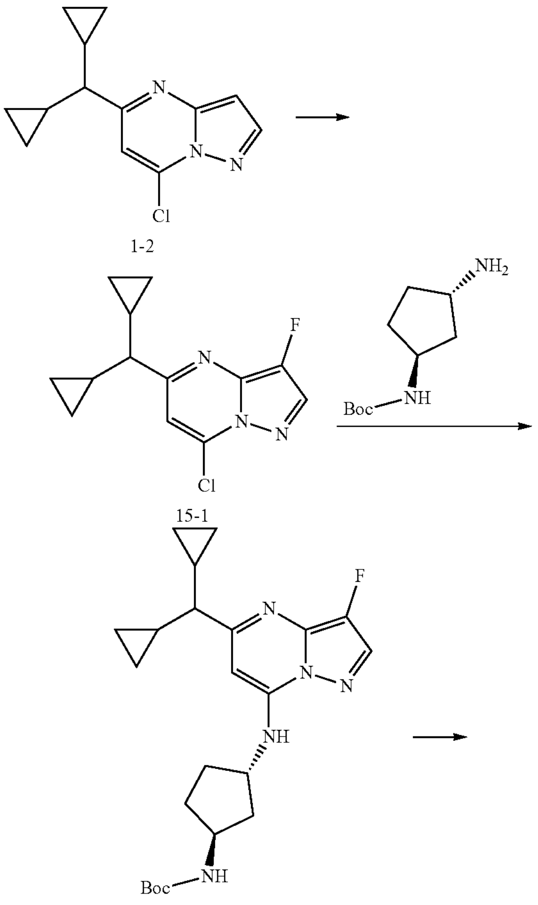

1-2

15-1

15-2

-continued

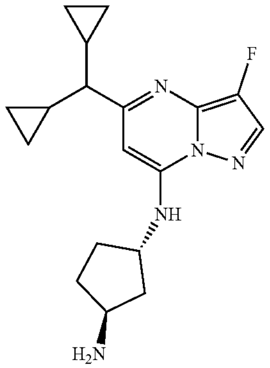

Z-15

Step 1: compound 1-2 (145 mg, 0.585 mmol) and acetic acid (70.24 mg, 1.17 mmol) were dissolved in acetonitrile (5 mL), and after adding Selectfluor reagent (207.36 mg, 0.584 mmol) under stirring, the mixture was stirred at 70° C. for 4 h. Then, the reaction solution was extracted with ethyl acetate (15 mL×2), and the organic phases were combined, dried over anhydrous sodium sulfate, and concentrated under reduced pressure. Separation was performed by column chromatography (PE:EA=4:1) to afford compound 15-1 (45 mg, yellow liquid), yield: 28.93%. MS m/z (ESI): 266.0 [M+1].

Step 2-3: With reference to the preparation scheme of step 3 and step 4 of compound Z-1, except that compound 1-2 was replaced with compound 15-1, compound Z-15 was prepared. MS m/z (ESI): 330.3 [M+1]; $^1$H NMR (400 MHz, DMSO-d6) δ 8.16 (d, J=3.6 Hz, 1H), 7.65 (s, 1H), 6.08 (s, 1H), 4.30-4.15 (m, 1H), 3.48-3.42 (m, 1H), 2.26-2.15 (m, 1H), 2.00-1.85 (m, 2H), 1.82-1.76 (m, 1H), 1.72-1.60 (m, 1H), 1.36-1.16 (m, 4H), 0.61-0.50 (m, 2H), 0.39-0.25 (m, 4H), 0.15-0.05 (m, 2H).

Example 16: Preparation of Compound Z-16

Z-16

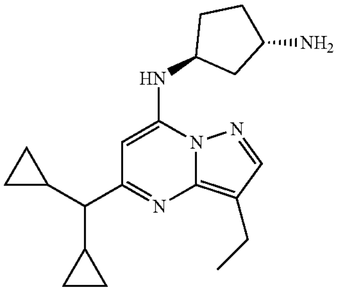

With reference to the preparation scheme of compound Z-1, except that 1H-pyrazol-5-amine was replaced with 4-ethyl-1H-pyrazol-3-amine, compound Z-16 was prepared. MS m/z (ESI): 340.2 [M+1]; $^1$H NMR (400 MHz, DMSO-d6) δ 7.86 (s, 1H), 7.30 (d, J=7.6 Hz, 1H), 5.99 (s, 1H), 4.25-4.15 (m, 1H), 3.37-3.45 (m, 1H), 2.63 (q, J=7.6 Hz, 2H), 2.14-2.23 (m, 1H), 1.98-1.81 (m, 2H), 1.71-1.79 (m, 2H), 1.69-1.56 (m, 1H), 1.35-1.17 (m, 6H), 0.47-0.56 (m, 2H), 0.23-0.34 (m, 4H), 0.15-0.03 (m, 2H).

Example 17: Preparation of Compound Z-17

Z-17

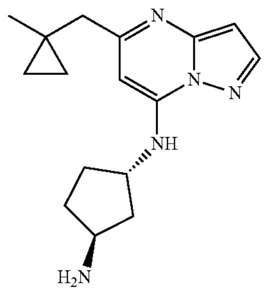

With reference to the preparation scheme of compound Z-1, except that compound V1 was replaced with compound V9, compound Z-17 was prepared. MS m/z (ESI): 286.2 [M+1]; $^1$H NMR (400 MHz, DMSO-d6) δ 8.01 (d, J=2.4 Hz, 1H), 7.64 (s, 1H), 6.90 (d, J=6.4 Hz, 1H), 6.32 (d, J=2.4 Hz, 1H), 6.07 (s, 2H), 4.15-4.12 (m, 1H), 4.03-3.91 (m, 1H), 2.57 (s, 2H), 2.25-2.10 (s, 1H), 2.06-1.85 (m, 3H), 1.76-1.63 (m, 1H), 1.53-1.40 (m, 1H), 1.02 (s, 3H), 0.56 (s, 2H), 0.31 (s, 2H).

Example 18: Preparation of Compound Z-18

Z-18

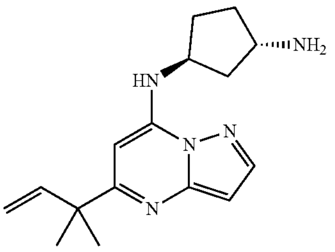

With reference to the preparation scheme of compound Z-1, except that compound V1 was replaced with compound V4, compound Z-18 was prepared (in yield of 25.40%). MS m/z (ESI): 286.1 [M+1]; $^1$H NMR (400 MHz, DMSO-d6) δ 8.03 (d, J=2.2 Hz, 1H), 7.61 & 6.89 (s, 1H), 6.37 (d, J=2.2 Hz, 1H), 6.17 (dd, J=17.2, 10.6 Hz, 1H), 6.04 (s, 1H), 5.11 (dd, J=17.6, 1.2 Hz, 1H), 5.07 (dd, J=10.6, 1.2 Hz, 1H), 4.22-4.14 (m, 1H), 4.00-3.93 (m, 1H), 2.20-2.07 (m, 1H), 2.03-1.86 (m, 3H), 1.74-1.62 (m, 1H), 1.53-1.41 (m, 1H), 1.41 (s, 6H).

Example 19: Preparation of Compound Z-19

Z-19

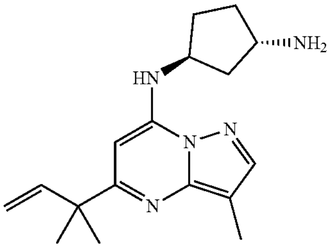

With reference to the preparation scheme of compound Z-1, except that compound V1 was replaced with compound V4 and 1H-pyrazol-5-amine was replaced with 4-methyl-1H-pyrazol-3-amine, compound Z-19 was prepared. MS m/z (ESI): 300.2 [M+1]; $^1$H NMR (400 MHz, DMSO-d6) δ 7.86 (s, 1H), 7.46-7.34 (m, 1H), 6.17 (dd, J=17.6, 10.4 Hz, 1H), 5.94 (d, J=6.0 Hz, 1H), 5.07 (dd, J=21.0, 14.0 Hz, 2H), 4.19-4.12 (m, 1H), 3.43-3.37 (m, 1H), 2.92 (bs, 2H), 2.18 (s, 3H), 2.21-1.96 (m, 1H), 1.94-1.82 (m, 2H), 1.77-1.66 (m, 1H), 1.67-1.59 (m, 1H), 1.49-1.24 (m, 7H).

Example 20 to Example 25

Compounds Z-20 to Z-25 was prepared with reference to the schemes of Example 1.

| Example No. | Structure | $^1$H NMR and MS |
|---|---|---|
| 20 | 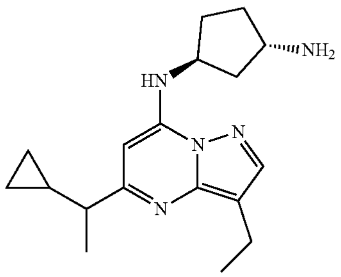 Z-20 | MS m/z (ESI): 314.3 [M + 1]. $^1$H NMR (400 MHz, DMSO-d6) δ 7.88 (s, 1H), 7.34 (s, 1H), 6.02 (s, 1H), 4.23-4.15 (m, 1H), 3.60-3.31 (m, 1H), 2.65 (q, J = 7.6 Hz, 2H), 2.26-2.16 (m, 1H), 2.08-1.83 (m, 3H), 1.83-1.60 (m, 2H), 1.40-1.28 (m, 4H), 1.24 (t, J = 7.6 Hz, 3H), 1.12-1.00 (m, 1H), 0.57-0.46 (m, 1H), 0.42-0.32 (m, 1H), 0.26-0.16 (m, 2H). |
| 21 | 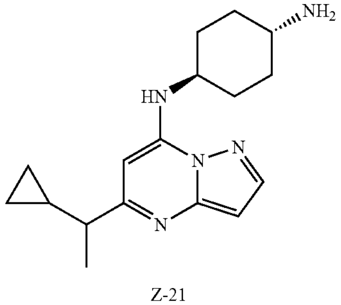 [SMILES: CC(c1cc(N[C@H]2CC[C@H](N)CC2)n2nccc2n1)C1CC1] Z-21 | MS m/z (ESI): 300.3 [M + 1] $^1$H NMR (400 MHz, DMSO-d6) δ 7.97 (d, J = 2.4 Hz, 1H), 7.25 (s, 1H), 6.28 (d, J = 2.4 Hz, 1H), 6.12 (s, 1H), 3.60-3.47 (m, 1H), 2.60-2.50 (s, 1H), 2.03-1.94 (m, 1H), 1.93-1.85 (m, 2H), 1.83-1.73 (m, 2H), 1.60-1.44 (m, 2H), 1.29 (d, J = 6.8 Hz, 3H), 1.25-1.11 (m, 2H), 1.10-1.00 (m, 1H), 0.53-0.46 (m, 1H), 0.36-0.28 (m, 1H), 0.24-0.13 (m, 2H). |
| 22 | 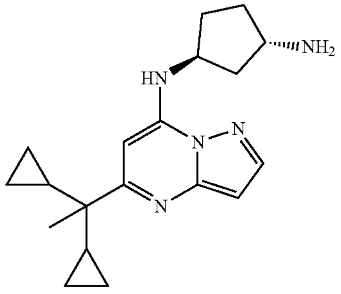 Z-22 | MS m/z (ESI): 326.2 [M + 1] $^1$H NMR (400 MHz, DMSO-d6) δ 7.99 (d, J = 2.4 Hz, 1H), 7.44 (s, 1H), 6.35-6.30 (m, 2H), 4.27-4.17 (m, 1H), 3.50-3.43 (m, 1H), 2.27-2.15 (m, 1H), 2.02-1.88 (m, 2H), 1.86-1.76 (m, 1H), 1.75-1.63 (m, 1H), 1.40-1.30 (m, 1H), 1.12-0.97 (m, 5H), 0.51-0.43 (m, 2H), 0.42-0.33 (m, 2H), 0.32-0.20 (m, 4H). |

-continued
| Example No. | Structure | $^1$H NMR and MS |
|---|---|---|
| 23 | 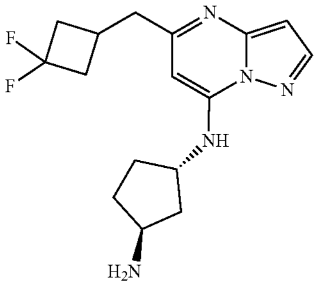 Z-23 | MS m/z (ESI): 322.1 [M + 1] $^1$H NMR (400 MHz, DMSO-d6) δ 7.98 (d, J = 2.0 Hz, 1H), 7.53 (s, 1H), 6.28 (d, J = 2.4 Hz, 1H), 6.06 (d, J = 5.2 Hz, 1H), 4.26-4.10 (m, 1H), 3.46-3.36(m, 1H), 2.83 (d, J = 7.2 Hz, 2H), 2.73-2.52 (m, 3H), 2.42-2.26 (m, 2H), 2.25-2.06 (m, 1H), 2.03-1.82 (m, 2H), 1.80-1.57(m, 2H), 1.35-1.22 (m, 1H). |
| 24 | 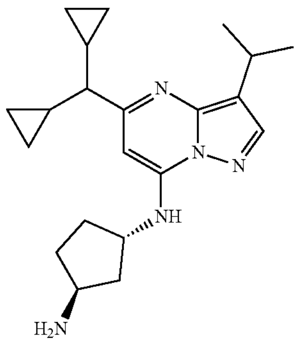 Z-24 | MS m/z (ESI): 354.2 [M + 1] $^1$H NMR (400 MHz, DMSO-d6) δ 7.83 (s, 1H), 7.30 (d, J = 7.2 Hz, 1H), 6.00 (s, 1H), 4.19 (d, J = 7.2 Hz, 1H), 3.47-3.36 (m, 1H), 3.18-3.01 (m, 1H), 2.25-2.14 (m, 1H), 1.98-1.80 (m, 2H), 1.80-1.56 (m, 4H), 1.36-1.16 (m, 10H), 0.57-0.47 (m, 2H), 0.37-0.23 (m, 4H), 0.14-0.05 (m, 2H). |
| 25 | 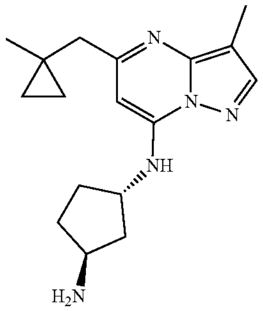 Z-25 | MS m/z (ESI): 300.2 [M + 1] $^1$H NMR (400 MHz, DMSO-d6) δ 7.83 (s, 1H), 7.30 (d, J = 7.2 Hz, 1H), 5.98 (s, 1H), 4.23-4.10 (m, 1H), 3.47-3.35 (m, 1H), 2.57 (s, 2H), 2.26-2.10 (m, 4H), 1.95-1.83 (m, 2H), 1.81-1.54 (m, 2H), 1.34-1.22 (m, 1H), 1.03 (s, 3H), 0.54 (t, J = 4.8 Hz, 2H), 0.30 (t, J =4.8 Hz, 2H). |
Example 26: Preparation of Compound Z-26
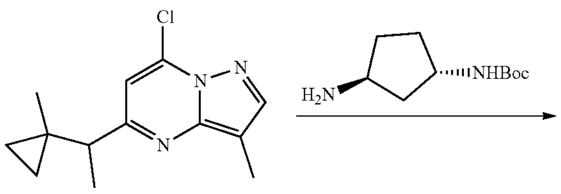
22-2
-continued
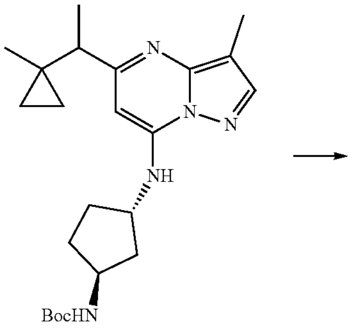
Z-26-1

-continued

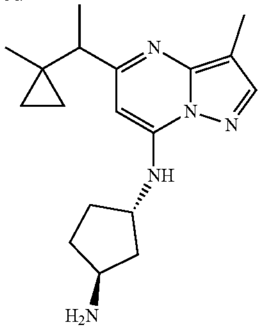

Z-26

Compound Z-26 was prepared using compound 22-2 as starting material with reference to schemes of step 3 and step 4 of Example 1. MS m/z (ESI): 314.1 [M+1]. $^1$H NMR (400 MHz, DMSO-d6) δ 7.85 (s, 1H), 7.28 (d, J=6.0 Hz, 1H), 5.97 (s, 1H), 4.26-4.12 (m, 1H), 3.50-3.38 (m, 1H), 2.35-2.27 (m, 1H), 2.25-2.10 (m, 5H), 1.97-1.86 (m, 2H), 1.83-1.72 (m, 1H), 1.72-1.56 (m, 2H), 1.34 (d, J=7.2 Hz, 1H), 1.29 (d, J=7.2 Hz, 3H), 0.96 (s, 3H), 0.75-0.66 (m, 1H), 0.48-0.38 (m, 1H), 0.23-0.18 (m, 2H).

Example 26a: Preparation of Compound Z-26-P1

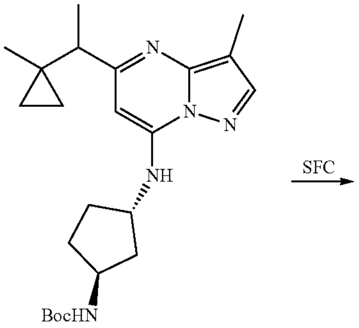

Z-26-1

-continued

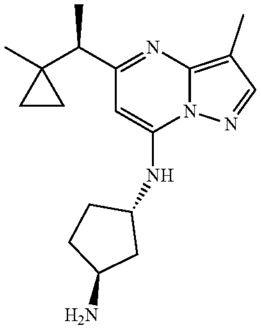

Z-26-P1

Step 1: compound Z-26-1 (650 mg) was resolved by means of supercritical fluid chromatography (SFC) (column type: IC-3 4.6*100 mm 3 μm, co-solvent: IPA/ACN=1/1 [0.1% DEA], flow rate: 3.0 mL/min, column temperature: 40° C.) to obtain 212 mg of compound Z-26-a (retention time: 2.468 minutes).

Step 2: compound Z-26-a (212 mg, 512.63 μmol) was dissolved in hydrochloric acid/dioxane (4 M) (10 mL), and the mixture reacted for 2 h at room temperature. The reaction solution was dried by means of a rotary dryer. The residue was dissolved in ethyl acetate (20 mL), washed with saturated sodium bicarbonate twice, dried over anhydrous sodium sulfate, filtered, and dried by means of a rotary dryer. The residue was purified with preparative liquid chromatography (preparative column: 21.2×250 mm C18 column; system: 10 mM of $NH_4HCO_3H_2O$; wavelength: 254/214 nm; gradient: 5%-95% acetonitrile change) to afford 60.12 mg of compound Z-26-P1 in yield of 36.79%. MS m/z (ESI): 314.1 [M+1]. $^1$H NMR (400 MHz, DMSO-d6) δ 7.83 (s, 1H), 7.36 (s, 1H). 5.96 (s, 1H), 4.25-4.05 (m, 1H), 3.50-3.38 (m, 1H), 2.35-2.25 (m, 1H), 2.25-2.07 (m, 4H), 2.05-1.80 (m, 3H), 1.75-1.60 (m, 1H), 1.53-1.40 (m, 1H), 1.27 (d, J=7.2 Hz, 3H), 0.94 (s, 3H), 0.74-0.64 (m, 1H), 0.44-0.37 (m, 1H), 0.31-0.19 (m, 2H).

Example 26b: Preparation of Compound Z-26-P2

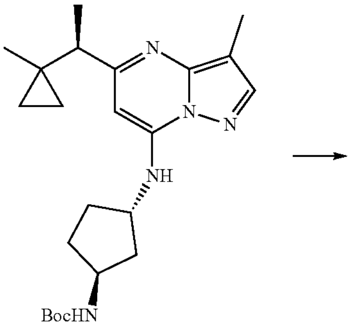

Z-26-a

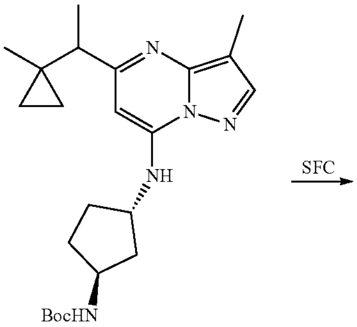

Z-26-1

-continued

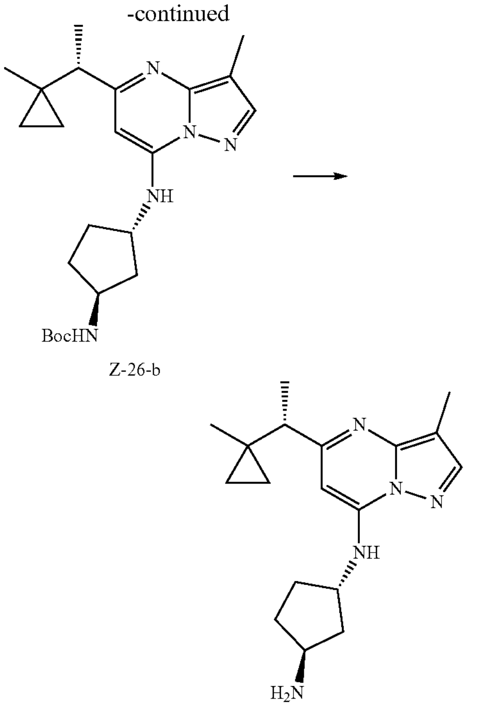

Z-26-b

Z-26-P2

Step 1: compound Z-26-1 (650 mg) was resolved by supercritical fluid chromatography (SFC) (method: column type: IC-3 4.6*100 mm 3 μm, co-solvent: IPA/ACN=1/1 [0.1% DEA] flow rate: 3.0 mL/min, column temperature: 40° C.) to obtain 120 mg of compound Z-26-b (retention time: 2.976 minutes).

Step 2: compound Z-26-b (120 mg, 290.17 μmol) was dissolved in hydrochloric acid/dioxane (4 M) (10 mL). The reaction was allowed to proceed for 2 h at room temperature. The reaction solution was dried by means of a rotary dryer, the residue was dissolved in ethyl acetate (20 mL), washed with saturated sodium bicarbonate twice, dried over anhydrous sodium sulfate, filtered and dried by means of a rotary dryer. The residue was purified with preparative liquid chromatography (preparative column: 21.2×250 mm C18 column; system: 10 mM of $NH_4HCO_3H_2O$; wavelength: 254/214 nm; gradient: 5%-95% acetonitrile change) to afford 34.2 mg of compound Z-26-P2 in yield of 36.96%. MS m/z (ESI): 314.1 [M+1]. $^1$H NMR (400 MHz, DMSO-d6) δ 7.83 (s, 1H), 7.24 (d, J=7.2 Hz, 1H), 5.96 (s, 1H), 4.23-4.13 (m, 1H), 3.47-3.37 (m, 1H), 2.35-2.25 (m, 1H), 2.25-2.10 (m, 4H), 2.00-1.82 (m, 2H), 1.81-1.72 (m, 1H), 1.70-1.57 (m, 1H), 1.37-1.23 (m, 4H), 0.94 (s, 3H), 0.73-0.64 (m, 1H), 0.45-0.37 (m, 1H), 0.34-0.19 (m, 2H).

Example 27 to Example 30

Compounds Z-27 to Z-30 was prepared with reference to the schemes of Example 1.

| Example No. | Structure | $^1$H NMR and MS |
|---|---|---|
| 27 | 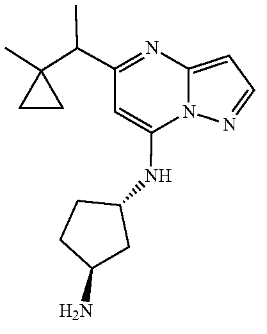 Z-27 | MS m/z (ESI): 300.3 [M + 1] 1H NMR (400 MHz, DMSO-d6) δ 7.98 (d, J = 2.0 Hz, 1H), 7.41 (d, J =8.0 Hz, 1H), 6.32 (d, J = 2.0 Hz, 1H), 6.02 (s, 1H), 4.26-4.10 (m, 1H), 3.52-3.40 (m, 1H), 2.32-2.08 (m, 3H), 2.03-1.81 (m, 3H), 1.80-1.55 (m, 2H), 1.36-1.23 (m, 4H), 0.91 (s, 3H), 0.74-0.66 (m, 1H), 0.43-0.37 (m, 1H), 0.32-0.20 (m, 2H). |
| 28 | 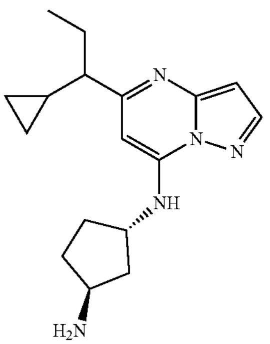 Z-28 | MS m/z (ESI): 300.2 [M + 1] 1H NMR (400 MHz, DMSO-d6) δ 7.99 (s, 1H), 7.52 (s, 1H), 6.29 (d, J = 2.0 Hz, 1H), 6.02 (d, J = 8.4 Hz, 1H), 4.27-4.13 (m, 1H), 3.55-3.40 (m, 1H), 2.27-2.06 (m, 1H), 2.06-1.79 (m, 3H), 1.80-1.60 (m, 3H), 1.52-1.38 (m, 1H), 1.36-1.24 (m, 1H), 1.09-0.96 (m, 1H), 0.80 (t, J = 7.2 Hz, 3H), 0.58-0.48 (m, 1H), 0.33-0.17 (m, 2H), 0.15-0.06 (m, 1H). |

-continued
| Example No. | Structure | $^1$H NMR and MS |
|---|---|---|
| 29 | 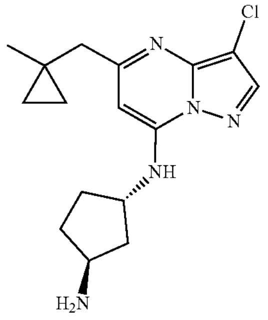 Z-29 | MS m/z (ESI): 320.2 [M + 1] 1H NMR (400 MHz, DMSO-d6) δ 8.16 (s, 1H), 7.78 (s, 1H), 6.14 (d, J = 3.6 Hz, 1H), 4.24-4.07 (m, 1H), 3.55-3.40 (m, 1H), 2.62 (s, 2H), 2.27-2.07 (m, 1H), 2.07-1.64 (m, 5H), 1.53-1.25 (m, 2H), 1.03 (s, 3H), 0.63-0.55 (m, 2H), 0.38-0.27 (m, 2H). |
| 30 | 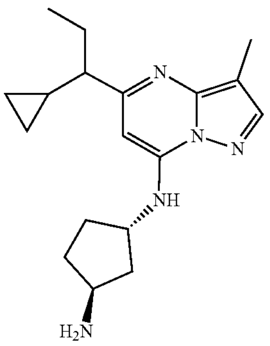 Z-30 | MS m/z (ESI): 314.2 [M + 1] 1H NMR (400 MHz, DMSO-d6) δ 7.85 (s, 1H), 7.36 (d, J = 7.2 Hz, 1H), 5.99 (d, J = 7.6 Hz, 1H), 4.23-4.20 (m, 1H), 3.55-3.40 (m, 1H), 2.30-2.10 (m, 4H), 2.08-1.55 (m, 7H), 1.40-1.25 (m, 1H), 1.12-0.98 (m, 1H), 0.83 (t, J = 7.2 Hz, 3H), 0.60-0.50 (m, 1H), 0.35-0.19 (m, 2H), 0.16-0.07 (m, 1H). |
Example 27a: Preparation of Compound Z-27-P1
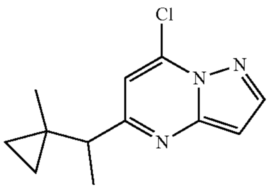
51-2
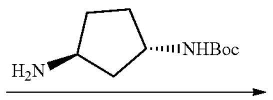
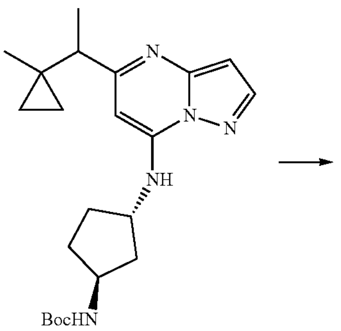
Z-27-1
-continued
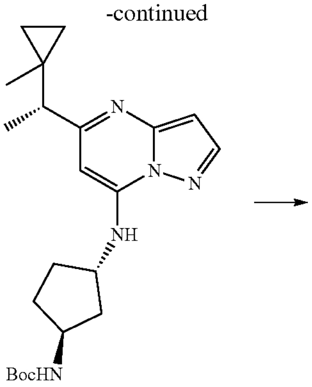
Z-27-a
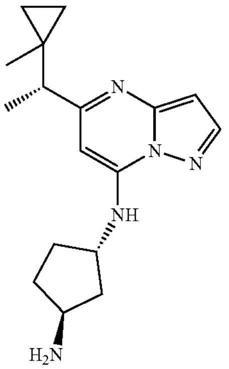
Z-27-P1

Step 1: compound Z-27-1 was prepared using compound 51-2 as starting material with reference to the scheme of step 3 of Example 1. MS m/z (ESI): 400.2 [M+1].

Step 2: 410 mg of the compound Z-27-1 was resolved by supercritical fluid chromatography (SFC) (column type: IG 4.6*100 mm 5 μm, co-solvent: MeOH [0.2% $NH_3$(7 M in MeOH)], injection volume: 5.00 μl, run time: 4.0 minutes, flow rate: 3.0 mL/min, pressure: 2000 psi, column temperature: 40° C.) to obtain 160 mg of compound Z-27-a (retention time 1.954 minutes).

Step 3: compound Z-27-P1 was prepared with reference to step 2 of Example 26a. MS m/z (ESI): 300.2 [M+1]. $^1H$ NMR (400 MHz, DMSO-d6) δ 8.00 (d, J=2.4 Hz, 1H), 7.44 (s, 1H), 6.35 (d, J=2.0 Hz, 1H), 6.05 (s, 1H), 4.28-4.15 (m, 1H), 3.49-3.38 (m, 1H), 2.38-2.10 (m, 2H), 2.05-1.88 (m, 2H), 1.87-1.61 (m, 2H), 1.55-1.22 (m, 4H), 0.94 (s, 3H), 0.75-0.64 (m, 1H), 0.47-0.38 (m, 1H), 0.34-0.13 (m, 2H).

Example 27b: Preparation of Compound Z-27-P2

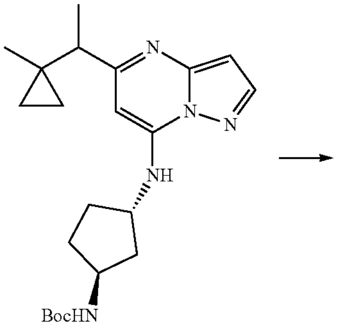

Z-27-1

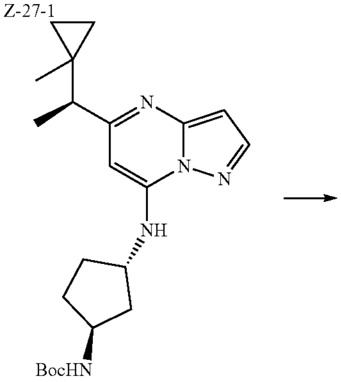

Z-27-b

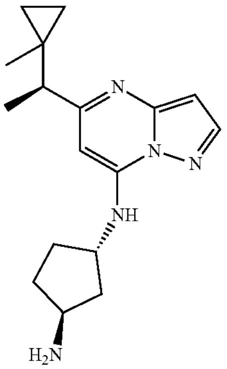

Z-27-P2

Step 1: 410 mg of the compound Z-27-1 was resolved by supercritical fluid chromatography (SFC) (column type: IG 4.6*100 mm 5 μm, co-solvent: MeOH [0.2% $NH_3$(7 M in MeOH)], injection volume: 1.00 μl, run time: 4.0 minutes, flow rate: 3.0 mL/min, pressure: 2000 psi, column temperature: 40° C.) to obtain 120 mg of compound Z-27-b (retention time 2.336 minutes).

Step 2: compound Z-27-P2 was prepared with reference to step 2 of Example 26a. MS m/z (ESI): 300.2 [M+1]. $^1H$ NMR (400 MHz, DMSO-d6) δ 8.00 (d, J=2.4 Hz, 1H), 7.45 (s, 1H), 6.35 (d, J=2.0 Hz, 1H), 6.04 (s, 1H), 4.27-4.15 (m, 1H), 3.50-3.40 (m, 1H), 2.37-2.11 (m, 2H), 2.05-1.87 (m, 2H), 1.84-1.55 (m, 2H), 1.54-1.19 (m, 4H), 0.94 (s, 3H), 0.77-0.59 (m, 1H), 0.47-0.39 (m, 1H), 0.35-0.22 (m, 2H).

Example 28a: Preparation of Compound Z-28-P1

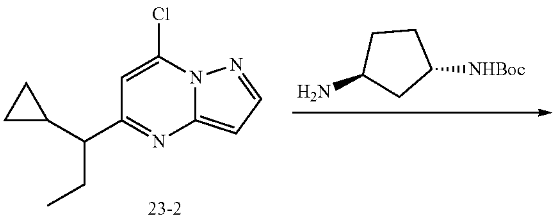

23-2

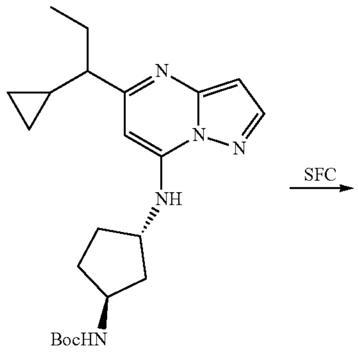

Z-28-1

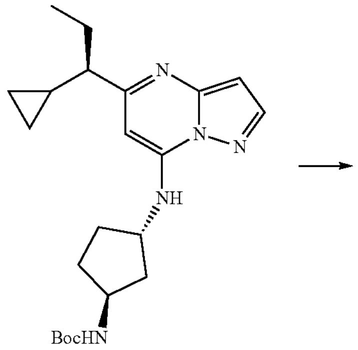

Z-28-a

-continued

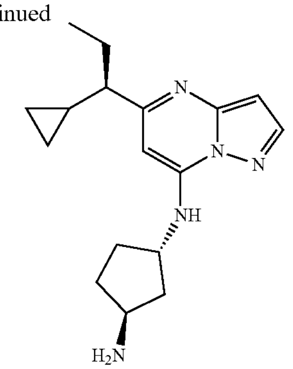

Z-28-P1

Step 1: compound 23-2 (5 g, 21.21 mmol) was dissolved in acetonitrile (30 mL), and tert-butyl ((1S,3S)-3-aminocyclopentyl)carbamate (5.10 g, 25.45 mmol) and potassium carbonate (8.80 g, 63.64 mmol) were added. The mixture reacted at 90° C. for 16 h. The reaction solution was filtered and dried by means of a rotary dryer. Residue was purified by means of combi-flash chromatography using petroleum ether: ethyl acetate=3:1 to afford compound Z-28-1 (7 g, yield: 82.6%) yellow liquid. MS m/z (ESI): 400.2 [M+1].

Step 2: compound Z-28-1 (6.0 g) was resolved by supercritical fluid chromatography (SFC) (method: column type: IG 4.6*100 mm 5 μm, co-solvent: IPA/ACN=1/1[0.1% DEA], flow rate: 3.0 mL/min, column temperature: 40° C.) to obtain 2.2 g of compound Z-28-a (retention time: 1.931 minutes).

Step 3: compound Z-28-a (2.2 g, 5.51 mmol) was dissolved in hydrochloric acid/dioxane (10 mL), and the mixture reacted at 30° C. for 2 h. The reaction solution was dried by means of a rotary dryer, and the residue was dissolved in 50 mL of water and extracted twice with ethyl acetate. The aqueous phase was adjusted to pH=8 with aqueous ammonia, extracted twice with ethyl acetate, and dried over anhydrous sodium sulfate. The reaction solution was filtered and dried by means of a rotary dryer. Compound Z-28-P1 (1.3 g, yield: 79.1%) was obtained. MS m/z (ESI): 300.2 [M+1]. $^{1}$H NMR (400 MHz, DMSO-d6) δ 7.98 (d, J=2.0 Hz, 1H), 7.41 (d, J=7.6 Hz, 1H), 6.29 (d, J=2.0 Hz, 1H), 6.00 (s, 1H), 4.28-4.16 (m, 1H), 3.50-3.40 (m, 1H), 2.27-2.17 (m, 1H), 2.00-1.57 (m, 7H), 1.35-1.24 (m, 1H), 1.11-0.97 (m, 1H), 0.80 (t, J=7.6 Hz, 3H), 0.60-0.51 (m, 1H), 0.35-0.20 (m, 2H), 0.18-0.08 (m, 1H).

Example 28b: Preparation of Compound Z-28-P2

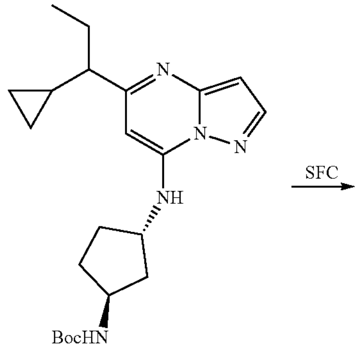

Z-28-1

-continued

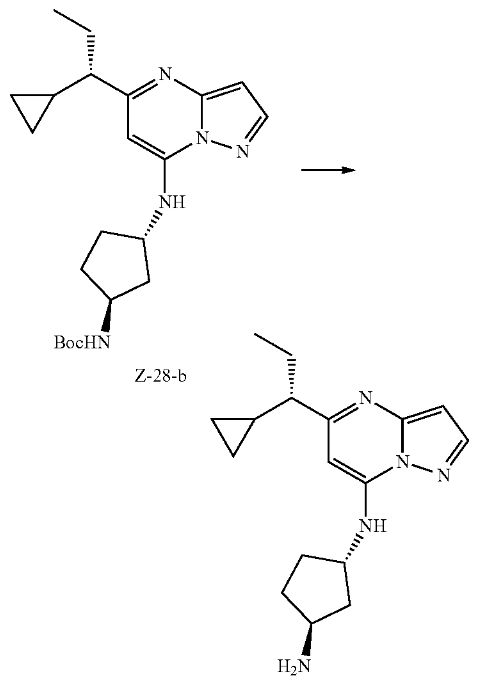

Z-28-b

Z-28-P2

Step 1: compound Z-28-1 (6.0 g) was resolved by supercritical fluid chromatography (SFC) (method: column type: IG 4.6*100 mm 5 μm, co-solvent: IPA/ACN=1/1[0.1% DEA], flow rate: 3.0 mL/min, column temperature: 40° C.) to obtain 2.3 g of compound Z-28-b (retention time: 2.566 minutes).

Step 2: compound Z-28-b (220 mg, 550.6 μmol) was dissolved in hydrochloric acid/dioxane (10 mL) and reacted for 2 h at 30° C. The reaction solution was dried by means of a rotary dryer, and the residue was dissolved in ethyl acetate and washed with saturated sodium bicarbonate twice, followed by drying over anhydrous sodium sulfate, filtration and drying by means of a rotary dryer. The residue was purified with preparative liquid chromatography (preparative column: 21.2×250 mm C18 column; system: 10 mM of $NH_4HCO_3H_2O$; wavelength: 254/214 nm; gradient: 5%-95% acetonitrile change) to afford compound Z-28-P2 (99.58 mg, yield: 60.10%). MS m/z (ESI): 300.2 [M+1]. $^{1}$H NMR (400 MHz, DMSO-d6) δ 7.98 (d, J=2.0 Hz, 1H), 7.42 (d, J=60 Hz, 1H), 6.29 (d, J=2.4 Hz, 1H), 6.01 (s, 1H), 4.26-4.16 (m, 1H), 3.50-3.40 (m, 1H), 2.25-2.17 (m, 1H), 2.00-1.57 (m, 7H), 1.34-1.24 (m, 1H), 1.10-0.97 (m, 1H), 0.80 (t, J=7.2 Hz, 3H), 0.58-0.48 (m, 1H), 0.32-0.17 (m, 2H), 0.16-0.06 (m, 1H).

Example 30a: Preparation of Compound Z-30-P1

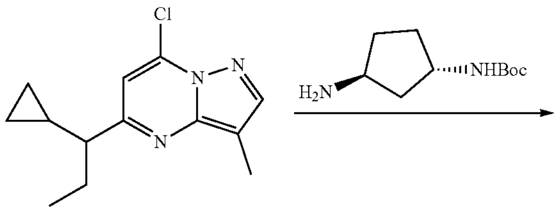

25-2

-continued

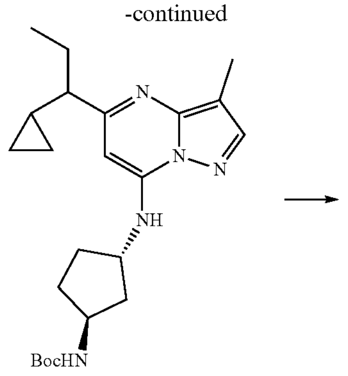

Z-30-1

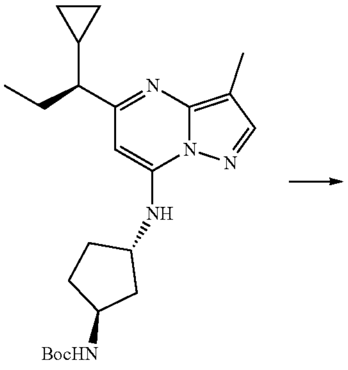

Z-30-a

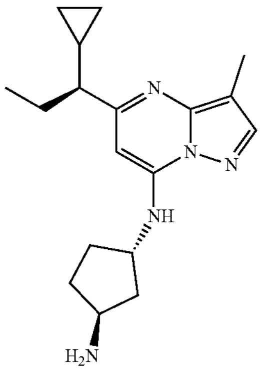

Z-30-P1

Step 1: compound Z-30-1 was prepared using compound 25-2 as starting material with reference to the scheme of step 3 of Example 1. MS m/z (ESI): 414.2 [M+1].

Step 2: 1.1 g of the compound Z-30-1 was resolved by supercritical fluid chromatography (SFC) (column type: IC-3 4.6*100 mm 3 μm, co-solvent: IPA [1% $NH_3$(7 M in MeOH)], injection volume: 5.00 μl, run time: 6.0 minutes, flow rate: 3.0 mL/min, pressure: 2000 psi, column temperature: 40° C.) to obtain 370 mg of compound Z-30-a (retention time: 2.135 minutes).

Step 3: compound Z-30-P1 was prepared with reference to step 2 of Example 26a. MS m/z (ESI): 314.2 [M+1]. $^1H$ NMR (400 MHz, DMSO-d6) δ 7.83 (s, 1H), 7.25 (d, J=7.6 Hz, 1H), 5.95 (s, 1H), 4.26-4.16 (m, 1H), 3.45-3.36 (m, 1H), 2.26-2.13 (m, 4H), 2.02-1.54 (m, 7H), 1.33-1.22 (m, 1H), 1.10-0.99 (m, 1H), 0.85-0.78 (m, 3H), 0.59-0.49 (m, 1H), 0.32-0.17 (m, 2H), 0.14-0.08 (m, 1H).

Example 30b: Preparation of Compound Z-30-P2

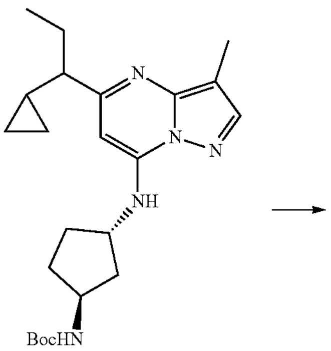

Z-30-1

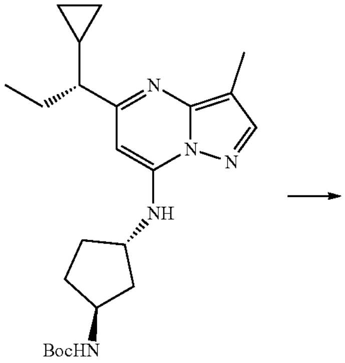

Z-30-b

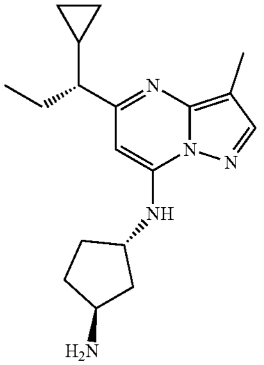

Z-30-P2

Step 1: 1.1 g of the compound Z-30-1 was resolved by supercritical fluid chromatography (SFC) (column type: IC-3 4.6*100 mm 3 μm, co-solvent: IPA [1% $NH_3$(7 M in MeOH)], injection volume: 5.00 μl, run time: 6.0 minutes, flow rate: 3.0 mL/min, pressure: 2000 psi, column temperature: 40° C.) to obtain 380 mg of compound Z-30-b (retention time: 2.416 minutes).

Step 2: compound Z-30-P2 was prepared with reference to step 2 of Example 26a. MS m/z (ESI): 314.2 [M+1]. $^1H$ NMR (400 MHz, DMSO-d6) δ 7.83 (s, 1H), 7.25 (d, J=7.6 Hz, 1H), 5.96 (s, 1H), 4.25-4.15 (m, 1H), 3.48-3.35 (m, 1H), 2.24-2.09 (m, 4H), 2.01-1.70 (m, 6H), 1.68-1.56 (m, 1H), 1.35-1.25 (m, 1H), 1.10-1.00 (m, 1H), 0.86-0.79 (m, 3H), 0.57-0.47 (m, 1H), 0.35-0.19 (m, 2H), 0.15-0.08 (m, 1H).

Example 31: Preparation of Compound Z-31

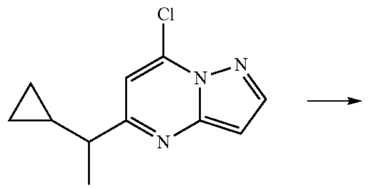

5-2

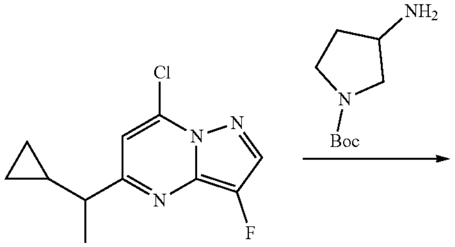

31-1

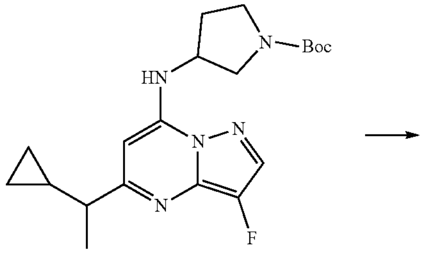

31-2

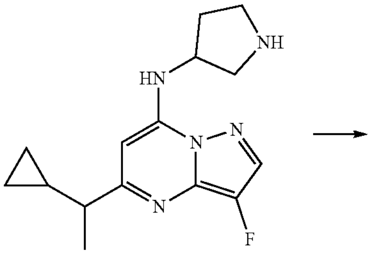

31-3

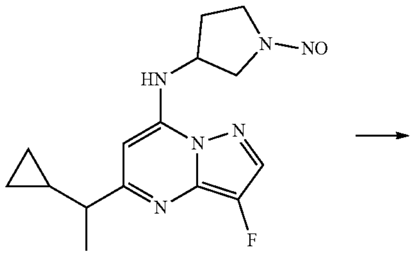

31-4

-continued

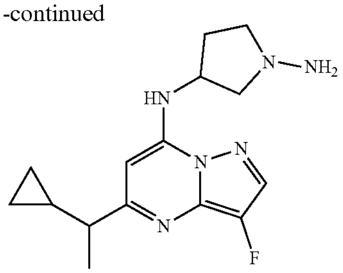

Z-31

Step 1: compound 5-2 (400 mg, 1.80 mmol) and acetic acid (216.70 mg, 3.61 mmol) were dissolved in acetonitrile (20 mL). After addition of 1-chloromethyl-4-fluoro-1,4-diazoniabicyclo[2.2.2]octane bis(tetrafluoroborate) (639.2 mg, 1.80 mmol) was added, followed by stirring at 70° C. for 4 h. The reaction was terminated, the solvent was removed under reduced pressure, and the residue was dissolved with ethyl acetate (50 mL). The organic phase was washed with saturated sodium bicarbonate solution (50 mL) and saturated sodium chloride solution (50 mL), dried over anhydrous sodium sulfate, filtered, and concentrated under reduced pressure. The residue was purified with silica gel column chromatography to afford compound 31-1 (200 mg, yield: 46.3%), light-yellow oil. MS m/z (ESI): 240.1 [M+1].

Step 2: compound 31-1 (100 mg, 417.23 μmol) and tert-butyl 3-aminopyrrolidine-1-carboxylate (116.6 mg, 625.84 μmol) were dissolved in acetonitrile (20 mL), and potassium carbonate (173.00 mg, 1.25 mmol) was added thereto. The reaction solution was stirred at 90° C. for 16 h. The reaction was terminated, dissolved with ethyl acetate (50 mL), washed with saturated sodium chloride solution (50 mL×3), dried over anhydrous sodium sulfate, filtered, and concentrated under reduced pressure. The residue was purified with silica gel column chromatography to afford compound 31-2 (120 mg, yield: 73.85%), light-yellow oil. MS m/z (ESI): 389.6 [M+1].

Step 3: compound 31-2 (120 mg, 308.11 μmol) was dissolved in a 4 M solution of hydrogen chloride in 1,4-dioxane (4 M, 7.70 mL). The reaction solution was stirred at room temperature for 3 h. The solvent was evaporated under reduced pressure, purified water (30 mL) was added, and the impurities were extracted with ethyl acetate (30 mL). The aqueous phase was adjusted to pH=9-10 with saturated sodium carbonate solution, and extracted with ethyl acetate (50 mL×2). The organic phase was dried over anhydrous sodium sulfate, filtered, and concentrated under reduced pressure to afford compound 31-3 (89 mg, yield: 99.83%) as light-yellow oil. MS m/z (ESI): 290 [M+1].

Step 4: compound 31-3 (90 mg, 311.04 μmol) was dissolved in water (2 mL) and acetic acid (2 mL) and a solution of sodium nitrite (31.73 mg, 466.56 μmol) in water (2 mL) was slowly added dropwise under ice bath. After slowly warming to room temperature and stirring for 2 h, the reaction solution was adjusted to pH=8 with saturated sodium bicarbonate, extracted with ethyl acetate (2*30 mL), dried over anhydrous sodium sulfate, and dried by means of a rotary dryer. Residue was purified by means of combi-flash chromatography using petroleum ether: ethyl acetate=1:1 to afford compound 31-4 (55 mg, yield: 55.54%), light-yellow solid. MS m/z (ESI): 319 [M+1].

Step 5: compound 31-4 (55 mg, 172.77 μmol) was dissolved in methanol (3 mL), and acetic acid (0.3 mL), and zinc (225.94 mg, 3.46 mmol) was added, and the mixture reacted at room temperature for 1 h. The reaction solution was added with ammonia water to adjust to pH=9, and extracted with ethyl acetate (2*30 mL). The organic phases were combined, washed with saturated salt water twice, dried over anhydrous sodium sulfate, and filtered. The residue was dried by means of a rotary dryer, and the resulting crude product was purified with preparative liquid chromatography (preparative column: 21.2×250 mm C18 column; system: 10 mM $NH_4HCO_3H_2O$; wavelength: 254/214 nm; gradient: 5%-95% acetonitrile change) to afford compound Z-31 (4.98 mg, yield: 9.07%). MS m/z (ESI): 304.6 [M+1]. $^1$H NMR (400 MHz, DMSO-d6) δ 8.16 (dd, J=6.0, 3.6 Hz, 1H), 7.58 (d, J=6.8 Hz, 1H), 6.12 (s, 1H), 4.28-4.16 (m, 1H), 3.01-2.91 (m, 1H), 2.91-2.68 (m, 2H), 2.67-2.52 (m, 1H), 2.33-2.18 (m, 1H), 2.07-1.95 (m, 1H), 1.93-1.81 (m, 1H), 1.30 (d, J=6.8 Hz, 3H), 1.10-0.98 (m, 1H), 0.55-0.47 (m, 1H), 0.39-0.30 (m, 1H), 0.27-0.15 (m, 2H).

Example 32: Preparation of Compound Z-32

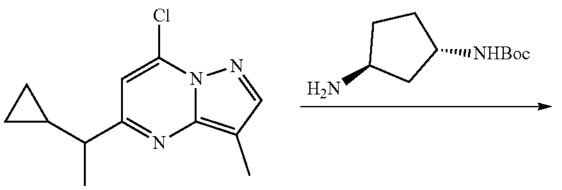

26-2

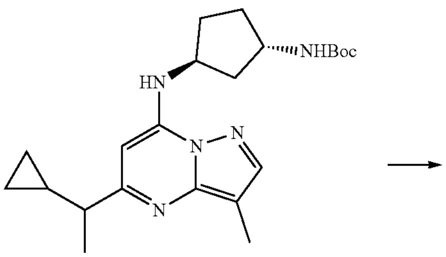

Z-32-1

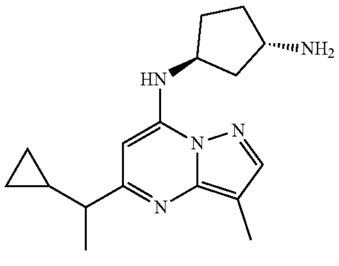

Z-32

Compound Z-32 was prepared using compound 26-2 as the starting material with reference to the schemes of step 3 and step 4 of Example 1. MS m/z (ESI): 300.2 [M+1]. $^1$H NMR (400 MHz, DMSO-d6) δ 7.83 (s, 1H), 7.43 (s, 1H), 6.01 (s, 1H), 4.25-4.13 (m, 1H), 3.99-3.91 (m, 1H), 2.24-1.81 (m, 4H), 2.16 (s, 3H), 1.79-1.72 (m, 1H), 1.67-1.58 (m, 1H), 1.50-1.40 (m, 1H), 1.30 (d, J=6.8 Hz, 3H), 1.10-1.01 (m, 1H), 0.54-0.46 (m, 1H), 0.38-0.30 (m, 1H), 0.23-0.16 (m, 2H).

Example 32a: Preparation of Compound Z-32-P1

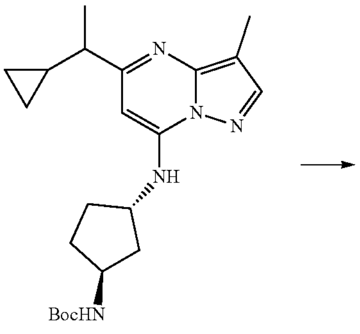

Z-32-1

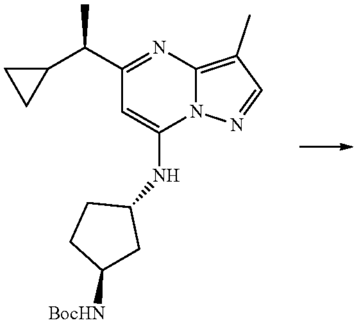

Z-32-a

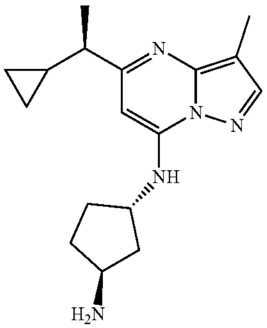

Z-32-P1

Step 1: 590 mg of the compound Z-32-1 was resolved by supercritical fluid chromatography (SFC) (column type: AD-3 4.6*100 mm 3 μm, co-solvent: EtOH [1% $NH_3$ (7 M in MeOH)], injection volume: 2.00 μl, run time: 4.0 minutes, flow rate: 3.0 mL/min, pressure: 2000 psi, column temperature: 40° C.) to afford compound Z-32-a (218 mg, 545.64 μmol, yield 36.95%, retention time: 2.592 minutes) as a yellow oil. MS m/z (ESI): 400.3 [M+1]. ee %=100%.

Step 2: compound Z-32-P1 was prepared with reference to step 2 of Example 26a. MS m/z (ESI): 300.2 [M+1]. $^1$H NMR (400 MHz, DMSO-d6) δ7.83 (s, 1H), 7.26 (d, J=4.8 Hz, 1H), 6.00 (s, 1H), 4.24-4.15 (m, 1H), 3.44-3.36 (m, 1H), 2.24-2.17 (m, 1H), 2.17 (s, 3H), 2.05-1.82 (m, 3H), 1.80-1.73 (m, 1H), 1.67-1.58 (m, 1H), 1.31 (d, J=7.0 Hz, 3H), 1.29-1.23 (m, 1H), 1.11-1.01 (m, 1H), 0.53-0.48 (m, 1H), 0.38-0.31 (m, 1H), 0.24-0.16 (m, 2H).

Example 32b: Preparation of Compound Z-32-P2

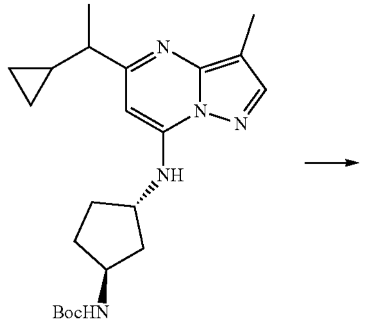

Z-32-1

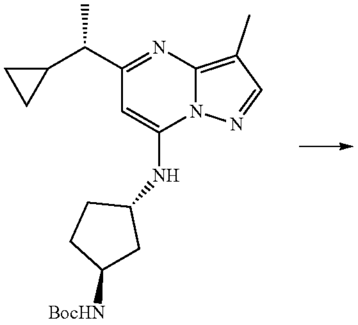

Z-32-b

-continued

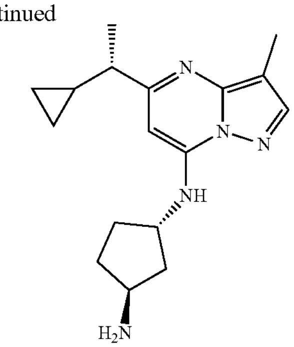

Z-32-P2

Step 1: 590 mg of the compound Z-32-1 was resolved by supercritical fluid chromatography (SFC) (column type: AD-3 4.6*100 mm 3 μm, co-solvent: EtOH [1% $NH_3$(7 M in MeOH)], injection volume: 2.00 μl, run time: 4.0 minutes, flow rate: 3.0 mL/min, pressure: 2000 psi, column temperature: 40° C.) to afford compound Z-32-b (241 mg, 603.21 mol, yield 40.85%, retention time: 3.167 minutes) as a yellow oil. MS m/z (ESI): 400.3 [M+1]. ee %=99.6%.

Step 2: compound Z-32-P2 was prepared with reference to step 2 of Example 26a. MS m/z (ESI): 300.2 [M+1]. $^1$H NMR (400 MHz, DMSO-d6) δ 7.83 (s, 1H), 7.27 (s, 1H), 6.00 (s, 1H), 4.26-4.15 (m, 1H), 3.44-3.38 (m, 1H), 2.25-2.18 (m, 1H), 2.17 (s, 3H), 2.04-1.82 (i, 4H), 1.79-1.71 (m, 1H), 1.68-1.59 (m, 1H), 1.31-1.30 (d, J=6.8 Hz, 4H), 1.28-1.24 (m, 1H), 1.10-1.01 (m, 1H), 0.53-0.47 (m, 1H), 0.37-0.32 (n, 1H), 0.24-0.16 (m, 2H).

Example 33 to Example 44

Compounds Z-33 to Z-44 was prepared with reference to the schemes of Example 1.

| Example No. | Structure | $^1$H NMR and MS |
|---|---|---|
| 33 | 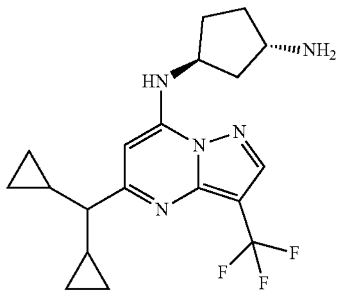 Z-33 | MS m/z (ESI): 380.2 [M + 1] 1H NMR (400 MHz, DMSO-d6) δ 8.39 (s, 1H), 7.95 (s, 1H), 6.31 (s, 1H), 4.31-4.22 (m, 1H), 3.44-3.38 (m, 1H), 2.24-2.16 (m, 1H), 1.99-1.59 (m, 6H), 1.39-1.35 (m, 1H), 1.32-1.17 (m, 3H), 0.57-0.50 (m, 2H), 0.38-0.24 (m, 4H), 0.12-0.07 (m, 2H). |
| 34 | 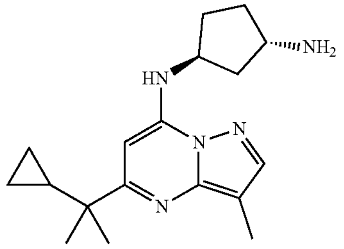 Z-34 | MS m/z (ESI): 314.2 [M + 1] 1H NMR (400 MHz, DMSO-d6) δ 7.84 (s, 1H), 7.20 (s, 1H), 6.14 (s, 1H), 4.25-4.16 (m, 1H), 3.44-3.37 (m, 1H), 2.25-2.19 (m, 1H), 2.18 (s, 3H), 1.95-1.89 (m, 1H), 1.89-1.83 (m, 1H), 1.79-1.73 (m, 1H), 1.68-1.60 (m, 1H), 1.34-1.25(m, 1H), 1.16 (s, 6H), 1.14-1.09 (m, 1H), 0.40-0.30 (m, 4H). |

-continued
| Example No. | Structure | ¹H NMR and MS |
| --- | --- | --- |
| 35 | 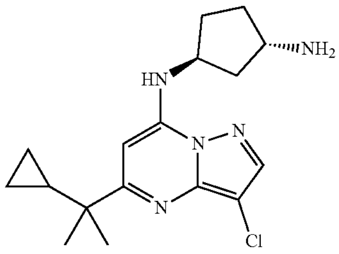 Z-35 | MS m/z (ESI): 334.1 [M + 1] 1H NMR (400 MHz, DMSO-d6) δ 8.16 (s, 1H), 7.68 (s, 1H), 6.28 (s, 1H), 4.28-4.22 (m, 1H), 3.44-3.38 (m, 1H), 2.23-2.14 (m, 1H), 1.9-1.85 (m, 2H), 1.7-1.73 (m, 1H), 1.71-1.61 (m, 1H), 1.34-1.25 (m, 1H), 1.16 (s, 6H), 1.14-1.11 (m, 1H), 0.42-0.30 (m, 4H). |
| 36 | 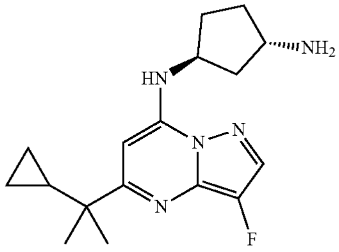 Z-36 | MS m/z (ESI): 318.1 [M + 1] 1H NMR (400 MHz, DMSO-d6) δ 8.14 (d, J = 3.6 Hz, 1H), 7.58 (s, 1H), 6.21 (s, 1H), 4.27-4.19 (m, 1H), 3.43-3.78 (m, 1H), 2.23-2.15 (m, 1H), 1.96-1.84 (m, 2H), 1.79-1.72(m, 1H), 1.70-1.62 (m, 1H), 1.3-1.25 (m, 1H), 1.15 (s, 6H), 1.14-1.09 (m, 1H), 0.40-0.31 (m, 4H). |
| 37 | 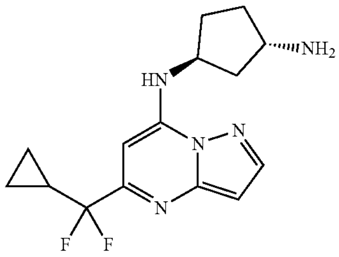 Z-37 | MS m/z (ESI): 308.1 [M + 1] 1H NMR (400 MHz, DMSO-d6) δ 8.15 (d, J = 2.0 Hz, 1H), 6.86 (d, J = 6.8 Hz, 1H), 6.53 (d, J = 2.8 Hz, 1H), 6.30 (s, 1H), 4.33-4.25 (m, 1H), 4.01-3.93 (m, 1H), 2.18-2.09 (m, 1H), 2.04-1.79 (m, 4H), 1.75-1.65 (m, 1H), 1.49-1.41 (m, 1H), 0.70-0.62 (m, 4H). |
| 38 | 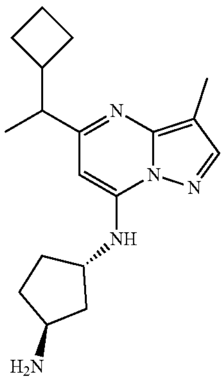 Z-38 | MS (ESI)m/z 314.2 [M + 1] ¹HNMR (400 MHz, DMSO-d6) δ 7.82 (s, 1H), 7.22-7.38 (m, 1H), 5.88 (s, 1H), 4.12-4.24 (m, 1H), 3.43-3.37 (m, 1H), 2.69 (dq, J = 10.2, 6.8 Hz, 1H), 2.55 (dd, J = 9.2, 6.4 Hz, 1H), 2.20 (d, J = 5.2 Hz, 1H), 2.16 (s, 3H), 2.10-2.02 (m, 1H), 1.80-1.95 (m, 2H), 1.80-1.56 (m, 7H), 1.24-1.34 (m, 1H), 1.11 (d, J = 6.8 Hz, 3H). |

-continued
| Example No. | Structure | $^1$H NMR and MS |
|---|---|---|
| 39 | 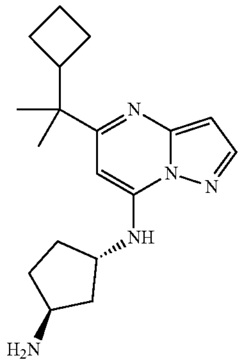 Z-39 | MS (ESI)m/z 314.2 [M + 1] $^1$H NMR (400 MHz, DMSO-d6) δ 7.98 (d, J = 2.4 Hz, 1H), 7.37 (d, J = 7.6 Hz, 1H), 6.31 (d, J = 2.4 Hz, 1H), 6.00 (s, 1H), 4.23 (q, J = 7.2 Hz, 1H), 3.46-3.40 (m, 1H), 2.64-2.73 (m, 1H), 2.15-2.24 (m, 1H), 2.00-1.53 (m, 11H), 1.28-1.40 (m, 1H), 1.22 (s, 6H). |
| 40 | 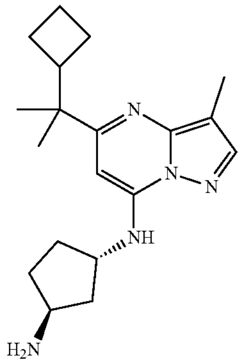 Z-40 | MS (ESI)m/z 328.2 [M + 1] $^1$H NMR (400 MHz, DMSO-d6) δ 7.83 (s, 1H), 7.19 (d, J = 7.6 Hz, 1H), 5.94 (s, 1H), 4.14-4.26 (m, 1H), 3.36-3.46 (m, 1H) 2.69 (q, J = 8.8 Hz, 1H), 2.19-2.24 (m, 1H), 2.17 (s, 3H), 2.00-1.52 (m, 12H), 1.49-1.27 (m, 1H), 1.23 (s, 6H). |
| 41 | 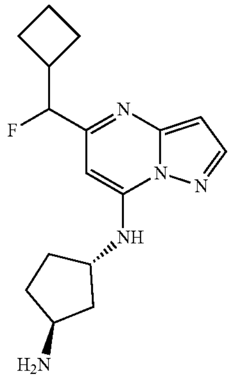 Z-41 | MS m/z (ESI): 304.1 [M + 1] $^1$H NMR (400 MHz, DMSO-d6) δ 8.05 (d, J = 2.4 Hz, 1H), 6.78-6.88 (m, 1H), 6.37 (d, J = 2.4 Hz, 1H), 6.15 (d, J = 10.8 Hz, 1H), 5.32 (dd, J = 48.8, 6.0 Hz, 1H), 4.19-4.29 (m, 1H), 3.48-3.39 (m, 1H), 2.99-2.81 (m, 1H), 2.10-2.22 (m, 1H), 2.11-1.75 (m, 9H), 1.73-1.59 (m, 1H), 1.25-1.50 (m, 1H). |

-continued
| Example No. | Structure | $^1$H NMR and MS |
|---|---|---|
| 42 | 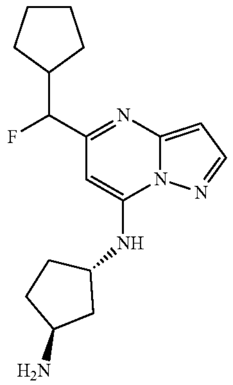 Z-42 | MS (ESI)m/z 318.2 [M + 1] $^1$H NMR (400 MHz, DMSO-d6) δ 8.06 (d, J = 2.0 Hz, 1H), 7.83 (s, 1H), 6.39 (d, J = 2.0 Hz, 1H), 6.18 (s, 1H), 5.19 (dd, J = 48.4, 7.2 Hz, 1H), 4.22-4.30 (m, 1H), 3.38-3.45 (m, 1H), 2.60-2.50 (m, 1H), 2.13-2.23 (m, 1H), 1.88-1.99 (m, 2H), 1.74-1.81 (m, 1H), 1.63-1.70 (m, 2H), 1.59-1.46 (m, 6H), 1.25-1.38 (m, 2H). |
| 43 | 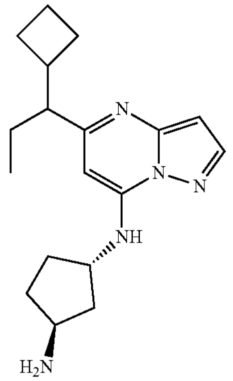 Z-43 | MS (ESI)m/z 314.2 [M + 1] $^1$H NMR (400 MHz, DMSO-d6) δ 7.97 (d, J = 2.4 Hz, 1H), 7.57-7.38 (m, 1H), 6.28 (d, J = 2.4 Hz, 1H), 5.95 (s, 1H), 4.26-4.12 (m, 1H), 3.45-3.37 (m, 1H), 2.58-2.49 (m, 1H), 2.23-2.13 (m, 1H), 2.09-2.04 (m, 1H), 1.97-1.82 (m, 2H), 1.81-1.39 (m, 10H), 1.35-1.25 (m, 1H), 0.70 (t, J = 7.2 Hz, 3H). |
| 44 | 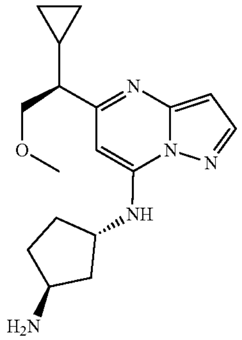 Z-44 | MS m/z (ESI): 316.2 [M + 1] $^1$H NMR (400 MHz, DMSO-d6) δ 8.00 (d, J = 2.0 Hz, 1H), 6.87-6.80 (m, 1H), 6.30 (d, J = 2.0 Hz, 1H), 6.08 (s, 1H), 4.21-4.12 (m, 1H), 3.99-3.91 (m, 1H), 3.83 (t, J = 9.2 Hz, 1H), 3.62 (dd, J = 9.2, 5.2 Hz, 1H), 3.17 (s, 3H), 2.20-2.11 (m, 2H), 2.05-1.81 (m, 3H), 1.73-1.62 (m, 1H), 1.49-1.38 (m, 1H), 1.04-0.95 (m, 1H), 0.55-0.46 (m, 1H), 0.34-0.22 (m, 2H), 0.20-0.13 (m, 1H). |

Example 38a: Preparation of Compound Z-38-P1

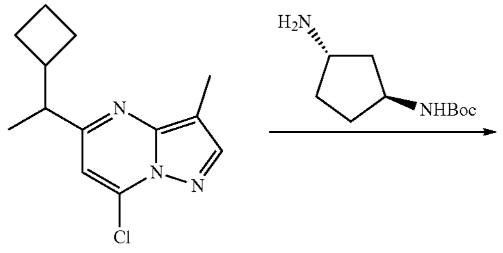

32-2

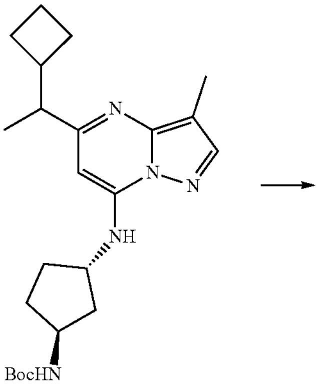

Z-38-1

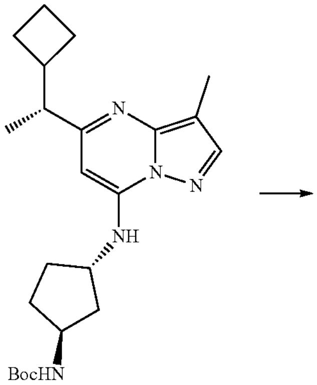

Z-38-a

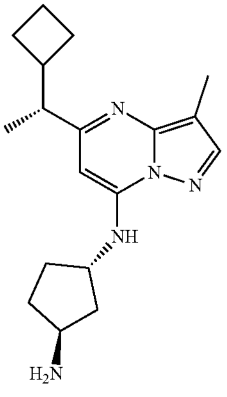

Z-38-P1

Step 1: compound Z-38-1 was prepared using compound 35-2 as the starting material with reference to the scheme of step 3 of Example 1. MS m/z (ESI): 414.2 [M+1].

Step 2: 850 mg of the compound Z-38-1 was resolved by supercritical fluid chromatography (SFC) (column type: IC-3 4.6*100 mm 3 μm, co-solvent: IPA [1% $NH_3$(7 M in MeOH)], injection volume: 2.00 μl, run time: 6.0 minutes, flow rate: 3.0 mL/min, pressure: 2000 psi, column temperature: 40° C.) to obtain 230 mg of compound Z-38-a (retention time 3.138 minutes).

Step 3: compound Z-38-P1 was prepared with reference to step 2 of Example 26a. MS m/z (ESI): 314.2 [M+1]. $^1H$ NMR (400 MHz, DMSO-d6) δ 7.84 (s, 1H), 7.29 (d, J=7.6 Hz, 1H), 5.90 (s, 1H), 4.25-4.17 (m, 1H), 3.45-3.38 (m, 1H), 2.74-2.67 (m, 1H), 2.61-2.52 (m, 1H), 2.20 (d, J=8.0 Hz, 1H), 2.18 (s, 3H), 2.12-2.05 (m, 1H), 1.97-1.82 (m, 2H), 1.81-1.56 (m, 7H), 1.35-1.25 (m, 1H), 1.13 (d, J=6.8 Hz, 3H).

Example 38b: Preparation of Compound Z-38-P2

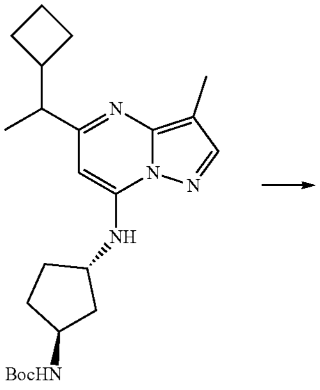

Z-38-1

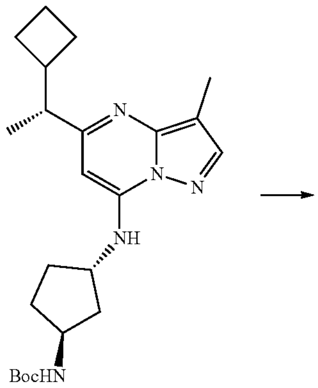

Z-38-b

-continued

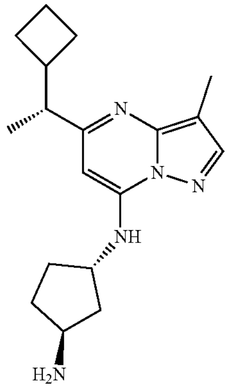

Z-38-P2

Step 1: 850 mg of the compound Z-38-1 was resolved by supercritical fluid chromatography (SFC) (column type: IC-3 4.6*100 mm 3 μm, co-solvent: IPA [1% $NH_3$(7 M in MeOH)], injection volume: 2.00 μl, run time: 6.0 minutes, flow rate: 3.0 mL/min, pressure: 2000 psi, column temperature: 40° C.) to obtain 230 mg of compound Z-38-b (retention time: 3.507 minutes).

Step 2: compound Z-38-P2 was prepared with reference to step 2 of Example 26a. MS m/z (ESI): 314.2 [M+1]. $^1$H NMR (400 MHz, DMSO-d6) δ 7.84 (s, 1H), 7.30 (d, J=7.6 Hz, 1H), 5.91 (s, 1H), 4.25-4.17 (m, 1H), 3.46-3.39 (m, 1H), 2.76-2.66 (m, 1H), 2.61-2.52 (m, 1H), 2.25-2.19 (m, 1H), 2.18 (s, 3H), 2.12-2.05 (m, 1H), 1.98-1.82 (m, 2H), 1.81-1.58 (m, 7H), 1.36-1.26 (m, 1H), 1.13 (d, J=6.8 Hz, 3H).

Example 41a: Preparation of Compound Z-41-P1

Z-41-P1

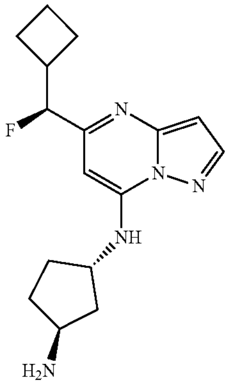

Compound Z-41 (76 mg, 250.51 μmol) was subjected to chiral resolution (column type: IC-3 4.6*100 mm 3 um; co-solvents: IPA [1% $NH_3$(7 M in MeOH)]; injection volume: 5.00 μl; run time: 6.0 minutes; flow rate: 3.0 mL/min; pressure: 2000 psi; column temperature: 40° C.) to afford compound Z-41-P1 (9.76 mg, retention time: 2.153 minutes), yield: 12.84%, purity: 100%. MS m/z (ESI): 304.2 [M+H$^+$]. $^1$H NMR (400 MHz, DMSO-d6) δ 8.08 (d, J=2.4 Hz, 1H), 7.82 (s, 1H), 6.39 (d, J=2.4 Hz, 1H), 6.15 (s, 1H), 5.34 (dd, J=48.8, 6.0 Hz, 1H), 4.22-4.32 (m, 1H), 3.40-3.47 (m, 1H), 2.86-2.99 (m, 1H), 2.24-2.13 (m, 1H), 2.12-1.60 (m, 12H), 1.27-1.36 (m, 1H).

Example 41b: Preparation of Compound Z-41-P2

Z-41-P2

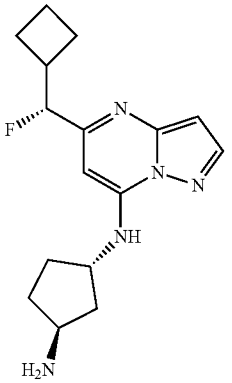

Compound Z-41 (76 mg, 250.51 μmol) was subjected to chiral resolution (column type: IC-3 4.6*100 mm 3 um; co-solvents: IPA [1% $NH_3$(7 M in MeOH)]; injection volume: 5.00 ul; run time: 6.0 minutes; flow rate: 3.0 mL/min; pressure: 2000 psi; column temperature: 40° C.) to afford compound Z-41-P2 (11.42 mg, retention time 1.448 minutes), yield: 14.98%, purity: 99.72%. MS m/z (ESI): 304.2 [M+H$^+$]. $^1$H NMR (400 MHz, DMSO-d6) δ 8.08 (d, J=2.4 Hz, 1H), 7.83 (s, 1H), 6.39 (d, J=2.4 Hz, 1H), 6.15 (s, 1H), 5.34 (dd, J=48.8, 6.0 Hz, 1H), 4.21-4.31 (m, 1H), 3.48-3.41 (m, 1H), 3.05-2.86 (m, 1H), 2.15-2.25 (m, 1H), 2.13-1.59 (m, 12H), 1.27-1.37 (m, 1H).

Example 45: Preparation of Compound Z-45

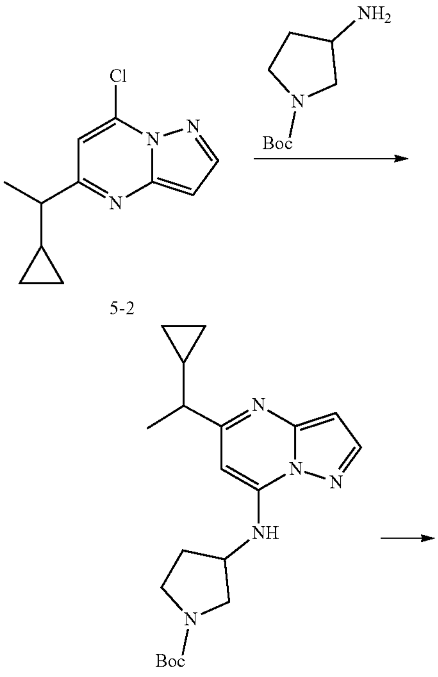

5-2

45-1

-continued

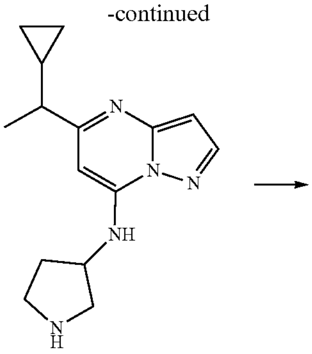

45-2

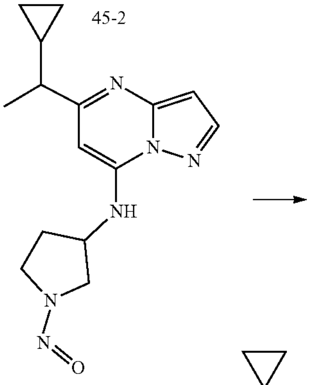

45-3

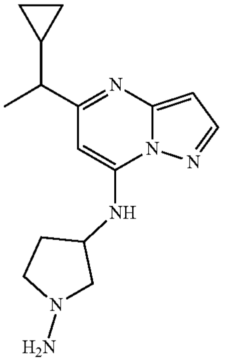

Z-45

Step 1: compound 5-2 (200 mg, 902.18 μmol), tert-butyl 3-aminopyrrolidine-1-carboxylate (201.64 mg, 1.08 mmol), and potassium carbonate (374.06 mg, 2.71 mmol) were dissolved in acetonitrile (5 mL), and the mixture was warmed to 90° C. and stirred overnight. The reaction solution was added with 5 mL of water, and extracted with ethyl acetate (10 mL×3). The organic phases were combined and washed with brine, dried over anhydrous sodium sulfate and dried by means of a rotary dryer under reduced pressure. The resulting residue was purified with silica gel column chromatography with an eluent of 0-40% ethyl acetate in petroleum ether to afford compound 45-1 (0.28 g, light-yellow oil) in yield of 83.55%. MS m/z (ESI): 372.2 [M+1].

Step 2: compound 45-1 (0.28 g, 753.75 μmol) was dissolved in hydrochloric acid-dioxane (4 M) (5 mL) and stirred at room temperature for 2 h. The solvent was removed under reduced pressure to afford crude compound 45-2 (230 mg, light-yellow solid hydrochloride), yield: 99.13%. MS m/z (ESI): 308.2 [M+1].

Step 3: compound 45-2 (150 mg, 487.30 μmol, HCl) was dissolved in water (1 mL) and acetic acid (2 mL) and cooled to 0° C. under argon protection. Sodium nitrite (67.25 mg, 974.59 μmol) dissolved in water (1 mL) was slowly added dropwise to the solution. The mixture was warmed to room temperature and stirred for 1.5 h, then added with water (10 mL), extracted with ethyl acetate (10 mL×3). The organic phases were combined, washed with aqueous sodium bicarbonate and saturated brine, dried over anhydrous sodium sulfate, and dried by means of a rotary dryer to afford crude compound 45-3 (140 mg, brown oil), yield: 95.65%. MS m/z (ESI): 301.1 [M+1].

Step 4: compound 45-3 (140 mg, 466.11 μmol) was dissolved in methanol (3 mL) and acetic acid (0.3 mL), and zinc dust (609.58 mg, 9.32 mmol) was added. The mixture was stirred at room temperature for 1 h. The zinc powder was filtered off, while the solvent was dried by means of a rotary dryer, dissolved in ethyl acetate (5 mL), washed with aqueous sodium bicarbonate solution and brine, dried over anhydrous sodium sulfate, and concentrated under reduced pressure to afford the crude product. Compound Z-45 (36.59 mg) was obtained by preparative HPLC chromatography in yield of 23.78%, purity: 86.74%. MS m/z (ESI): 287.1 [M+1]. $^1$H NMR (400 MHz, DMSO-d6) δ 7.99 (d, J=2.4 Hz, 1H), 7.40 (s, 1H), 6.31 (d, J=2.4 Hz, 1H), 6.09 (s, 1H), 4.24-4.15 (m, 1H), 2.98-2.92 (m, 1H), 2.84-2.77 (m, 1H), 2.76-2.77 (m, 1H), 2.60-2.53 (m, 1H), 2.31-2.19 (m, 1H), 2.03-1.94 (m, 1H), 1.93-1.80 (m, 1H), 1.29 (d, J=6.8 Hz, 3H), 1.10-0.99 (m, 1H), 0.54-0.44 (m, 1H), 0.37-0.30 (m, 1H), 0.25-0.14 (m, 2H). Example 46 to Example 59, and Example 64

Compounds Z-46 to Z-59 and Z-64 was prepared with reference to the schemes of Example 1

| Example No. | Structure | $^1$H NMR and MS |
|---|---|---|
| 46 | 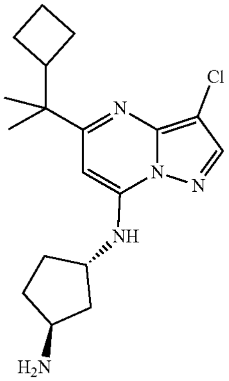 Z-46 | MS (ESI)m/z 348.1 [M + 1]. $^1$H NMR (400 MHz, DMSO-d6) δ 8.14 (s, 1H), 7.64 (s, 1H), 6.08 (s, 1H), 4.32-4.18 (m, 1H), 3.47-3.40 (m, 1H), 2.76-2.64 (m, 1H), 2.23-2.14 (m, 1H), 2.01-1.54 (m, 10H), 1.38-1.29 (m, 1H), 1.23 (s, 6H). |

-continued
| Example No. | Structure | $^1$H NMR and MS |
|---|---|---|
| 48 | 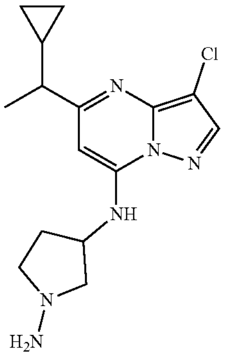 Z-48 | MS (ESI)m/z 321.1 [M + 1]. $^1$H NMR (400 MHz, DMSO-d6) δ 8.16 (s, 1H), 7.80-7.55 (m, 1H), 6.21 (s, 1H), 4.29-4.12 (m, 1H), 2.99-2.91 (m, 1H), 2.83-2.76 (m, 1H), 2.75-2.69 (m, 1H), 2.61-2.53 (m, 1H), 2.31-2.17 (m, 1H), 2.07-1.98 (m, 1H), 1.93-1.83 (m, 1H), 1.30 (d, J = 6.8 Hz, 3H), 1.11-0.99 (m, 1H), 0.54-0.47 (m, 1H), 0.39-0.30 (m, 1H), 0.25-0.15 (m, 2H). |
| 49 | 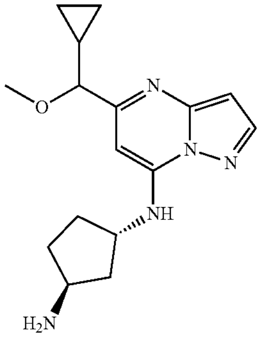 Z-49 | MS (ESI)m/z 302.1 [M + 1]. $^1$H NMR (400 MHz, DMSO-d6) δ 8.03 (d, J = 2.4 Hz, 1H), 7.80-7.60 (m, 1H), 6.36 (d, J = 2.4 Hz, 1H), 6.17-6.08 (m, 1H), 4.26-4.16 (m, 1H), 4.01-3.92 (m, 1H), 3.51 (d, J = 7.6 Hz, 1H), 3.20 (s, 3H), 2.25-2.06 (m, 1H), 2.06-1.59 (m, 4H), 1.1.50-1.25 (m, 1H), 1.19-1.09 (m, 1H), 0.55-0.49 (m, 1H), 0.46-0.40 (m, 1H), 0.39-0.27 (m, 2H). |
| 50 | 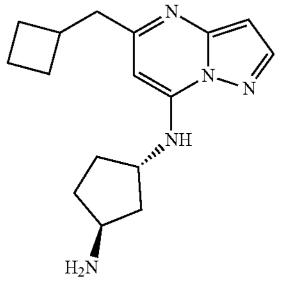 Z-50 | MS m/z (ESI): 286.2 [M + 1]. $^1$H NMR (400 MHz, DMSO-d6) δ 7.99 (s, 1H), 7.57 (s, 1H), 6.28 (d, J = 2.0 Hz, 1H), 6.00 (s, 1H), 4.17-3.97 (m, 1H), 3.66-3.30(m, 5H), 2.73 (s, 2H), 2.20-2.08 (m, 1H), 1.99-1.66 (m, 7H), 1.58-1.46 (m, 1H). |
| 51 | 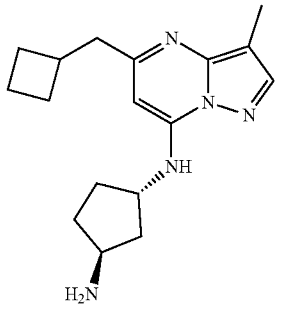 Z-51 | MS m/z (ESI): 300.3 [M + 1] $^1$H NMR (400 MHz, DMSO-d6) δ 7.84 (s, 1H), 7.46 (s, 1H), 5.99 (s, 1H), 4.20-4.10 (m, 1H), 4.05-3.96 (m, 1H), 2.78-2.70 (m, 2H), 2.17 (s, 3H), 2.06-1.31 (m, 13H). |

-continued
| Example No. | Structure | $^1H$ NMR and MS |
|---|---|---|
| 52 | 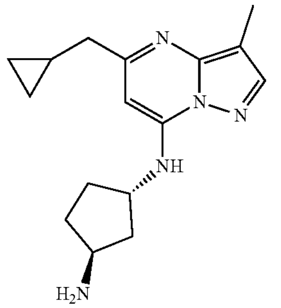 Z-52 | MS m/z (ESI): 286.2 [M + 1] $^1H$ NMR (400 MHz, DMSO-d6) δ 7.85 (s, 1H), 7.44-7.35 (m, 1H), 6.05 (s, 1H), 4.20 (s, 1H), 3.42 (s, 1H), 2.55 (d, J = 6.8 Hz, 2H), 2.23-2.15 (m, 4H), 1.93-1.81 (m, 3H), 1.68 (d, J = 8.0 Hz, 1H), 1.47-1.34 (m, 1H), 1.12 (s, 1H), 0.49 (d, J = 7.6 Hz, 2H), 0.25 (d, J = 4.4 Hz, 2H). |
| 53 | 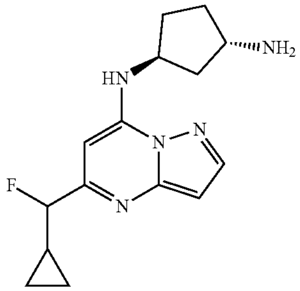 Z-53 | MS m/z (ESI): 290.1 [M + 1] $^1H$ NMR (400 MHz, DMSO-d6) δ 7.97 (s, 1H), 7.53 (s, 1H), 6.22 (s, 1H), 6.15 (s, 1H), 4.52-4.50 (m, 1H), 4.42 (s, 1H), 4.32-4.24 (m, 2H), 3.46 (s, 2H), 2.20 (s, 1H), 2.10 (s, 1H), 1.94 (s, 2H), 1.84 (s, 2H), 1.67 (s, 1H), 1.34-1.26 (m, 2H), 1.02 (s, 1H). |
| 54 | 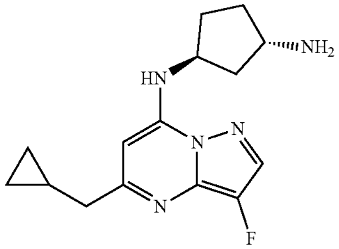 Z-54 | MS m/z (ESI): 290.2 [M + 1] $^1H$ NMR (400 MHz, DMSO-d6) δ 8.16 (d, J = 3.6 Hz, 1H), 7.71 (s, 1H), 6.13 (s, 1H), 4.33-4.12 (m, 1H), 3.44 (s, 1H), 2.56 (d, J = 4.0 Hz, 2H), 2.29-2.08 (m, 1H), 2.07-1.85 (m, 2H), 1.70-1.65 (m, 2H), 1.39-1.25 (m, 1H), 1.16-1.13 (m, 1H), 0.59-0.41 (m, 2H), 0.34-0.16 (m, 2H). |
| 55 | 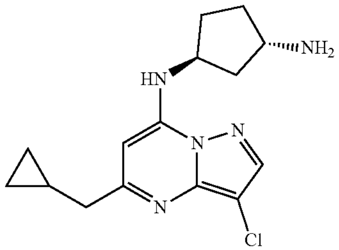 Z-55 | MS m/z (ESI): 306.1 [M + 1] $^1H$ NMR (400 MHz, DMSO-d6) δ 8.19 (s, 1H), 8.03 (d, J = 8.0 Hz, 1H), 7.54 (s, 1H), 6.35 (s, 1H), 4.50-4.45 (m, 1H), 3.76-3.63 (m, 1H), 2.57 (d, J = 4.0 Hz, 1H), 2.24-2.08 (m, 4H), 1.85-1.61 (m, 2H), 1.18-1.12 (m, 1H), 0.55-0.44 (m, 2H), 0.27-0.26 (m, 2H). |

-continued
| Example No. | Structure | $^1$H NMR and MS |
|---|---|---|
| 56 | 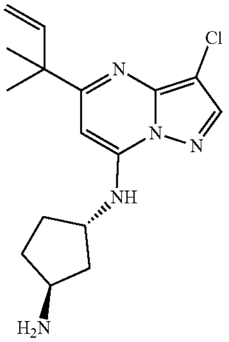<br>Z-56 | MS m/z (ESI): 320.1 [M + 1] $^1$H NMR (400 MHz, DMSO-d6) δ 8.19 (s, 1H), 7.63 (s, 1H), 6.19 (dd, J = 8.0, 12.0 Hz, 1H), 6.10 (s, 1H), 5.20-4.99 (m, 2H), 4.34-4.09 (m, 1H), 3.50-3.40(m, 1H), 2.26-2.11 (m, 1H), 1.95-1.89 (m, 2H), 1.72-1.64 (m, 2H), 1.43 (s, 6H), 1.35-1.30 (m, 1H). |
| 57 | 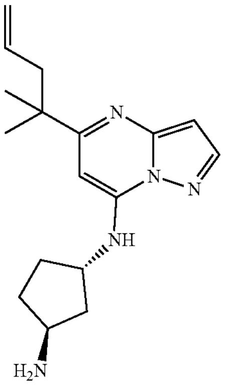<br>Z-57 | MS m/z (ESI): 300.2 [M + 1] $^1$H NMR (400 MHz, DMSO-d6) δ 8.02 (s, 1H), 7.57 (s, 1H), 6.35 (s, 1H), 6.12 (s, 1H), 5.77-5.49 (m, 1H), 5.01-4.93 (m, 2H), 4.35-4.25 (m, 1H), 3.50-3.40 (m, 1H), 2.46 (d, J = 7.6 Hz, 2H), 2.25-2.15 (m, 1H), 2.02-1.95 (m, 3H), 1.76-1.67 (m, 1H), 1.55-1.45 (m, 1H), 1.29-1.23 (m, 6H). |
| 58 | 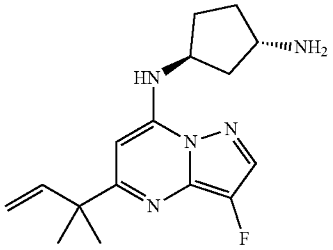<br>Z-58 | MS m/z (ESI): 304.1 [M + 1] $^1$H NMR (400 MHz, DMSO-d6) δ 8.17 (d, J = 3.6 Hz, 1H), 7.64 (s, 1H), 6.17 (dd, J = 8.0, 12.0 Hz, 1H), 6.02 (s, 1H), 5.14-5.06 (m, 2H), 4.31-4.08 (m, 1H), 3.45-3.35 (m, 1H), 2.20-2.14 (m, 1H), 1.97-1.85 (m, 2H), 1.78-1.61 (m, 2H), 1.41 (s, 6H), 1.35-1.28 (m, 1H). |
| 59 | 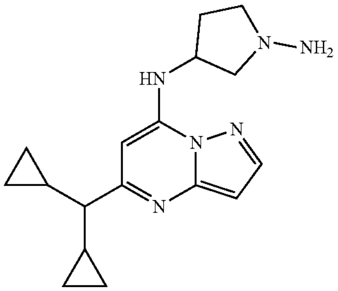<br>Z-59 | MS m/z (ESI): 313.2 [M + 1] $^1$H NMR (400 MHz, DMSO-d6) δ 8.00 (s, 1H), 7.61-7.30 (m, 1H), 6.31 (s, 1H), 6.07 (s, 1H), 4.20-4.10 (m, 1H), 3.05-2.91 (m, 1H), 2.89-2.77 (m, 1H), 2.74-2.71 (m, 1H), 2.65-2.56 (m, 1H), 2.30-2.05 (m, 1H), 1.87-1.75 (m, 1H), 1.30-1.21 (m, 3H), 0.55-0.45 (m, 2H), 0.29-0.27 (m, 4H), 0.11-0.01 (m, 2H). |

-continued

| Example No. | Structure | $^{1}$H NMR and MS |
|---|---|---|
| 64 | 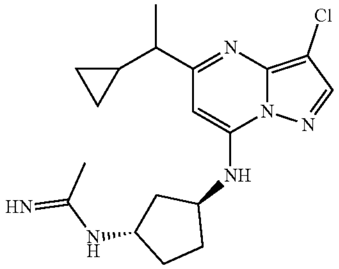 Z-64 | MS m/z (ESI): 361.2 [M + 1]. |

Example 60: Preparation of Compound Z-60

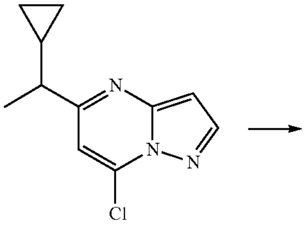

5-2

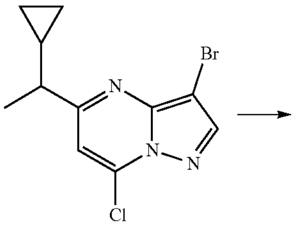

49-2

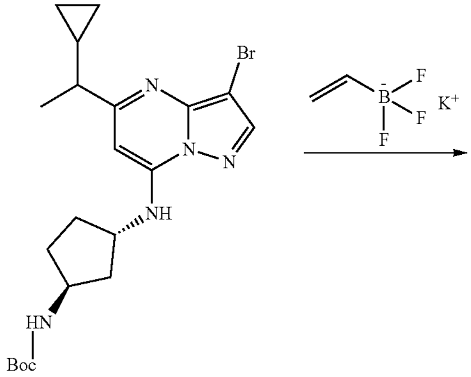

Z-60-2

-continued

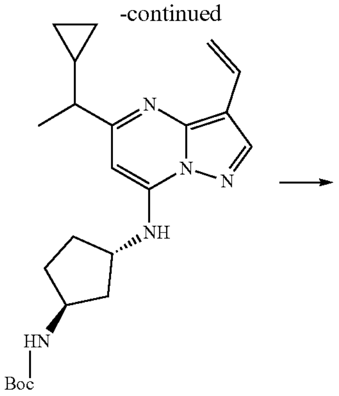

Z-60-2

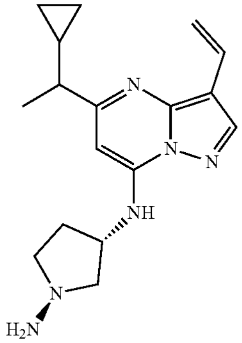

Z-60

Step 1: N-bromosuccinimide (562.01 mg, 3.16 mmol) dissolved to acetonitrile (5 mL) was added dropwise to a solution of compound 5-2 (700 mg, 3.16 mmol) in acetonitrile (10 mL) at 0° C. under nitrogen protection. After completion of addition, the mixture reacted at room temperature for 0.5 h. The reaction solution was poured into water, and extracted with ethyl acetate (5 mL*2), while the organic layer was washed with saturated brine, dried over anhydrous sodium sulfate, and concentrated to afford the crude product. The crude was purified with column chromatography (petroleum ether: ethyl acetate=90%:10%) to afford compound 49-2 (946 mg, 96.57% yield) as a yellow oil. MS m/z (ESI): 300.0 [M+1].

Step 2: compound 49-2 (300 mg, 998.06 μmol), potassium carbonate (344.84 mg, 2.50 mmol), tert-butyl ((1S, 3S)-3-aminocyclopentyl) carbamate (239.87 mg, 1.20 mmol), and acetonitrile (10 mL) were mixed under nitrogen protection, and the mixture was heated to 90° C. and reacted for 16 h. The reaction solution was filtered, and the filtrate was concentrated to afford the crude product. The crude was purified with column chromatography (petroleum ether: ethyl acetate=770%:30%~65%:35%) to afford compound Z-60-1 (433 mg, yield of 93.42%) as a colorless oil. MS m/z (ESI): 464.2 [M+1].

Step 3: compound Z-60-1 (383 mg, 824.72 μmol), potassium vinyl trifluoroborate (331.41 mg, 2.47 mmol), 1,1'-bis-diphenylphosphino ferrocene palladium dichloride (120.69 mg, 164.94 μmol), potassium carbonate (455.93 mg, 3.30 mmol), 1,4-dioxane (10 mL), and water (2.5 mL) were mixed under nitrogen protection. Thereafter, the mixture reacted under microwave at 120° C. for 2 h. The reaction solution was filtered, and the filtrate was added with water, and extracted with ethyl acetate (10 mL*2). The organic layer was washed with saturated brine, dried over anhydrous sodium sulfate, and concentrated to afford the crude product. The crude was purified with column chromatography (petroleum ether: ethyl acetate=90%: 10% to 70%: 30%) to afford compound Z-60-2 (320 mg, yield of 94.28%) as a light-yellow oil. MS m/z (ESI): 412.2 [M+1].

Step 4: zinc bromide (1.05 g, 4.67 mmol) was added to a solution of compound Z-60-2 (320 mg, 777.57 μmol) in dichloromethane (18 mL) under nitrogen protection, and after completion of addition, the mixture reacted at room temperature for 16 h. Then, zinc bromide (1.05 g, 4.67 mmol) was supplementally added and further reacted at room temperature for 16 h. The reaction solution was added with water and a small amount of methanol, and then extracted with dichloromethane (20 mL*2). The organic layers were combined and washed with saturated brine, dried over anhydrous sodium sulfate, and concentrated to afford the crude product. The crude product was purified with preparative liquid chromatography (preparative column: 21.2×250 mm C18 column; system: 10 mM $NH_4HCO_3H_2O$; wavelength: 254/214 nm) to afford compound Z-60 (24.73 mg, 9.82% yield). MS m/z (ESI): 312.2 [M+1]. $^1$H NMR (400 MHz, DMSO-d6) δ 8.18 (s, 1H), 6.86 (s, 1H), 6.76 (dd, J=18.0, 11.6 Hz, 1H), 6.15 (s, 1H), 5.93 (dd, J=17.6, 2.0 Hz, 1H), 5.07 (dd, J=11.2, 2.4 Hz, 1H), 4.25-4.18 (m, 1H), 4.03-3.92 (m, 1H), 2.22-2.12 (m, 1H), 2.09-1.90 (m, 4H), 1.75-1.64 (m, 1H), 1.51-1.45 (m, 1H), 1.34 (d, J=7.2 Hz, 3H), 1.13-1.04 (m, 1H), 0.56-0.50 (m, 1H), 0.42-0.35 (m, 1H), 0.28-0.19 (m, 2H).

Example 61: Preparation of Compound Z-61

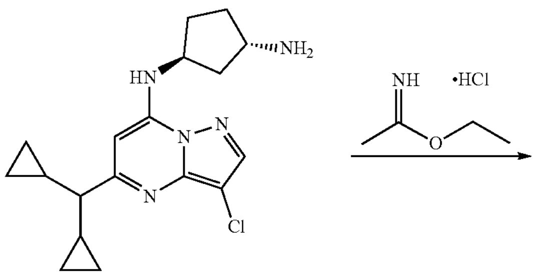

Z-9

-continued

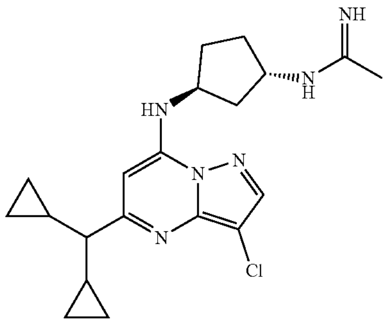

Z-61

Compound Z-9 (150 mg, 352.47 μmol) and ethyl acetamide hydrochloride (262.0 mg, 2.12 mmol) were dissolved in acetonitrile (10 mL), and N,N-diisopropylethyl amine (0.68 mL, 3.91 mmol) was added thereto. The reaction solution was stirred at 80° C. for 2 h, cooled to room temperature, added with 7N methanolic ammonia solution of 5 mL, and stirred at room temperature for 1 h. The reaction solution was diluted with ethyl acetate (50 mL), and washed with saturated sodium chloride solution (50 mL×3), and the organic phase was dried over anhydrous sodium sulfate, filtered, and concentrated under reduced pressure to afford compound Z-61 (33.58 mg, light-yellow oil) in yield of 25.11% using preparative HPLC chromatography. MS m/z (ESI): 367.2 [M+1]. $^1$H NMR (400 MHz, DMSO-d6) δ 7.86 (s, 1H), 7.42 (s, 1H), 5.99 (s, 1H), 4.24-4.10 (m, 1H), 4.00-3.90 (m, 1H), 2.29-2.12 (m, 4H), 2.11-1.93 (m, 2H), 1.90-1.72 (m, 4H), 1.68-1.59 (m, 1H), 1.48-1.40 (m, 1H), 1.37-1.12 (m, 3H), 0.58-0.51 (m, 2H), 0.38-0.24 (m, 4H), 0.15-0.05 (m, 2H).

Example 62: Preparation of Compound Z-62

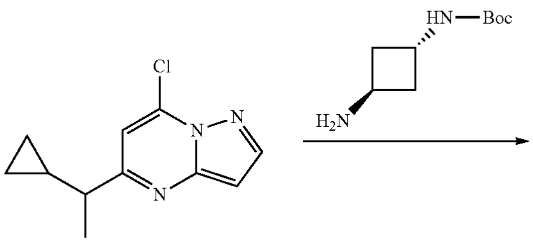

5-2

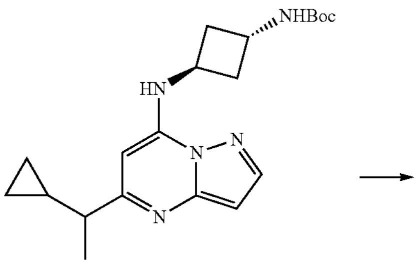

Z-62-1

-continued

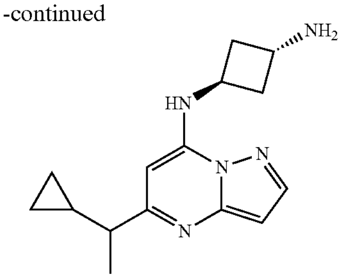

Z-62

Step 1: compound 5-2 (100 mg, 451.1 μmol) and tert-butyl ((1R,3R)-3-aminocyclobutyl)carbamate (84.0 mg, 451.1 μmol) were dissolved in acetonitrile (20 mL), and potassium carbonate (187.0 mg, 1.35 mmol) was added thereto. The reaction solution was stirred at 90° C. for 16 h. The reaction solution was added with ethyl acetate (80 mL), and washed with saturated sodium chloride solution (80 mL×3), and the organic phase was dried over anhydrous sodium sulfate, filtered, and concentrated under reduced pressure to afford compound Z-62-1 (120 mg, light-yellow oil) in yield of 71.6%. MS m/z (ESI): 372.2 [M+1].

Step 2: compound Z-62-1 (120 mg, 323.04 μmol) was dissolved in 1,4-dioxane (2 mL), and then added with a 4 M solution of the salt hydrogen chloride/1,4-dioxane (5 mL). The reaction solution was stirred at room temperature for 5 h. The solvent was evaporated under reduced pressure, water (50 mL) was added and extracted with ethyl acetate (50 mL×2). The aqueous phase was adjusted to pH=9-10 with saturated sodium carbonate solution and extracted with ethyl acetate (60 mL×2). The organic phase was dried over anhydrous sodium sulfate, filtered, and concentrated under reduced pressure. Compound Z-62 (47.9 mg) was obtained by preparative HPLC chromatography in yield of 54.3%. MS m/z (ESI): 272.2 [M+1]. $^1$H NMR (400 MHz, DMSO-d6) δ 8.00 (s, 1H), 7.85 (s, 1H), 6.30 (d, J=2.0 Hz, 1H), 5.85 (s, 1H), 4.26-4.17 (m, 1H), 3.56-3.47 (s, 1H), 2.45-2.26 (m, 3H), 2.15-1.96 (m, 2H), 1.28 (d, J=7.2 Hz, 3H), 1.05-0.96 (m, 1H), 0.55-0.46 (m, 1H), 0.37-0.27 (m, 1H), 0.24-0.15 (m, 2H).

Example 62a: Preparation of Compound Z-62-P1

Z-62-P1

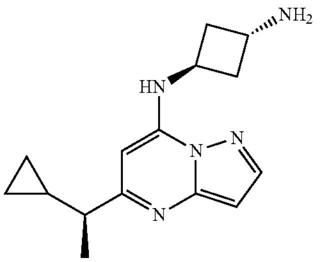

Compound Z-62 (45 mg, 165.83 μmol) was subjected to chiral resolution (resolution conditions: column type: IC-3 4.6*100 mm 3 um; co-solvents: IPA (0.5% DEA); wavelength: 220.0 nm; flow rate: 3.0 mL/min; column temperature: 40° C.) to afford compound Z-62-P1 (7.47 mg, retention time 3.394 minutes) in yield of 15.4%. MS m/z (ESI): 272.2 [M+1]. $^1$H NMR (400 MHz, DMSO-d6) δ 8.00 (d, J=2.4 Hz, 1H), 7.85 (s, 1H), 6.30 (d, J=2.4 Hz, 1H), 5.85 (s, 1H), 4.24-4.16 (m, 1H), 3.56-3.50 (m, 1H), 2.49-2.5 (m, 2H), 2.15-1.92 (m, 3H), 1.35-1.18 (m, 3H), 1.07-0.95 (m, 1H), 0.54-0.45 (m, 1H), 0.37-0.28 (m, 1H), 0.22-0.15 (m, 2H).

Example 62b: Preparation of Compound Z-62-P2

Z-62-P2

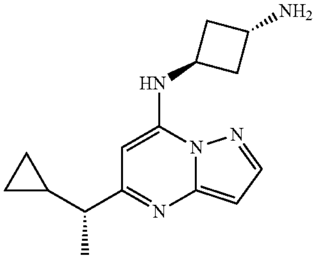

Compound Z-62 (45 mg, 165.83 μmol) was subjected to chiral resolution (resolution conditions: column type: IC-3 4.6*100 mm 3 um; co-solvents: IPA (0.5% DEA); wavelength: 220.0 nm; flow rate: 3.0 mL/min; column temperature: 40° C.) to afford compound Z-62-P2 (7.74 mg, retention time 2.850 minutes) in yield of 16.3%. MS m/z (ESI): 272.2 [M+1]. $^1$H NMR (400 MHz, DMSO-d6) δ 8.00 (d, J=2.4 Hz, 1H), 7.84 (s, 1H), 6.30 (d, J=2.4 Hz, 1H), 5.85 (s, 1H), 4.26-4.18 (m, 1H), 3.56-3.47 (m, 1H), 2.45-2.29 (m, 2H), 2.15-1.89 (m, 3H), 1.32-1.20 (m, 3H), 1.06-0.96 (m, 1H), 0.55-0.45 (m, 1H), 0.37-0.29 (m, 1H), 0.22-0.14 (m, 2H).

Example 63: Preparation of Compound Z-63

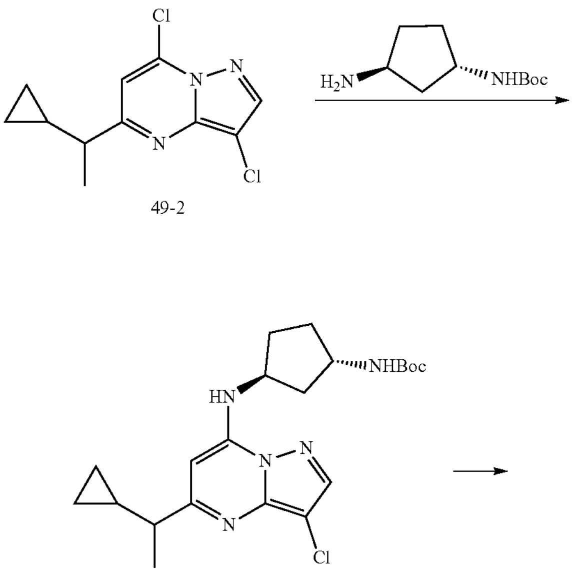

49-2

Z-63-1

-continued

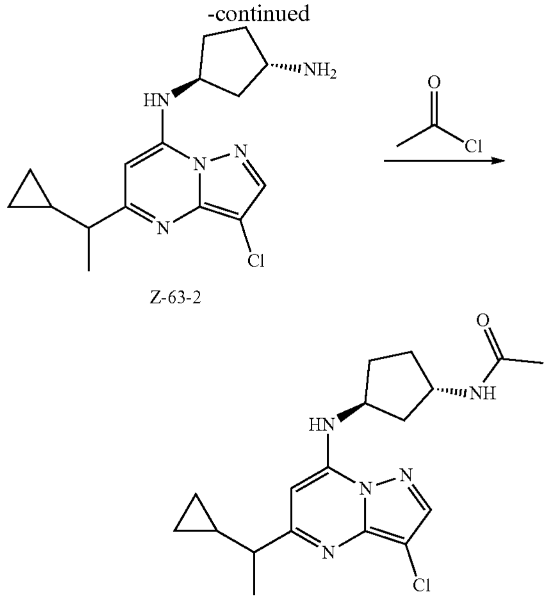

Z-63-2

Z-63

Step 1: compound 49-2 (550 mg, 2.15 mmol) and tert-butyl ((1S,3S)-3-aminocyclopentyl) carbamate (645.10 mg, 3.22 mmol) were dissolved in acetonitrile (20 mL), and potassium carbonate (890.32 mg, 6.44 mmol) was added thereto. The reaction solution was stirred at 90° C. for 16 h. The reaction was terminated, diluted with ethyl acetate (60 mL), and the organic phase was washed with saturated sodium chloride solution (60 mL), dried over anhydrous sodium sulfate, filtered, and concentrated under reduced pressure to afford the crude product Z-63-1 (850 mg, light-yellow oil) in yield of 94.3%. MS m/z (ESI): 420.2 [M+1].

Step 2: compound Z-63-1 (550 mg, 1.31 mmol) was dissolved in 1,4-dioxane (2 mL) and then added with a 4 M solution of hydrogen chloride in 1,4-dioxane (4 M, 9.82 mL). The reaction solution was stirred at room temperature for 3 h. The solvent was removed by evaporation under reduced pressure, purified water (50 mL) was added, and the impurities were extracted with ethyl acetate (50 mL). The pH was adjusted to 9-10 with aqueous ammonia solution, and extracted with ethyl acetate (60 mL×2). The organic phase was dried over anhydrous sodium sulfate, filtered, and concentrated under reduced pressure to afford compound Z-63-2 (410 mg, light-yellow oil) in yield of 97.9%. MS m/z (ESI): 320.2 [M+1].

Step 3: compound Z-63-2 (60 mg, 187.60 μmol) was dissolved in dichloromethane (10 mL), then acetyl chloride (73.63 mg, 937.99 μmol) was added, followed by adding N,N-diisopropylethyl amine (0.33 mL, 1.88 mmol). The reaction solution was stirred at room temperature for 0.5 h. The reaction was terminated, and diluted with ethyl acetate (50 mL). The organic phase was washed with saturated sodium chloride solution (50 mL), dried over anhydrous sodium sulfate, filtered, and concentrated under reduced pressure to afford the crude product. The residue was subjected to preparative HPLC chromatography to afford compound Z-63 (47.0 mg) in yield of 67.9%. MS m/z (ESI): 362.2 [M+1]. $^1$H NMR (400 MHz, DMSO-d6) δ 8.15 (s, 1H), 7.90-7.83 (m, 2H), 6.14 (s, 1H), 4.25-4.14 (m, 2H), 2.21-2.12 (m, 1H), 2.08-1.95 (m, 3H), 1.90-1.81 (m, 1H), 1.72 (s, 3H), 1.74-1.65 (m, 1H), 1.47-1.36 (m, 1H), 1.31 (d, J=6.8 Hz, 3H), 1.11-1.02 (m, 1H), 0.55-0.47 (m, 1H), 0.39-0.31 (m, 1H), 0.25-0.17 (m, 2H).

Example 64a: Preparation of Compound Z-64-P1

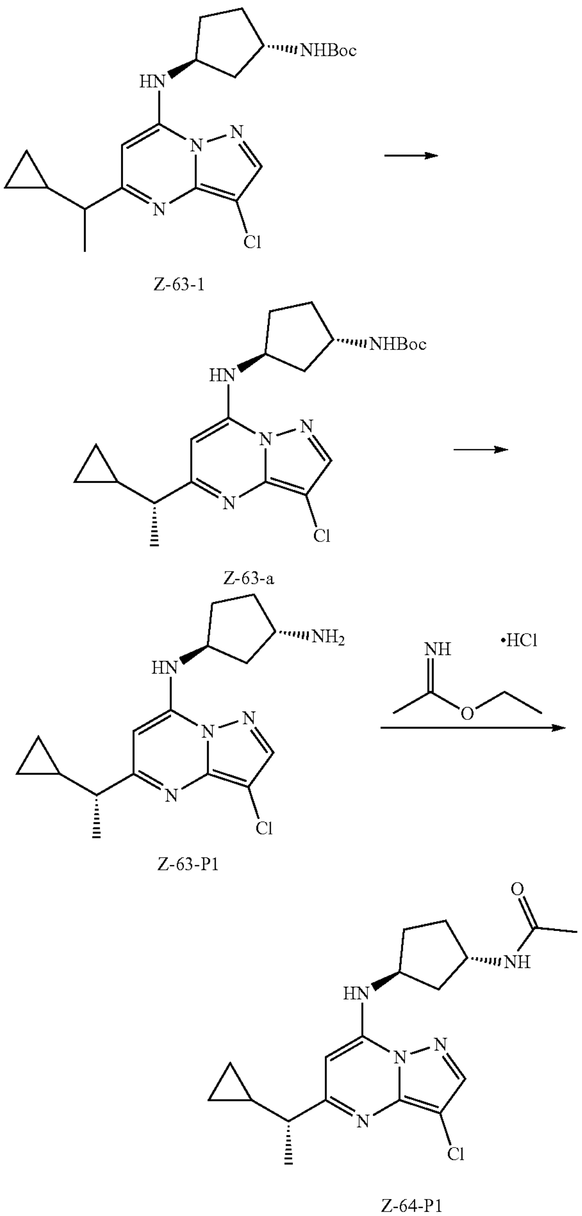

Z-63-1

Z-63-a

Z-63-P1

Z-64-P1

Step 1: 1.2 g of the compound Z-63-1 was resolved by supercritical fluid chromatography (SFC) (column type: AD-3 4.6*100 mm 3 μm, co-solvent: EtOH [1% $NH_3$(7 M in MeOH)], injection volume: 1.00 μl, run time: 4.0 minutes, flow rate: 3.0 mL/min, pressure: 2000 psi, column temperature: 40° C.) to obtain 440 mg of compound Z-63-a (retention time 1.329 minutes).

Step 2: compound Z-63-a (170.00 mg, 404.81 μmol) was dissolved in 1,4-dioxane (2 mL), then added with a solution of hydrogen chloride/1,4-dioxane (4 M, 6.07 mL), and the mixture was stirred at room temperature for 3 h. The solvent was evaporated under reduced pressure to afford crude compound Z-63-P1 (120 mg, light-yellow solid hydrochloride) in yield of 92.68%. MS m/z (ESI): 320.2 [M+1].

Step 3: compound Z-63-P1 (120 mg, 375.20 μmol) and ethyl acetamidate (163.44 mg, 1.88 mmol) were dissolved in acetonitrile (15 mL), and N,N-diisopropylethyl amine (0.65 mL, 3.75 mmol) was added thereto. The reaction solution was stirred at 80° C. for 2 h, cooled to room temperature, added with 7N methanolic ammonia solution of 2 mL, and stirred at room temperature for 1 h. The reaction was terminated and diluted with ethyl acetate (50 mL). The organic phase was washed with saturated sodium chloride solution (50 mL), dried over anhydrous sodium sulfate, filtered, and concentrated under reduced pressure. The residue was purified with preparative liquid chromatography (preparative column: 21.2×250 mm C18 column; system: 10 mM $NH_4HCO_3H_2O$; wavelength: 254/214 nm; gradient: 5%-95% acetonitrile change) to afford compound Z-64-P1 (63.5 mg) in yield of 46.2%. MS m/z (ESI): 361.2 [M+1]. $^1H$ NMR (400 MHz, DMSO-d6) δ 8.17 (s, 1H), 6.17 (s, 1H), 4.30-4.15 (m, 1H), 3.99-3.89 (m, 1H), 2.26-2.17 (m, 1H), 2.12-1.93 (m, 3H), 1.89-1.70 (m, 4H), 1.70-1.60 (m, 1H), 1.50-1.38 (m, 1H), 1.33 (d, J=6.8 Hz, 3H), 1.10-1.02 (m, 1H), 0.57-0.48 (m, 1H), 0.42-0.31 (m, 1H), 0.28-0.17 (m, 2H).

Example 64b: Preparation of Compound Z-64-P2

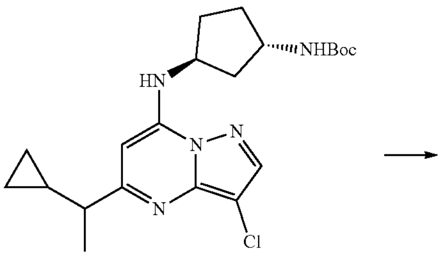

Z-63-1

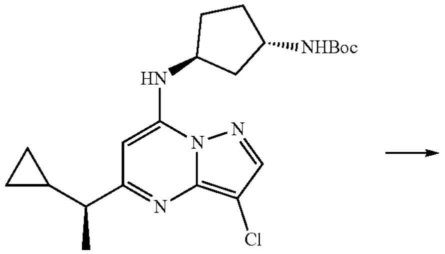

Z-63-b

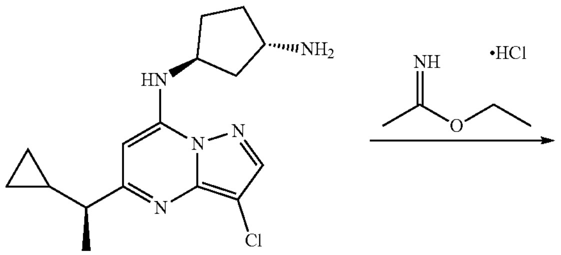

Z-63-P2

-continued

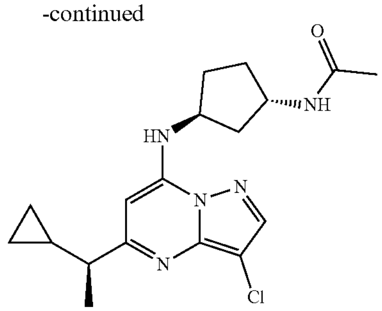

Z-64-P2

Step 1: 1.2 g of the compound Z-63-1 was resolved by supercritical fluid chromatography (SFC) (column type: AD-3 4.6*100 mm 3 μm, co-solvent: EtOH [1% $NH_3$(7 M in MeOH)], injection volume: 5.00 μl, run time: 6.0 minutes, flow rate: 3.0 mL/min, pressure: 2000 psi, column temperature: 40° C.) to obtain 440 mg of compound Z-63-b (retention time: 1.512 minutes).

Step 2: compound Z-64-P2 was prepared with reference to step 2 and step 3 of Example 64a. MS m/z (ESI): 361.2 [M+1]. $^1H$ NMR (400 MHz, DMSO-d6) δ 8.17 (s, 1H), 6.16 (s, 1H), 4.24-4.12 (m, 1H), 3.98-3.88 (m, 1H), 2.27-2.16 (m, 1H), 2.12-1.92 (m, 3H), 1.86-1.71 (m, 4H), 1.70-1.60 (m, 1H), 1.50-1.38 (m, 1H), 1.33 (d, J=6.8 Hz, 3H), 1.12-1.02 (m, 1H), 0.56-0.48 (m, 1H), 0.41-0.30 (m, 1H), 0.28-0.18 (m, 2H).

Example 65 Preparation of Compound Z-65

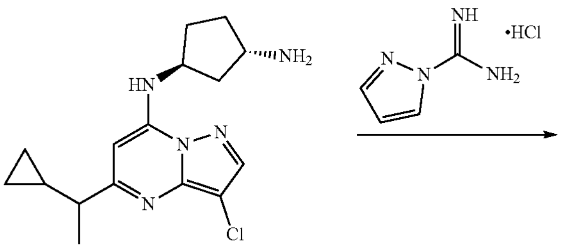

Z-63-2

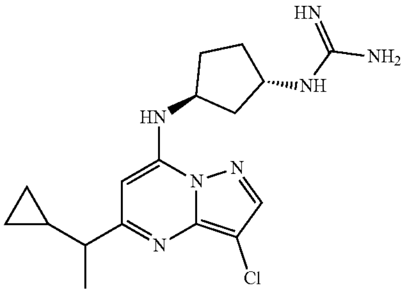

Z-65

Compound Z-63-2 (60 mg, 187.60 μmol) and 1H-pyrazole-1-carboxamidine hydrochloride (620 mg, 4.23 mmol) were dissolved in acetonitrile (12 mL), and N,N-diisopropylethyl amine (1.31 mL, 7.50 mmol) was added. The reaction solution was stirred at room temperature for 16 h. The reaction was terminated, saturated sodium chloride solution (30 mL) was added, and the mixture was extracted with ethyl acetate (30 mL×2). The organic phase was dried over anhydrous sodium sulfate, filtered, and concentrated under reduced pressure. Target product compound Z-65 (26.21 mg) was obtained by preparative HPLC chromatography in yield of 36.68%. MS m/z (ESI): 362.1 [M+1]. $^1$H NMR (400 MHz, DMSO-d6) δ7.96 (s, 1H), 7.60 (s, 1H), 5.99 (d, J=2.8 Hz, 1H), 4.10-4.00 (m, 1H), 3.85-3.70 (m, 1H), 2.09-1.77 (m, 4H), 1.75-1.60 (m, 1H), 1.55-1.46 (m, 1H), 1.36-1.25 (m, 1H), 1.07 (d, J=6.8 Hz, 3H), 0.92-0.75 (m, 1H), 0.33-0.25 (m, 1H), 0.17-0.08 (m, 1H), 0.05-0.01 (m, 2H). Example 66 to Example 74

Compounds Z-66, Z-68, Z-69, Z-72, and Z-73 were prepared with reference to the schemes of Example 64a. Compounds Z-67 and Z-71 were prepared by with reference to the schemes of Example 65. Compounds Z-70 and Z-74 were prepared by with reference to the schemes of Example 1.

| Example No. | Structure | $^1$H NMR and MS |
| --- | --- | --- |
| 66 | 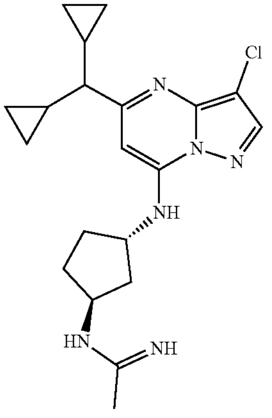 Z-66 | MS m/z (ESI): 387.1 [M + 1] $^1$H NMR (400 MHz, DMSO-d6) δ 8.18 (s, 1H), 7.90 (d, J = 7.6 Hz, 2H), 6.14 (s, 1H), 4.15-4.27 (m, 2H), 2.22-2.12 (m, 1H), 2.08-1.96 (m, 2H), 1.92-1.83 (m, 1H), 1.83-1.62 (m, 4H), 1.49-1.30 (m, 2H), 1.29-1.18 (m, 2H), 0.62-0.47 (m, 2H), 0.41-0.25(m, 4H), 0.18-0.05 (m, 2H). |
| 67 | 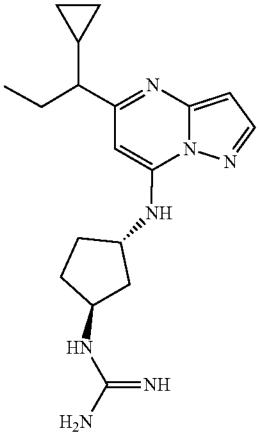 Z-67 | MS m/z (ESI): 342 [M + 1] $^1$H NMR (400 MHz, DMSO-d6) δ 8.02 (d, J = 2.0 Hz, 1H), 7.63 (s, 3H), 6.33 (d, J = 2.0 Hz, 1H), 6.05 (d, J = 2.4 Hz, 1H), 4.23 (s, 1H), 4.01 (s, 1H), 2.32-2.20 (m, 3H), 1.96-1.85 (m, 2H), 1.81-1.76 (m, 2H), 1.70 (s, 1H), 1.52 (s, 1H), 1.06 (s, 1H), 0.81 (t, J = 6.8 Hz, 3H), 0.63-0.48 (m, 1H), 0.29-0.21 (m, 2H), 0.18-0.03 (m, 1H). |
| 68 | 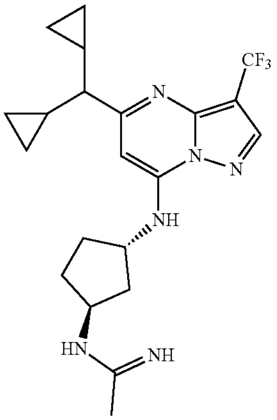 Z-68 | MS m/z (ESI): 421.1 [M + 1] $^1$H NMR (400 MHz, DMSO-d6) δ 8.39 (s, 1H), 6.31 (s, 1H), 4.26-4.17(m, 1H), 3.95-3.88 (m, 1H), 2.25-2.17 (m, 1H), 2.10-2.00 (m, 2H), 1.79 (s, 3H), 1.71-1.59 (m, 2H), 1.47-1.35 (m, 2H), 1.21 (s, 2H), 0.57-0.50(m, 2H), 0.40-0.22 (m, 4H), 0.12-0.06(m, 2H). |

-continued
| Example No. | Structure | $^1$H NMR and MS |
|---|---|---|
| 69 | 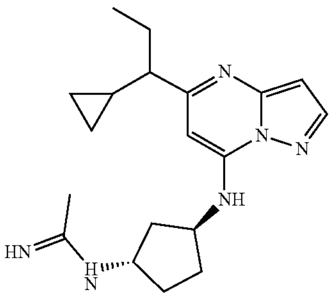 Z-69 | MS m/z (ESI): 341 [M + 1] $^1$H NMR (400 MHz, DMSO-d6) δ 7.99 (d, J = 2.0 Hz, 1H), 7.55 (s, 1H), 6.30 (d, J = 2.0 Hz, 1H), 6.00 (s, 1H), 4.19 (s, 1H), 3.98-3.95 (m, 2H), 2.29-2.15 (m, 1H), 2.09-2.07 (m, 2H), 1.87 (s, 4H), 1.78-1.69 (m, 2H), 1.67-1.62 (m, 1H), 1.49-1.44 (m, 1H), 1.21 (s, 1H), 1.03-1.02 (m, 1H), 0.79 (t, J = 6.8 Hz, 3H), 0.58-0.47 (m, 1H), 0.32-0.16 (m, 2H), 0.11 (s, 1H). |
| 70 | 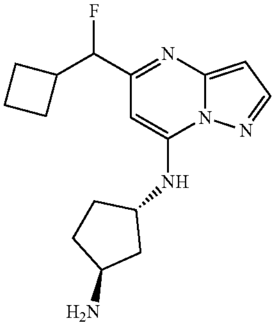 Z-70 | MS m/z (ESI): 304.1 [M + 1] $^1$H NMR (400 MHz, DMSO-d6) δ 8.05 (d, J = 2.4 Hz, 1H), 6.78-6.88 (m, 1H), 6.37 (d, J = 2.4 Hz, 1H), 6.15 (d, J = 10.8 Hz, 1H), 5.32 (dd, J = 48.8, 6.0 Hz, 1H), 4.19-4.29 (m, 1H), 3.48-3.39 (m, 1H), 2.99-2.81 (m, 1H), 2.10-2.22 (m, 1H), 2.11-1.75 (m, 9H), 1.73-1.59 (m, 1H), 1.25-1.50 (m, 1H). |
| 71 | 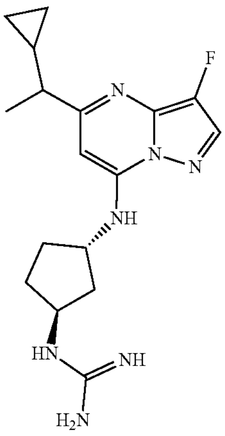 Z-71 | MS m/z (ESI): 346.1 [M + 1] $^1$H NMR (400 MHz, DMSO-d6) δ 8.15 (d, J = 3.2 Hz, 1H), 7.78 (s, 1H), 6.11 (s, 1H), 4.28-4.17 (m, 1H), 4.05-3.95 (s, 1H), 2.35-1.95 (m, 4H), 1.96-1.82 (m, 1H), 1.73-1.62 (m, 1H), 1.56-1.45 (m, 1H), 1.30 (d, J = 7.2 Hz, 3H), 1.09-1.01 (m, 1H), 0.55-0.45 (m, 1H), 0.39-0.30(m, 1H), 0.27-0.15 (m, 2H). |

-continued
| Example No. | Structure | $^1H$ NMR and MS |
|---|---|---|
| 72 | 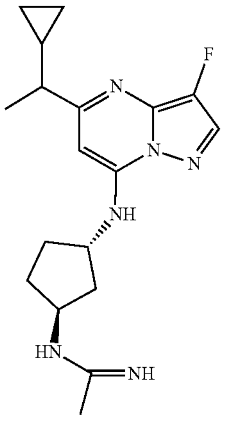 Z-72 | MS m/z (ESI): 345.1 [M + 1] $^1H$ NMR (400 MHz, DMSO-d6) δ 8.16 (d, J = 3.6 Hz, 1H), 7.80 (s, 1H), 6.9 (s, 1H), 4.28-4.13 (m, 1H), 3.99-3.87 (m, 1H), 2.30-2.15 (m, 1H), 2.14-2.05 (m, 3H), 1.94-1.73 (m, 4H), 1.73-1.57 (m, 1H), 1.56-1.38 (m, 1H), 1.29 (d, J = 7.2 Hz, 3H), 1.12-0.99 (m, 1H), 0.56-0.45 (m, 1H), 0.41-0.30 (m, 1H), 0.27-0.16 (m, 2H). |
| 73 | 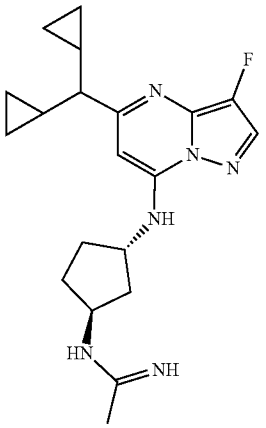 Z-73 | MS m/z (ESI): 371.2 [M + 1] 1H NMR (400 MHz, DMSO-d6) δ 8.15 (d, J = 3.6 Hz, 1H), 7.68 (s, 1H), 6.05 (s, 1H), 4.27-4.10 (m, 1H), 3.94 (s, 1H), 2.20-2.17 (m, 1H), 2.07-2.02 (m, 2H), 1.80 (s, 4H), 1.65-1.61 (m, 1H), 1.47-1.37 (m, 1H), 1.34-1.28 (m, 1H), 1.25-1.17 (m, 2H), 0.56-0.50 (m, 2H), 0.31-0.26 (m, 4H), 0.13-0.05 (m, 2H). |
| 74 | 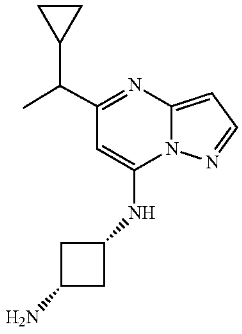 Z-74 | MS m/z (ESI): 272.2 [M + 1] $^1H$ NMR (400 MHz, DMSO-d6) δ 8.01 (d, J = 2.0 Hz, 1H), 7.76 (s, 1H), 6.32 (d, J = 2.4 Hz, 1H), 6.00 (s, 1H), 4.00-3.70 (m, 2H), 2.79-2.64 (m, 2H), 2.18-1.77 (m, 3H), 1.30 (d, J = 6.8 Hz, 3H), 1.10-0.93 (m, 1H), 0.62-0.42 (m, 1H), 0.42-0.29 (m, 1H), 0.29-0.12 (m, 2H). |

Preparation of Comparative Compound D and Compound E

D

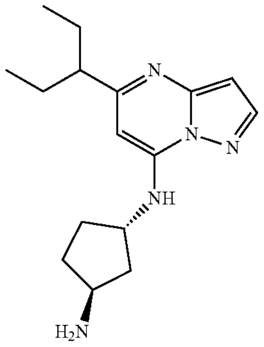

E

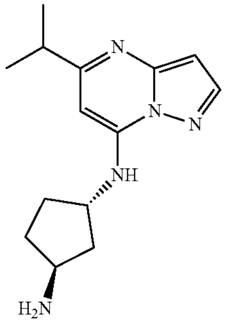

Compound D and compound E were prepared with reference to the published patent literature.

Test Example 1: Activity Inhibition Assay on CDK Family Kinases

In the following LANCE Ultra test methods, kinase reagents were purchased from Carna Bioscience, reaction substrates and detection reagents were purchased from PerkinElmer, and the remaining reagents were purchased from Thermo scientific.

The inhibiting effects on the kinase activity of CDK1/CycB (Carna bioscience, #04-102), CDK2/CycA (Carna bioscience, #04-103) and CDK9/CycT (Carna bioscience, #04-110) were determined by using LANCE Ultra method.

The kinase activity test was performed using a system (10 μL) containing the following components: substrate diluent prepared by mixing CDK kinase diluent, Ulight-Myelic basic protein (Perkin Elmer, #TRF-0109, hereinafter referred to as U-MBP) and ATP (Thermo scientific, #PV3227); and the compounds (i.e., analyte) prepared in the examples of the present disclosure. The assay for each kinase includes three test groups, i.e., a background group (Blank), a non-inhibition group (PC), and compound testing group (Test). The components included in each test group were as follows:

| | Kinase | Substrate | Compound |
|---|---|---|---|
| Blank | 1.33 × reaction buffer | Substrate diluent | 2% DMSO only |
| PC | Kinase diluent | Substrate dilution | 2% DMSO only |
| Test | Kinase diluent | Substrate dilution | Compound diluent |

Working concentrations of the respective components of the Test groups in different kinase reactions were as follows.

Compounds: 10 mM of the compound to be tested was dissolved at room temperature and diluted with DMSO to gradient concentrations, followed by diluting with deionized water to prepare a 4× working solution of the compound, and the content of DMSO was 2%. The highest concentration of compound used in the CDK1 and CDK2 assays was 10 μM, and that in CDK9 assay was 1 μM.

1.33× reaction buffer: the components include 26.7 mM of MOPS, 6.67 mM of $MgCl_2$, and 0.0133% Tween-20, which were stored in a 4° C. refrigerator and protected from light after preparation. Freshly prepared DTT was added to a final concentration of 5.33 mM before use.

| Component | Kinase | U-MBP | ATP | 4 × compound |
|---|---|---|---|---|
| Solvent | 1.33 × reaction buffer | 1.33 × reaction buffer | | 2% DMSO |
| Volume | 2.5 μL | 5 μL | | 2.5 μL |
| CDK1 | 0.1 ng/μL | 12.5 nM | 4 μM | Gradient dilution |
| CDK2 | 0.25 ng/μL | 12.5 nM | 10 μM | Gradient dilution |
| CDK9 | 1.25 ng/μL | 12.5 nM | 10 μM | Gradient dilution |

The working concentration of DMSO in the reaction was 0.5%.

The above-mentioned components, after being mixed, were placed on a shaker and incubated at room temperature in the dark for 1 h. 10 μL of test solution was then added to all test groups (including Blank, PC and Test groups).

10 μL of test solution contains the following components: 16 mM of EDTA (Thermo scientific, #15575), 1 nM of phosphorylated U-MBP protein antibody (Perkin Elmer, #TRF-0201), and 1× detection damping fluid (Perkin Elmer, #CR97-100).

After the test solution was added, the solution was placed on a shaker and continually incubated at room temperature for 1 h in the dark. At the end of incubation, Victor X5 fluorescence microplate reader of Perkin Elmer was used to read the signal; the wavelength of excitation light was 320 nm, and the wavelengths of emission light were 615 nm and 665 nm. The inhibition rate was calculated as below.

1. For all groups, a value of 665 nm/615 nm (hereinafter referred to as Ratio) was calculated, and an inhibition rate was calculated based on the Ratio of each group;
2. Inhibition rate=($PC_{Ratio}$-$Test_{Ratio}$)/($PC_{Ratio}$-$Blank_{Ratio}$) *100%; and
3. XLFIT 5.0 software (IDBS, UK) was used to fit a graph by using the logarithmic value of the compound concentration as the X-axis and the inhibition rater as the Y-axis, and a four-parameter model was used to calculate the half inhibitory concentration $IC_{50}$ of the compound.

TABLE 1

Inhibitory activity of compounds on CDK9

| Compound No. | CDK9 ($IC_{50}$/μM) |
|---|---|
| Z-1 | 0.018 |
| Z-2 | 0.006 |
| Z-3 | 0.073 |
| Z-4 | 0.014 |
| Z-5 | 0.017 |

TABLE 1-continued

Inhibitory activity of compounds on CDK9

| Compound No. | CDK9 ($IC_{50}$/μM) |
|---|---|
| Z-5-1 | 0.023 |
| Z-5-2 | 0.007 |
| Z-9 | 0.008 |
| Z-11 | 0.022 |
| Z-11-P1 | 0.012 |
| Z-11-P2 | 0.030 |
| Z-12 | 0.020 |
| Z-13 | 0.018 |
| Z-14 | 0.042 |
| Z-15 | 0.005 |
| Z-16 | 0.022 |
| Z-17 | 0.060 |
| Z-18 | 0.033 |
| Z-19 | 0.092 |
| Z-20 | 0.034 |
| Z-21 | 0.029 |
| Z-22 | 0.013 |
| Z-24 | 0.084 |
| Z-25 | 0.021 |
| Z-26 | 0.026 |
| Z-26-P1 | 0.005 |
| Z-26-P2 | 0.078 |
| Z-27 | 0.009 |
| Z-27-P1 | 0.047 |
| Z-27-P2 | 0.008 |
| Z-28 | 0.011 |
| Z-28-P1 | 0.006 |
| Z-28-P2 | 0.012 |
| Z-29 | 0.011 |
| Z-30 | 0.010 |
| Z-30-P1 | 0.010 |
| Z-30-P2 | 0.022 |
| Z-31 | 0.104 |
| Z-32 | 0.009 |
| Z-32-P1 | 0.099 |
| Z-32-P2 | 0.056 |
| Z-33 | 0.006 |
| Z-34 | 0.036 |
| Z-35 | 0.018 |
| Z-36 | 0.006 |
| Z-37 | 0.027 |
| Z-38 | 0.017 |
| Z-38-P1 | 0.040 |
| Z-38-P2 | 0.016 |
| Z-39 | 0.034 |
| Z-40 | 0.048 |
| Z-41-P1 | 0.047 |
| Z-41-P2 | 0.013 |
| Z-42 | 0.022 |
| Z-43 | 0.056 |
| Z-44 | 0.082 |
| Z-46 | 0.010 |
| Z-47 | 0.035 |
| Z-48 | 0.068 |
| Z-49 | 0.062 |
| Z-50 | 0.064 |
| Z-51 | 0.065 |
| Z-52 | 0.032 |
| Z-53 | 0.047 |
| Z-54 | 0.016 |
| Z-55 | 0.015 |
| Z-56 | 0.013 |
| Z-57 | 0.058 |
| Z-58 | 0.020 |
| Z-60 | 0.024 |
| Z-61 | 0.034 |
| Z-62 | 0.017 |
| Z-62-P1 | 0.010 |
| Z-62-P2 | 0.024 |
| Z-63 | 0.014 |
| Z-64 | 0.015 |
| Z-64-P1 | 0.064 |
| Z-64-P2 | 0.011 |
| Z-65 | 0.019 |
| Z-66 | 0.018 |
| Z-67 | 0.044 |

TABLE 1-continued

Inhibitory activity of compounds on CDK9

| Compound No. | CDK9 ($IC_{50}$/μM) |
|---|---|
| Z-68 | 0.025 |
| Z-69 | 0.058 |
| Z-70 | 0.023 |
| Z-71 | 0.028 |
| Z-72 | 0.020 |
| Z-73 | 0.018 |
| Z-74 | 0.417 |

TABLE 2

Inhibitory activity of compounds on CDK1 and CDK2

| Compound No. | CDK1 ($IC_{50}$/μM) | CDK2 ($IC_{50}$/μM) |
|---|---|---|
| Z-1 | 1.962 | 5.645 |
| Z-2 | 0.161 | 0.191 |
| Z-3 | >10 | >10 |
| Z-4 | 0.716 | 0.828 |
| Z-5 | 2.195 | 3.987 |
| Z-5-1 | 1.427 | 9.126 |
| Z-5-2 | 0.838 | 0.887 |
| Z-9 | 1.039 | 1.553 |
| Z-11 | 1.836 | 9.41 |
| Z-11-P1 | 1.887 | 3.577 |
| Z-11-P2 | 0.973 | >10 |
| Z-12 | 2.717 | >10 |
| Z-13 | 1.335 | 7.617 |
| Z-14 | 1.606 | 2.549 |
| Z-15 | 0.293 | 0.367 |
| Z-16 | 1.275 | 1.272 |
| Z-17 | 8.449 | >10 |
| Z-18 | 4.202 | >10 |
| Z-19 | >10 | >10 |
| Z-20 | 2.422 | 4.39 |
| Z-21 | 4.367 | 3.291 |
| Z-22 | 1.767 | 8.641 |
| Z-24 | 2.533 | 2.923 |
| Z-25 | 9.874 | 8.706 |
| Z-26 | 3.916 | 7.058 |
| Z-26-P1 | 1.622 | 1.801 |
| Z-26-P2 | >10 | >10 |
| Z-27 | 0.772 | 2.816 |
| Z-27-P1 | 1.21 | >10 |
| Z-27-P2 | 2.084 | 2.782 |
| Z-28 | 1.861 | 3.074 |
| Z-28-P1 | 2.048 | 4.511 |
| Z-28-P2 | 2.393 | >10 |
| Z-29 | 1.891 | 2.056 |
| Z-30 | 1.362 | 1.547 |
| Z-30-P1 | 1.122 | 0.968 |
| Z-30-P2 | 3.536 | 4.905 |
| Z-31 | 3.215 | 6.392 |
| Z-32 | 0.996 | 0.967 |
| Z-32-P1 | >10 | >10 |
| Z-32-P2 | 8.217 | 6.819 |
| Z-33 | 0.347 | 0.355 |
| Z-34 | 8.089 | >10 |
| Z-35 | 1.504 | 1.56 |
| Z-36 | 0.924 | 2.112 |
| Z-37 | 7.178 | >10 |
| Z-38 | 1.465 | 2.914 |
| Z-38-P1 | 4.206 | 9.074 |
| Z-38-P2 | 1.763 | 2.479 |
| Z-39 | 2.476 | >10 |
| Z-40 | >10 | >10 |
| Z-41-P1 | 4.591 | >10 |
| Z-41-P2 | 2.966 | 3.766 |
| Z-42 | 3.301 | 8.5 |
| Z-43 | 7.103 | >10 |
| Z-44 | >10 | >10 |
| Z-46 | 1.147 | 1.805 |
| Z-47 | 1.042 | 1.905 |
| Z-48 | 1.469 | 2.218 |

TABLE 2-continued

| Inhibitory activity of compounds on CDK1 and CDK2 | | |
|---|---|---|
| Compound No. | CDK1 ($IC_{50}$/μM) | CDK2 ($IC_{50}$/μM) |
| Z-49 | >10 | >10 |
| Z-50 | 6.572 | >10 |
| Z-51 | 7.761 | 7.747 |
| Z-52 | 7.153 | 6.15 |
| Z-53 | 4.855 | >10 |
| Z-54 | 2.16 | 2.649 |
| Z-55 | 1.941 | 1.905 |
| Z-56 | 2.483 | 3.776 |
| Z-57 | 4.968 | >10 |
| Z-58 | 5.306 | >10 |
| Z-59 | 8.823 | >10 |
| Z-60 | 2.49 | 3.195 |
| Z-61 | >10 | >10 |
| Z-62 | 1.545 | 4.722 |
| Z-62-P1 | 1.71 | 1.973 |
| Z-62-P2 | 1.817 | >10 |
| Z-63 | 0.84 | 0.278 |
| Z-64 | 2.305 | 3.456 |
| Z-64-P1 | 8.85 | 8.687 |
| Z-64-P2 | 2.092 | 1.229 |
| Z-65 | 1.238 | 2.302 |
| Z-66 | 0.995 | 0.332 |
| Z-67 | 4.589 | >10 |
| Z-68 | 3.467 | 4.676 |
| Z-69 | >10 | >10 |
| Z-70 | 2.259 | 3.879 |
| Z-71 | 1.884 | 4.532 |
| Z-72 | 4.889 | 6.571 |
| Z-73 | 2.566 | 3.678 |
| Z-74 | >10 | >10 |

Table 1 and Table 2 reveal that the compounds according to the examples of the present disclosure have a relatively higher inhibitory activity against CDK9 and a relatively higher inhibitory selectivity on CDK9.

Test Example 2: In Vivo Pharmacokinetics in Mice

To investigate the pharmacokinetic behaviors of the compounds according to the present disclosure in mice and evaluate the pharmacokinetic characteristics thereof, the plasma concentrations of the compounds according to the present disclosure in mice at different time points after intravenous injection and intragastric administration of the compounds were determined by LC/MS/MS.

Experimental Protocol:

Experimental animals: healthy adult male ICR mice (12 mice with body weight of 30-40 g, free water and diet for intravenous injection group, and fasted overnight for intragastric administration group, free water and diet after 4 hours of administration) were provided by Beijing Vital River Laboratory Animal Co. LTD;

Administration route and dosage: the ICR mice were administrated intravenously via the tail vein (2 mg/kg, 5% DMSO, pH 4.5 20% Captisol) and intragastrically (10 mg/kg, 5% DMSO, pH 4.5 20% Captisol).

Blood sample collection: prior to the administration, animals satisfying the experimental requirements were selected, weighed and marked. Before collecting blood samples, the mice were tied together, and the blood of each administrated mouse was collected at the respective scheduled time points (for the intravenous administration, the blood was collected at 0.083 h, 0.25 h, 0.5 h, 1 h, 2 h, 4 h, 6 h, 7.5 h, and 24 h after the administration, respectively, for a total of 9 time points; for the intragastric administration, the blood was collected at 0.083 h, 0.25 h, 0.5 h, 1 h, 2 h, 4 h, 6 h, 7.5 h, and 24 h after the administration, respectively, for a total of 9 time points), about 100 μL of blood was collected from orbit. The blood was transferred to a 1.5 mL tube, which was pre-filled with $K_2$EDTA, centrifuged for 4 minutes (8000 rpm, 4° C.), and the plasma removed within 15 minutes, which all the steps were finished in 15 minutes after the collection of blood samples. All samples were stored in −20° C. refrigerator before sample analysis. The drug concentrations were determined using the LC/MS/MS method, the pharmacokinetic parameters of the compounds of some examples of the present disclosure in mice at the same dosage and administration routes were lists in Table 3:

TABLE 3

| Pharmacokinetic parameters of compounds in mice | | | | | | | | |
|---|---|---|---|---|---|---|---|---|
| | Compound No. | | | | | | | |
| Pharmacokinetic parameters | D | E | Z-5-2 | Z-9 | Z-11-P1 | Z-32-P2 | Z-56 | Z-62-P1 |
| Oral maximum plasma concentration $C_{max}$(ng/mL) | 433 | 395 | 690 | 740 | 379 | 696 | 409 | 786 |
| Area under the oral curve $AUC_{0-t}$ (hr*ng/mL) | 1191 | 953 | 1702 | 7860 | 2957 | 9414 | 6092 | 2064 |

Test Example 3: In Vivo Pharmacodynamic Assay

In vivo pharmacodynamic assays were performed on (CDX)BALB/c nude mice implanted subcutaneously with MV4-11 acute myeloid leukemia patient-derived xenografts derived from human tumor cell lines.

Experimental protocol: BALB/c nude mice, female, 6-10 weeks old, with weight of approximately 20-23 grams, were maintained in a specific pathogen-free environment, 5 mice in each cage, and 2 cages with 10 mice as one group. All the cages, bedding and water were disinfected before use. All animals had free access to a standard certified commercial laboratory diet. A total of 80 mice were purchased from the Laboratory Animal Management Department of Shanghai Institute of Family Planning Science (No. 3577 Jinke Road, Pudong, Shanghai) for the study. Each mouse was implanted subcutaneously with tumor cells ($1\times10^7$ 0.1 ml+Matrigel 0.1 ml) in the right flank for tumor growth. When the mean tumor volume reached approximately 165 $mm^3$, the tumors were randomly grouped according to body weight and tumor volume, and the administration of the compounds began. Test compounds were administered via oral gavage daily. Antitumor efficacy was determined by dividing the mean tumor volume increase of the animals treated with the compound by the mean tumor volume increase of untreated animals.

Tumor volumes were measured twice a week with two-dimensional calipers, and volumes were measured in cubic millimeters. Tumor volume $TV=0.5a\times b^2$, where a represent a long diameter of the tumor and b represents a short diameter of the tumor.

Relative tumor proliferation rate T/C (%), i.e., a percentage value of relative tumor volume of treatment group to relative tumor volume of control group at a certain time point, can be calculated based on an equation of T/C $\%=T_{RTV}/C_{RTV}\times100$ ($T_{RTV}$: mean RTV in treatment group; $C_{RTV}$: mean RTV in solvent control group; $RTV=V_t/V_0$, $V_0$ being the tumor volume of the animal at the time of grouping, Vt being the tumor volume of the animal after treatment).

Body weight change (%) of tumor-bearing animals was calculated as follows:

(weight at measurement−weight at grouping)/weight at grouping×100.

TABLE 4

In vivo tumor inhibition results of compounds in mice

| Compound No. | Dosage and administration route | Average tumor weight (g) | SEM | T/C(%) |
|---|---|---|---|---|
| Vehicle control group | Oral, once a day | 0.79 | 0.13 | — |
| Compound D | 12.5 mpk, oral, once a day | 0.35 | 0.09 | 45.04 |
| Z-11-P1 | 12.5 Mpk, oral, once a day | 0.17 | 0.06 | 21.50 |
| Compound D | 25 mpk, oral, once a day | 0.02 | 0.08 | 2.04 |
| Z-11-P1 | 25 mpk, oral, once a day | 0.01 | 0.00 | 1.40 |

TABLE 5

In vivo tumor inhibition results of compounds in mice

| Compound No. | Dosage and administration route | Average tumor weight (g) | SEM | T/C(%) |
|---|---|---|---|---|
| Vehicle control group | Oral, once a day | 1.21 | 0.19 | — |
| Compound D | 12.5 mpk, oral, once a day | 0.43 | 0.11 | 35.91 |
| Z-5-2 | 5 mpk, oral, once a day | 0.72 | 0.20 | 59.25 |
| Compound D | 25 mpk, oral, once a day | 0.04 | 0.20 | 2.90 |
| Z-5-2 | 10 mpk, oral, once a day | 0.04 | 0.04 | 3.45 |

All documents mentioned herein were incorporated herein by reference as if each document was individually incorporated by reference. Furthermore, it can be understood that those skilled in the art, upon reading the teachings, can make various changes and modifications to the present disclosure, and such equivalents were intended to fall within the scope of the appended claims.

What is claimed is:

1. A compound represented by formula (III-a) or formula (III-b), or a pharmaceutically acceptable salt thereof, or a stereoisomer thereof, or a solvate thereof:

(III-a)

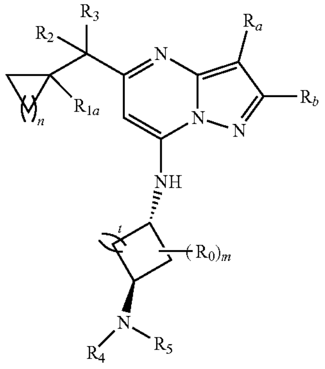

or

-continued (III-b)

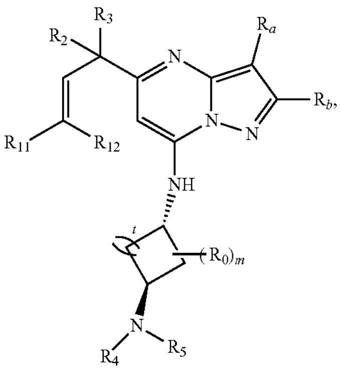

, wherein:

$R_{1a}$ is hydrogen;

n is 1 or 2;

t is 1 or 2;

$R_{11}$ and $R_{12}$ are each independently hydrogen;

$R_2$ is hydrogen or $C_{1-6}$ alkyl;

$R_3$ is $C_{1-6}$ alkyl or $C_{3-6}$ cycloalkyl, wherein the $C_{1-6}$ alkyl is unsubstituted;

$R_4$ is hydrogen;

$R_5$ is hydrogen;

$R_a$ is hydrogen, $C_{1-6}$ alkyl, or halogen, wherein the $C_{1-6}$ alkyl is unsubstituted;

$R_b$ is hydrogen;

$(R_0)_m$ is absent.

2. The compound, or the pharmaceutically acceptable salt thereof, or the stereoisomer thereof, or the solvate thereof according to claim 1, wherein the compound has a structure represented by formula (III-a):

(III-a)

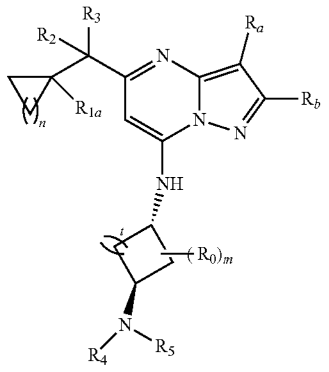

wherein:

$R_{1a}$ is hydrogen;

n is 1 or 2;

t is 2;

$R_2$ is hydrogen;

$R_3$ is $C_{1-3}$ alkyl or $C_{3-6}$ cycloalkyl, wherein the $C_{1-3}$ alkyl is unsubstituted; and $R_a$ is hydrogen or $C_{1-3}$ alkyl, wherein the $C_{1-3}$ alkyl is unsubstituted.

3. The compound, or the pharmaceutically acceptable salt thereof, or the stereoisomer thereof, or the solvate thereof according to claim 2, wherein the compound represented by formula (III-a) has a structure represented by formula (III-a-1) or formula (III-a-2):

(III-a-1)

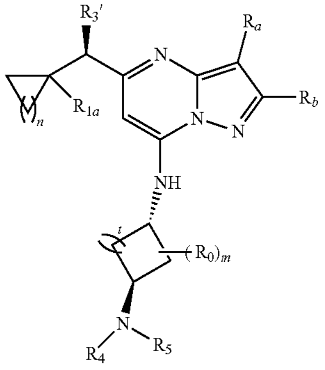

(III-a-2)

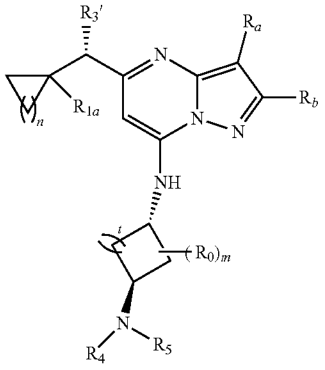

wherein:

$R_{3'}$ is $C_{1-3}$ alkyl;

$R_{1a}$ is hydrogen;

n is 1 or 2;

t is 2;

$R_4$ is hydrogen;

$R_a$ is hydrogen or $C_{1-3}$ alkyl, wherein the $C_{1-3}$ alkyl is unsubstituted.

4. The compound, or the pharmaceutically acceptable salt thereof, or the stereoisomer thereof, or the solvate thereof according to claim 3, wherein $R_{3'}$ is methyl.

5. The compound, or the pharmaceutically acceptable salt thereof, or the stereoisomer thereof, or the solvate thereof according to claim 1, wherein $R_a$ and $R_b$ are each independently hydrogen.

6. The compound, or the pharmaceutically acceptable salt thereof, or the stereoisomer thereof, or the solvate thereof according to claim 1, wherein the compound represented by formula (III-a) or formula (III-b) is any one of the following compounds:

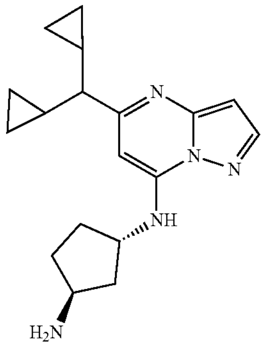

,

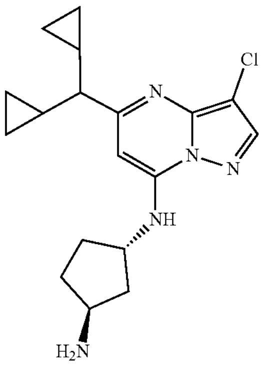

,

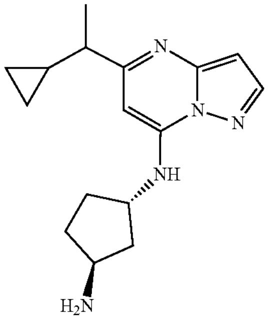

,

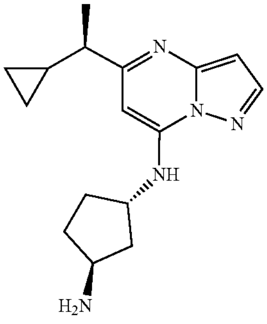

,

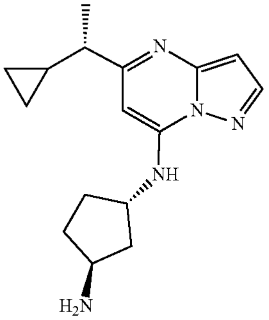

,

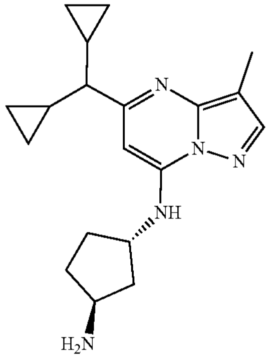

,

-continued
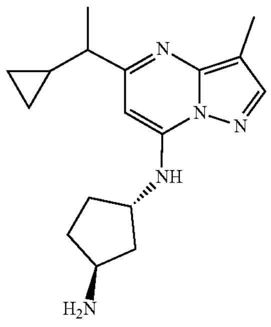
,
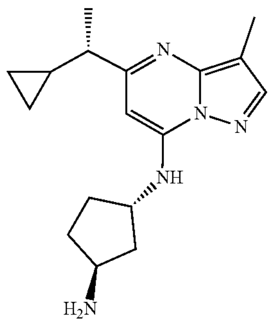
,
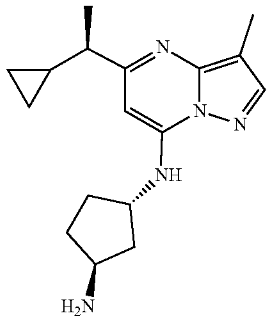
,
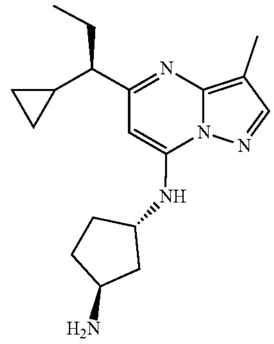
,
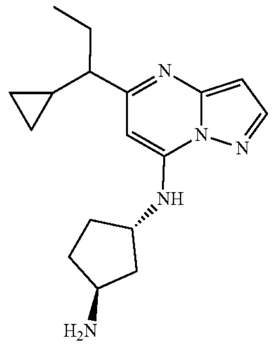
,
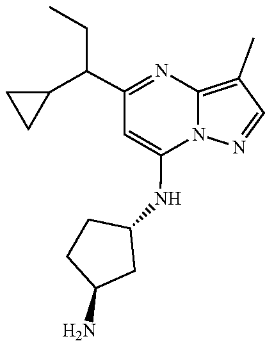
,
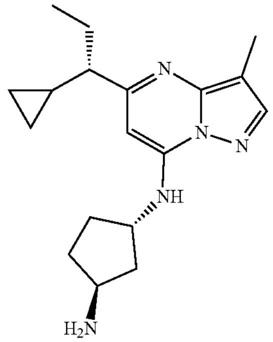
,
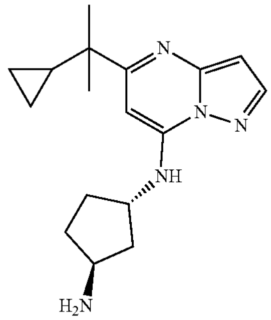
,
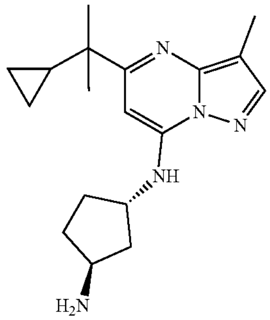
,
-continued
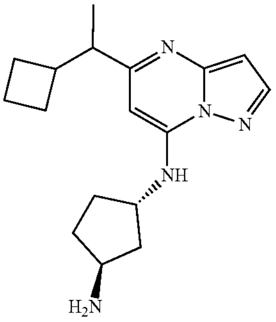
,
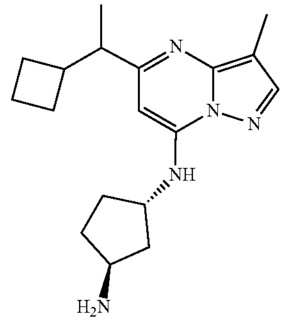
,
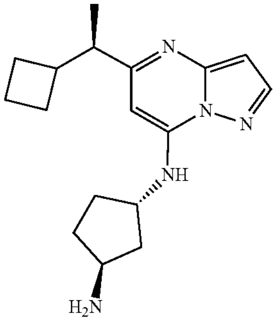
,
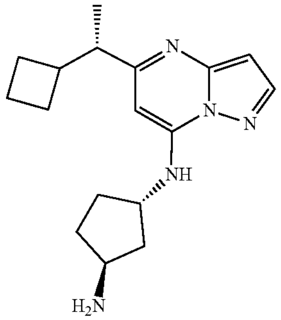
,
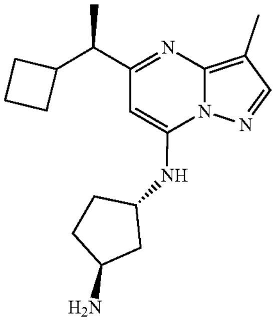
,
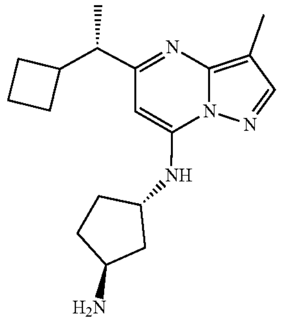
,
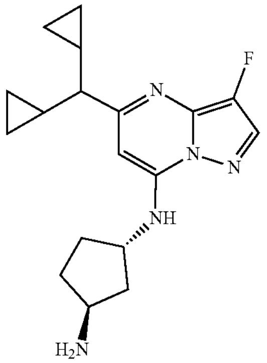
,
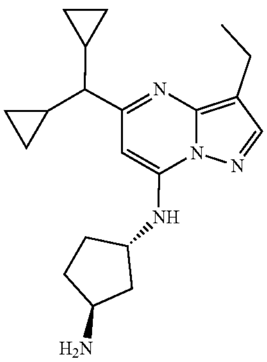
,
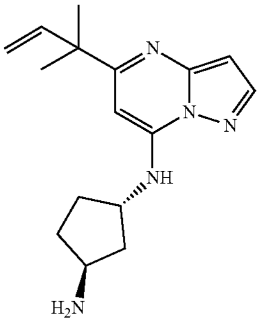
,
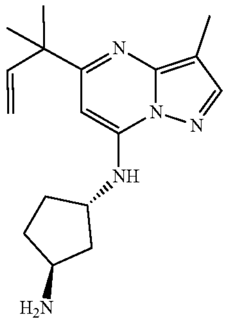
.
7. The compound, or the pharmaceutically acceptable salt thereof, or the stereoisomer thereof, or the solvate thereof according to claim 1, wherein the compound represented by formula (III-a) or formula (III-b) is any one of the following compounds:
Z-20
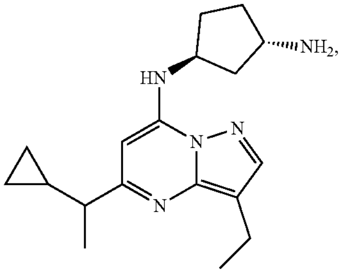
Z-28-P1
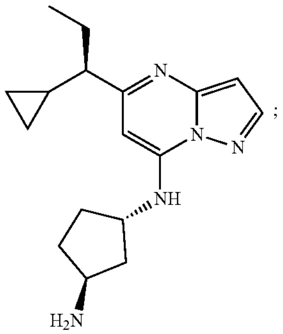
Z-28-P2
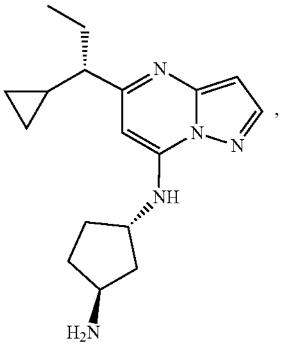
Z-39
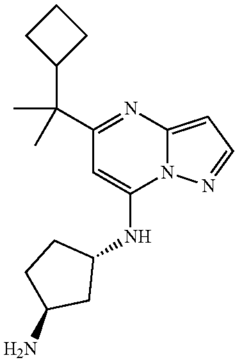
,
-continued
Z-40
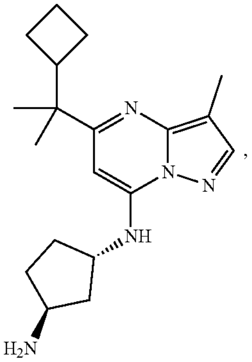
Z-43
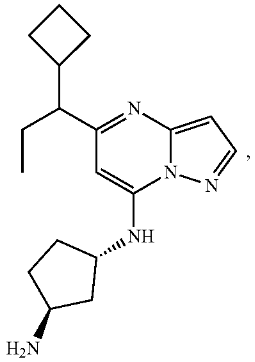
Z-56
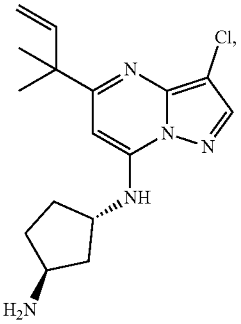
Z-58
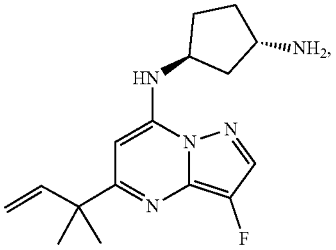
Z-62
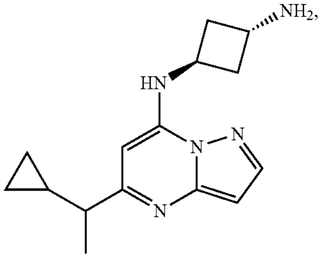

-continued

Z-62-P1

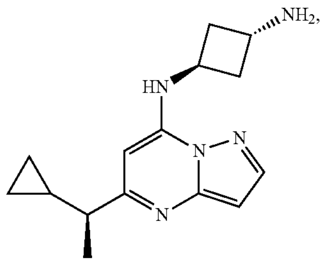

Z-62-P2

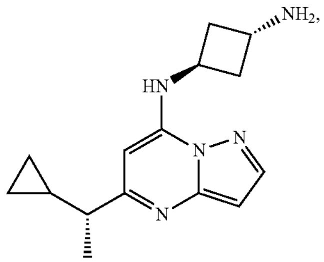

8. A pharmaceutical composition, comprising:

the compound, or the pharmaceutically acceptable salt thereof, or the stereoisomer thereof, or the solvate thereof according to claim 1; and a pharmaceutically acceptable carrier.

9. A method for treating or preventing a hyperproliferative disease, comprising:

administrating the compound, or the pharmaceutically acceptable salt thereof, or the stereoisomer thereof, or the solvate thereof according to claim 1 to a subject in need thereof.

10. The method according to claim 9, wherein the hyperproliferative disease is cancer, and the cancer is selected from the group consisting of pancreatic cancer, breast cancer, ovarian cancer, cervical cancer, and leukemia.

11. The compound, or the pharmaceutically acceptable salt thereof, or the stereoisomer thereof, or the solvate thereof according to claim 1, wherein:

$R_2$ is hydrogen;

$R_3$ is $C_{1-3}$ alkyl or $C_{3-6}$ cycloalkyl; and $R_a$ is hydrogen or $C_{1-3}$ alkyl.

* * * * *